US009070282B2

(12) United States Patent
Clough

(10) Patent No.: US 9,070,282 B2
(45) Date of Patent: Jun. 30, 2015

(54) SMARTPHONE CONTROL OF ELECTRICAL DEVICES

(71) Applicant: Altorr Corporation, Largo, FL (US)

(72) Inventor: Bradford A. Clough, Largo, FL (US)

(73) Assignee: Altorr Corp., Largo, FL (US)

( * ) Notice: Subject to any disclaimer, the term of this patent is extended or adjusted under 35 U.S.C. 154(b) by 66 days.

(21) Appl. No.: 14/157,546

(22) Filed: Jan. 17, 2014

(65) Prior Publication Data

US 2014/0169795 A1 Jun. 19, 2014

Related U.S. Application Data

(63) Continuation-in-part of application No. 13/931,820, filed on Jun. 29, 2013, now Pat. No. 8,884,558, which is a continuation of application No. 13/655,358, filed on Oct. 18, 2012, now Pat. No. 8,476,849, which is a continuation of application No. 12/698,133, filed on Feb. 1, 2010, now Pat. No. 8,310,179.

(60) Provisional application No. 61/164,955, filed on Mar. 31, 2009, provisional application No. 61/148,394, filed on Jan. 30, 2009.

(51) Int. Cl.
H02P 1/00 (2006.01)
G08C 23/04 (2006.01)
G08C 17/02 (2006.01)
G06F 19/00 (2011.01)
G10L 15/26 (2006.01)
G10L 15/08 (2006.01)
A61G 7/015 (2006.01)
A61G 7/018 (2006.01)
A61G 7/10 (2006.01)

(52) U.S. Cl.
CPC ............... *G08C 23/04* (2013.01); *G08C 17/02* (2013.01); *G10L 15/26* (2013.01); *G06F 19/3418* (2013.01); *G10L 2015/088* (2013.01); *G06F 19/345* (2013.01); *A61G 7/015* (2013.01); *A61G 7/018* (2013.01); *A61G 7/1005* (2013.01); *A61G 7/1017* (2013.01); *A61G 7/1042* (2013.01); *A61G 7/1051* (2013.01); *A61G 7/1061* (2013.01); *A61G 7/1065* (2013.01); *A61G 2203/12* (2013.01); *A61G 2203/16* (2013.01); *A61G 2203/20* (2013.01)

(58) Field of Classification Search
CPC .................................................... H02H 7/0851
USPC .......................... 318/266, 265, 264, 256, 255
See application file for complete search history.

(56) References Cited

U.S. PATENT DOCUMENTS 4,435,862 A 3/1984 King et al.
5,247,763 A 9/1993 Hein (Continued)

OTHER PUBLICATIONS

Sourceforge, LCD_TV, Linux Infrared Remote Control, Apr. 9, 2009, http://lirc.sourceforge.net/remotes/vizio/LCD_TV, retrieved from the Internet on Jan. 12, 2014.

(Continued)

*Primary Examiner* — David S Luo
(74) *Attorney, Agent, or Firm* — Michael G. Smith, Esq.

(57) ABSTRACT

In some implementations a non-transitory storage device on a smartphone having a multi-sensory-recognition engine stored thereon is coupled to a microcontroller, a device-controller for an electrical device that is wirelessly coupled to the microcontroller, and at least one of a plurality of sensors is operably coupled to the microcontroller.

16 Claims, 47 Drawing Sheets

(56) References Cited

U.S. PATENT DOCUMENTS

| | | | |
|---|---|---|---|
| 5,809,591 A | 9/1998 | Capaldi et al. | |
| 6,000,077 A | 12/1999 | Cyr | |
| 7,154,397 B2 | 12/2006 | Zerhusen et al. | |
| 7,235,942 B2 | 6/2007 | Nagaoka et al. | |
| 7,315,535 B2 | 1/2008 | Schuman | |
| 8,280,434 B2 * | 10/2012 | Garg | 455/556.1 |
| 2003/0182759 A1 | 10/2003 | Breed et al. | |
| 2003/0188489 A1 | 10/2003 | Shoemaker | |
| 2005/0091928 A1 | 5/2005 | Okulov et al. | |
| 2005/0159275 A1 | 7/2005 | Bullman et al. | |
| 2006/0150332 A1 | 7/2006 | Weismiller et al. | |
| 2006/0223042 A1 | 10/2006 | Epler et al. | |
| 2008/0052831 A1 | 3/2008 | Weismiller et al. | |
| 2009/0139141 A1 | 6/2009 | MacLeod et al. | |
| 2009/0144895 A1 | 6/2009 | Bostelman et al. | |

OTHER PUBLICATIONS

Willie Walker et al., Sphinx-4: A Flexible Open Source Framework for Speech Recognition, SMLI TR2004-0811, 2004, retrieved from the Internet in Aug. 2010 from http://cmusphinx.sourceforge.net/sphinx4/doc/Sphinx4Whitepaper.pdf.

Global Cache, iTach API Specification, PN: 100415-01 ver. 1.5, Aug. 25, 2011, pp. 1 and 11, http://www.globalcache.com/files/docs/API-iTach.pdf, retrieved from the Internet on Jan. 13, 2014, 160 East California Street, PO Box 1659, Jacksonville, Oregon 97530.

* cited by examiner

604

VOICE DATA RECEIVER
604

900

ELECTRONIC DEVICE
CONTROLLER

FIG. 28      OCCUPIED COMMAND SET METHOD

FIG. 36  VOICE / MANUAL CONTROLLED LIGHT SWITCH
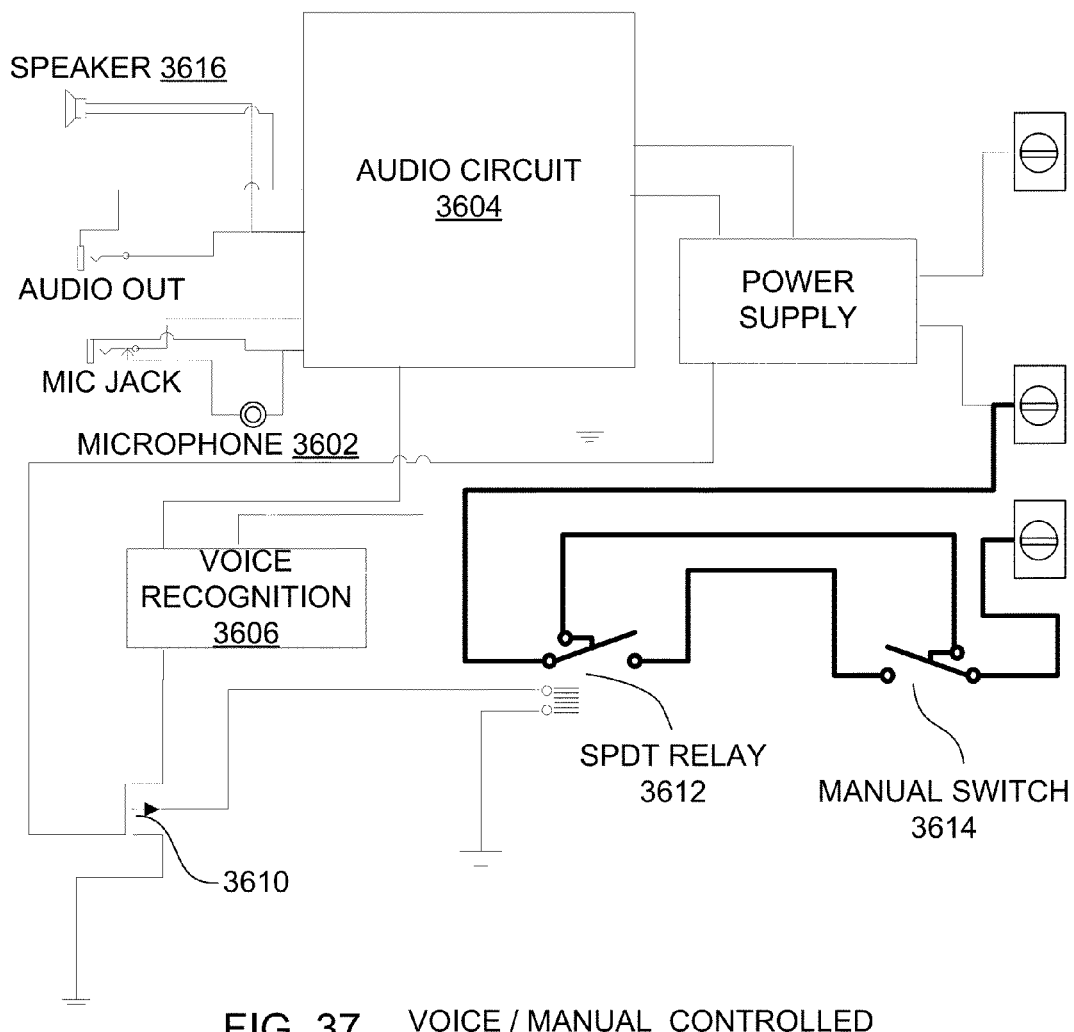
FIG. 37  VOICE / MANUAL CONTROLLED LIGHT SWITCH
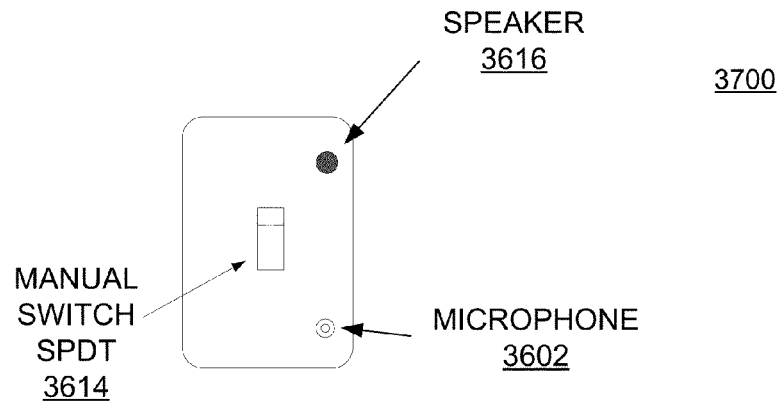

VOICE / MANUAL CONTROLLED LIGHT SWITCH WITH MANUAL AND VOICE CONTROLLED DIMMER CIRCUITRY 4000

VOICE / MANUAL CONTROLLED LIGHT SWITCH WITH MANUAL AND VOICE CONTROLLED DIMMER CIRCUITRY 4100

VOICE CONTROLLED WALL PLUG WITH MANUAL AND VOICE CONTROLLED DIMMER CIRCUITRY 4200

VOICE CONTROLLED WALL PLUG WITH MANUAL AND VOICE CONTROLLED DIMMER CIRCUITRY 4300

SMARTPHONE CONTROL OF ELECTRICAL DEVICES

RELATED APPLICATIONS

This application is a continuation-in-part of, and claims the benefit under 35 U.S.C. 120 of U.S. Original application Ser. No. 13/931,820 filed on 29 Jun. 2013, which is a continuation of, and claims the benefit under 35 U.S.C. 120 of U.S. Original application Ser. No. 13/655,358 filed on 18 Oct. 2012, which is a continuation of, and claims the benefit under 35 U.S.C. 120 of U.S. Original application Ser. No. 12/698,133 filed on 30 Jan. 2009, which claims the benefit under 35 U.S.C. 119(e) of both U.S. Provisional Application Ser. No. 61/164,955 filed on 31 Mar. 2009 and U.S. Provisional Application Ser. No. 61/148,394 filed 1 Jan. 2009.

FIELD OF INVENTION

This disclosure relates to control of electrical devices.

DESCRIPTION OF RELATED ART

As the aging population and workers with disabilities increase, there are very few electrical device(s) available to assist them and those electrical device(s) are limited. Conventional control of the electrical devices has been very limited. The conventional control devices of the electrical devices include tactile control devices that include buttons to direct movement of the lifting device. The tactile control devices require a certain amount of physical dexterity that a particular patient may or may not have. At best, the tactile control devices as currently configured are inconvenient to use for some patients, and under the worse situations, the tactile control devices are impossible to use for other patients.

BRIEF DESCRIPTION

The above-mentioned shortcomings, disadvantages and problems are addressed herein, which will be understood by reading and studying the following specification.

In one aspect, a wireless mobile device controls at least one controllable electrical device from audio speech, by receiving the audio speech that is associated with the at least one controllable electrical device at a microphone of the wireless mobile device, generating speech data that is associated with a vocabulary set of the at least one controllable electrical device from the audio speech, converting the speech data to an ASCII string that is associated with the at least one controllable electrical device at the wireless mobile device, the ASCII string representing control data of the at least one controllable electrical device that is indicated by the audio speech, establishing a WIFI communication path with a WIFI wireless router that is associated with the at least one controllable electrical device at the wireless mobile device; and sending the ASCII string from the wireless mobile device to the WIFI wireless router that is associated with the at least one controllable electrical device through the WIFI communication path.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 36 is an electrical schematic diagram of a voice and manual controlled switch, according to an implementation;

FIG. 37 is a mechanical diagram of a voice and manual controlled switch, according to an implementation;

FIG. 51 is a diagram of a handheld mobile device graphical user interface selected to control a patient bed electrical device;

FIG. 52 is a diagram of a handheld mobile device graphical user interface selected to control a digital video recorder electrical device that is located in a bedroom;

FIG. 53 is a diagram of a handheld mobile device graphical user interface selected to control an electrical devices located in a first bedroom;

FIG. 54 is a diagram of a handheld mobile device graphical user interface selected to control a security camera electrical device located at a front door;

FIG. 55 is a diagram of a handheld mobile device graphical user interface selected to control a digital video recorder electrical device; and FIG. 56 is a diagram of a handheld mobile device graphical user interface selected to control a patient bed electrical device.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into five sections. In the first section, a system level overview is described. In the second section, apparatus of implementations are described. In the third section, implementations of methods are described. In the fourth section, a hardware and the operating environment in conjunction with which implementations may be practiced are described. Finally, in the fifth section, a conclusion of the detailed description is provided.

System Level Overview

A system level overview of the operation of an implementation is described in this section of the detailed description.

Figure 1:
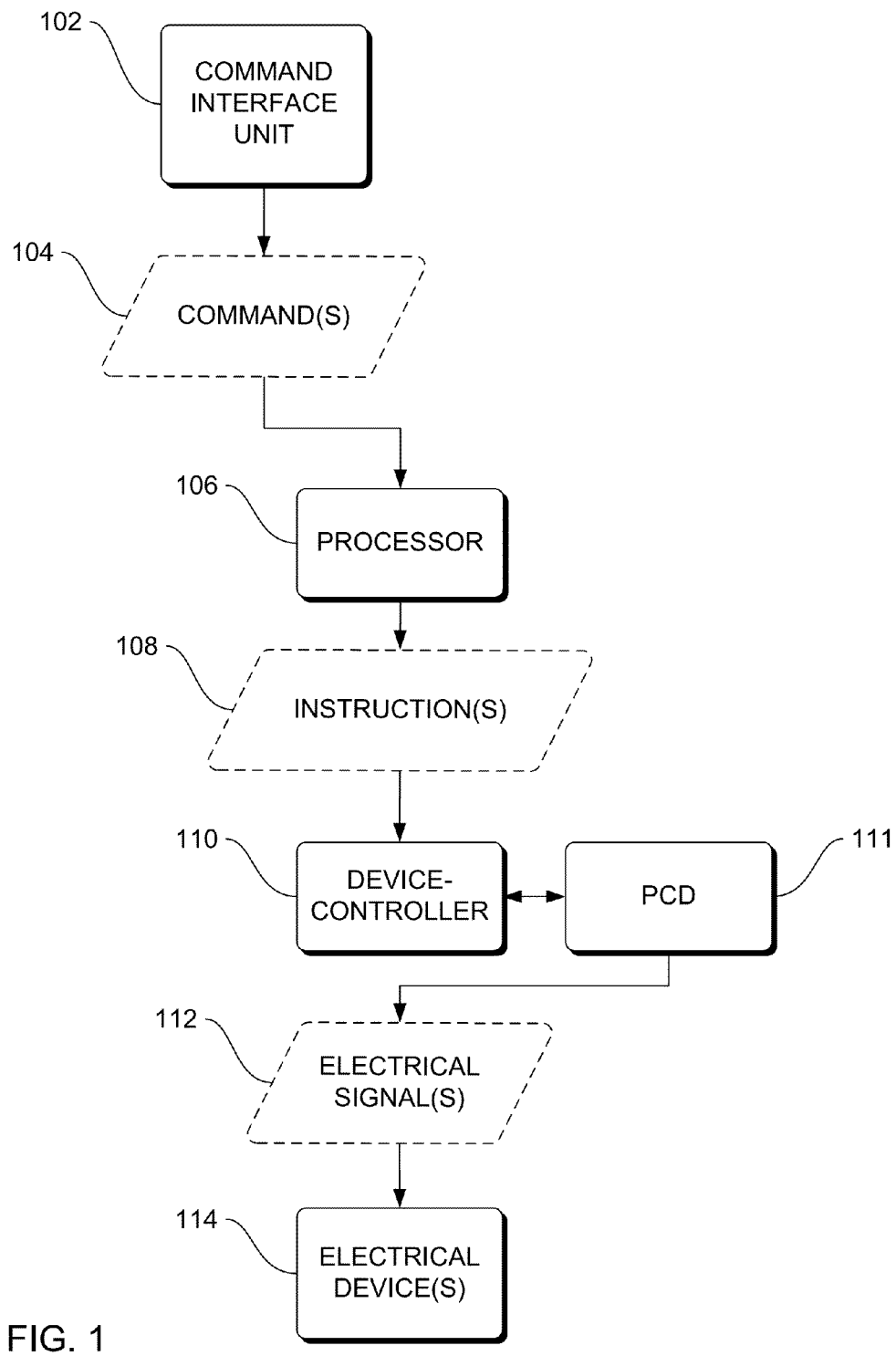
FIG. 1 is a block diagram of an overview of a system to control one or more electrical devices, according to an implementation.

FIG. 1 is a block diagram of an overview of a system 100 to control one or more electrical devices, according to an implementation. System 100 provides a convenient means to control an electrical device, such as an electrically-controlled patient-lifting-device. System 100 gives greater access to electrical devices and services that elderly and physically challenged people are otherwise incapable of controlling, thus increasing independence and quality of life.

System 100 includes a command interface unit 102 that receives information in any one of a number of different communication methods from a human and transmits audio command(s) 104 to a processor 106. Examples of commands 104 to a processor 106 to control a patient-lifting device include "lift up" "move up" "lower down" "move down" "move forward" "forward" "move backward "reverse" "stop" "goto sleep" "sleep" "activate" and "help." One implementation of a number of different interface apparatus for the command interface unit 102 are described in FIG. 4 and another implementation of a number of different interface apparatus for the command interface unit 102 are described in FIG. 5. In some implementations, the command(s) 104 are transmitted from the command interface unit 102 over a radio frequency, without wired or cable transmissions lines, to the processor 106.

The processor 106 in system 100 receives the command(s) 104 and generates one or more instruction(s) 108 that are specifically tailored for a device-controller 110 that accomplish the command(s) 104. In some implementations, the instruction(s) 108 are transmitted over a radio frequency, without wired or cable transmissions lines, to the device controller 110.

Figure 3:
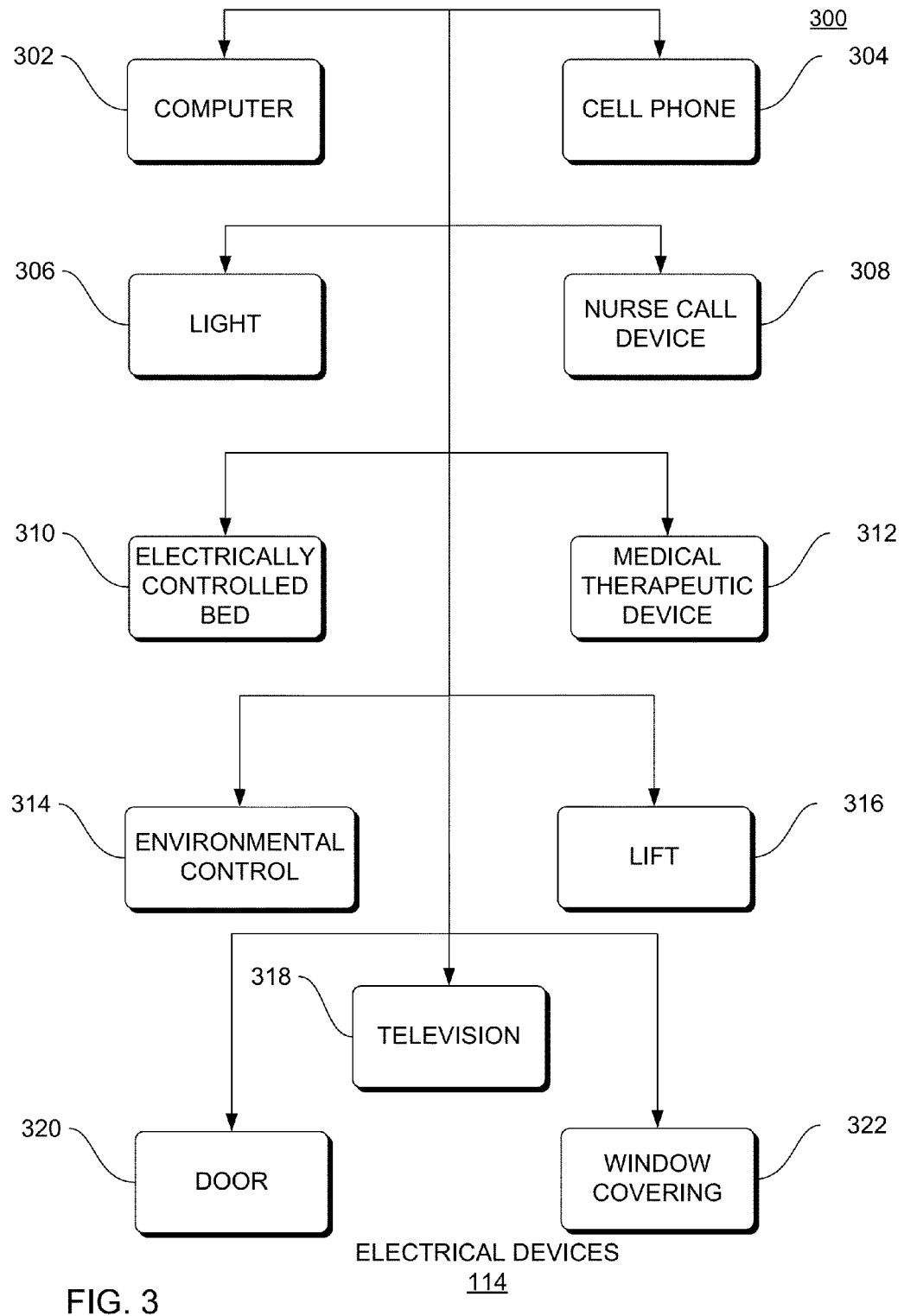
FIG. 3 is a block diagram of a plurality of electrical devices that can be controlled by a device controller.

The device-controller 110 receives the instruction(s) 108 and directs a programmable circuit device (PCD) 111 to generate one or more electric signal(s) 112 that are specifically tailored for an electrical device 114 that accomplish the one or more instruction(s) 108. The PCD 111 transmits the electrical signal(s) 112 to the electrical device 114. In some implementations, the electrical signal(s) 112 are transmitted over a radio frequency, without wired or cable transmissions lines, to the electrical device 114. When the electrical device 114 (e.g. a patient-lifting-device) operates in accordance with the electrical signal(s) 112 from the PCD 111, the electrical device 114 performs the command(s) 104 from the command interface unit 102. Other examples of the electrical device 114 are shown in FIG. 3.

The programmable circuit device (PCD) 111 is a semiconductor chip that contains a library of thousands of electronic components and software that is operable to link the components in such a way that they form one or more circuits. The PCD 111 contains a hardware library, a large number of input devices, controlling circuits and logic circuits which are programmed to interface input and output controls. Because the PCD 111 allows the creation of tens of thousands of different circuit combinations, the PCD 111 is operable to control virtually any device or system. The PCD 111 integrates microprocessors, complex programmable logic devices (CPLD), circuitry and software tools that dynamically create physical circuits and related process logic.

System 100 provides to elderly and physically challenged people greater access and control over the products, appliances and services that allows the elderly and physically challenged people to live a more independence and self-sufficient life. Some implementations of system 100 include a family of device controller(s) 110 and systems that have a mass-market appeal and thereby can be incorporated into everyday products. In some implementations, the electrical device 114 products are controlled without modification by physically challenged people by using a specialized system 100 that is specifically adapted to their individual needs.

In the implementations where the instruction(s) 108 are transmitted over a wireless communication path, and the device controller 110 is located within an exterior housing of the electrical device(s) 114 or the device controller 110 is located within close proximity (e.g. within a few feet) of the electrical device(s) 114, the electrical device(s) 114 are referred to as wireless-controllable-devices. In some implementations, the device controller 110 is integrated not only within the housing of the electrical device, but integrated as a physical fixture within the electrical device 114. The system benefit the general populace while decreasing healthcare costs and dramatically opening the doors of opportunity for elderly and physically challenged people.

One implementation of system 100 includes a family of extremely inexpensive wireless remotely controlled devices (WRCD), in which each WRCD includes a device controller 110 and an electrical device 114 having widespread market appeal in which manufacturers of the electrical device(s) 114 can incorporate the device controller 110 into everyday electrical device(s) 114 such as lamps, dishwashers and machinery. In some implementations, electrical device(s) 114 are controlled by standard remote controls, voice control and special controls for physically challenged people. In some implementations, system 100 includes programmable circuit devices (PCD), wherein each PCD includes thousands of electronic components and software that link the components to form tens of thousands of different circuit combinations. Using a PCD controller, the circuits are configured through software. Because PCD controllers are mass produced and used in many electrical device(s) 114 the cost will be significantly less.

In a healthcare environment, system 100 reduces the need in patients for caregivers, allowing the patient more independence. In addition, system 100 supports cooperative agreements with manufacturers to incorporate WRCD in their electrical device(s) 114. Furthermore, system 100 supports development of infrastructures with nursing homes, hospitals and caregivers to assist in caring for the elderly; and provides patients with increased mobility, freedom and independence allowing the patients to remain in their own homes and communities for as long as possible.

In some implementations, system 100 provides greater access and control of elderly and physically challenged people over household appliance electrical device(s) 114 and services that will allow the physically challenged people to live a more independent and self sufficient life. In some implementations, system 100 includes a designed chip and software system that is a complete stand alone computer. An implementation of system 100 as a voice recognition system is the size of a cell phone, is battery operated and is wireless. In some implementations, system 100 provides a powerful, inexpensive, simple yet sophisticated control system for the elderly and physically challenged people giving them more access, freedom and control. In some implementations, system 100 includes a family of controls and systems that can be incorporated into everyday electrical device(s) 114 by manufacturing companies. By offering extremely inexpensive remote controlled device controller 110, a manufacturer can incorporate the device controller 110 into a wide variety of electrical device(s) 114 such as ceiling fans, lamps, dishwashers, irons, automatic doors and production machinery that is operable to all be controlled remotely, by voice and by specialized controllers. Thus the system benefits the general populace while decreasing healthcare costs and dramatically opening the doors of opportunity for the elderly and physically challenged people.

In residential environments, system 100 reduces the need for caregivers to attend to home-bound patients because of the independence of the command interface unit 102 and the processor, which comprise a programmable voice control device. The safety of the elderly at home presents a constant concern for their loved ones. The thought of a sudden fall or the inability to move around the home with ease presents a continuous concern. Implementations of system 100 that include voice recognition in the command interface unit 102, the voice control recognition assists in daily tasks from dialing 911, in case of an accident, to transporting an individual from the home to a place of safety in the event of a fire. In some implementations of systems 100, the processor 106 can record a path of movement that is stored and replayed for future use; which is invaluable to the installation of home care devices and home care equipment such as rail systems, a home care lift, a transfer lift, a floor lift, a portable lift or a portable ceiling lift which are utilized and easily operated after being trained by a professional to maximize home mobility advantages. The comfort and accessibility of simply turning on the lights before entering a room, creates a safety zone in the home of the elderly.

System 100 provides functions that make the daily tasks of everyday living easier. Once an elderly person understands the functionality of systems 100 and uses system 100, the elderly person will regain their independence, self-esteem and peace of mind. Mobility in the home will increase and the elderly will be able to remain at home longer rather than move to an assisted living residence. Some implementations of systems 100 regulate thermostats, open garage doors and operate electric wheelchair lifts.

In a hospital or nursing home setting, the voice recognition implementation of system 100 proves to be not only economical but practical in purpose. For example, using only 24 programmed voice commands, the environment of a single hospital room unit can be controlled. With the ability to reposition the bed for comfort, guide the movement of patient lifts, turn on and off lights, utilize the television, radio and telephone or signal for a caregiver, these activities are only a voice command away and protect the hospital's employees from injuries while assisting the patient.

In some implementations, system 100 includes a motorized patient lift system that is positionally aware and is controlled to orient and move a patient to any three dimensional location within the system limits. In a first implementation of this system, a patient lift system incorporates a lift motor driving a belt for lifting a patient upwardly off a bed. The motor is mounted for movement along a transverse rail. The transverse bar is mounted for movement in a direction perpendicular to the movement of the motor along the transverse bar, and between two laterally extending bars. By moving the motor along the transverse bar and moving the transverse bar along the laterally extending bars, one may move the patient as desired within the confines of a frame of the system. A frame is defined by the two laterally extending bars which are fixed to two longitudinally extending end bars. Another feature of the system is the ability to record a path of movement that is stored and replayed for future use, which was mentioned earlier also as part of the safety feature on transporting a person to a safe zone in the event of a fire. The objective is for the system to communicate with other positionally aware components to facilitate a process such as an exchange of the patient to a positionally aware wheelchair. This chip and software is interchangeable to adapt to other manufacturer's lift electrical device(s) 114. This chip and software is adapted by manufacturers of motorized wheelchairs such as Quantum Rehab, Quickie® Rhythm™ and BraunAbility. A control component will allow manufactures to create and control a variety of sensory inputs such as voice control, micro switch head controls, puff tube controls or the combination of those controls easily programmed by the end user or the caregiver for the correct functionality. This device will allow a wide variety of sensory inputs in any combination of full and semi electric hospital beds. Four programmable voice commands is operable to reposition the electric beds for comfort and safety. The voice recognition system controls the entire environment of a single hospital room unit. With just twenty four (24) programmable voice controls, the voice recognition system has the ability to reposition the bed for comfort, guide the movement of patient lifts, turn on and off lights, the television, radio and use the telephone or signal for a caregiver, these activities are only a voice command away and will save time, manpower and reduce the risk of injury to employees and patients. Once again, the remote control devise has the ability to assist patients with more mobility, providing them with a sense of heightened security, independence and control.

System 100 provides two significant technical effects. One technical effect is the ability to control the entirety of a physical environment of a physically challenged person through system 100 that in some implementations provides a portable, universal, wireless, control remote device, the voice recognition system. In some implementations, the processor 106 is the size of a cell phone. In some implementations, the processor can generate instruction(s) 108 for an immense variety of electrical devices from over 10,000 command(s) 104 and thus those implementations of system 100 have the capacity to control an immense variety of electrical device(s) 114. In particular, system 100 provides to caregivers and professional healthcare staff an ability to control a hospital room unit, a nursing home room or a bedroom in an assisted living residence. Some of the electrical device(s) 114 in a healthcare environment include telephone; bed; power lift; lights; nurse signal; television; VCR, DVD, radio and medication dispenser. Another technical effect of system 100 is the ability to program the chip and software system of a set of standard switches that enables manufacturers and developers of the standard switches to build the command interface unit 102 and the processor 106 and the device controller 110 into conventional electrical device(s) 114, thus the conventional electrical device(s) 114 are then accessible for physically challenged people and elderly people. An implementation of system 100 as a voice recognition system is a wireless, universal remote voice control system adaptable to any electrical device that is programmed.

While the system 100 is not limited to any particular command interface unit 102, command(s) 104, processor 106, instruction(s) 108, device-controller 110, PCD 111, electric signal(s) 112, and electrical device 114, for sake of clarity a simplified command interface unit 102, command(s) 104, processor 106, instruction(s) 108, device-controller 110, PCD 111, electric signal(s) 112, and electrical device 114 are described.

Apparatus Implementations

In the previous section, a system level overview of the operation of an implementation was described. In this section, the particular apparatus of such an implementation are described by reference to a series of diagrams.

Figure 2:
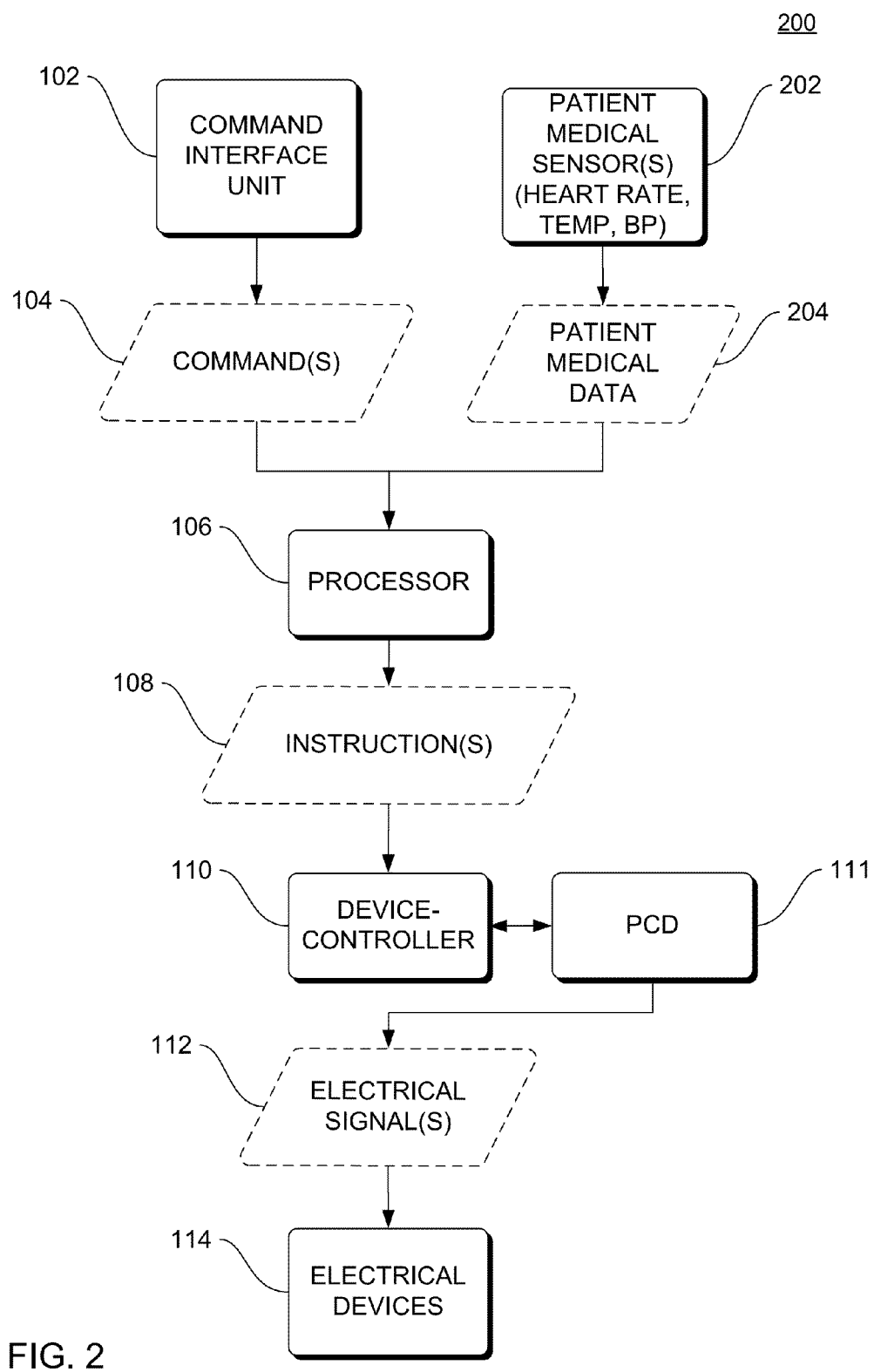
FIG. 2 is a block diagram of apparatus to control one or more electrical devices in reference to patient healthcare condition, according to an implementation.

FIG. 2 is a block diagram of apparatus 200 to control a patient-lifting-device in reference to patient healthcare condition, according to an implementation. Apparatus 200 provides a convenient means to control an electrical device, such as an electrically-controlled patient-lifting-device, in reference to patient healthcare condition.

Apparatus 200 includes one or more sensor(s) 202 of patient condition. Examples of the sensor(s) 202 include heart rate sensor temperature sensor and blood pressure sensor. In apparatus 200, patient healthcare sensor data 204 from the patient healthcare sensor(s) 202 are received by the processor 106. The instruction(s) 108 that are generated by the processor 106 from the command(s) 104 of the command interface unit 102 are generated in reference to the patient healthcare data 204. Thus apparatus 200 generates instruction(s) 108 that ultimately control the electrical device 114 in any manner that is less detrimental to the patient in consideration of the healthcare condition of the patient as indicated by the patient healthcare sensor data 204.

In some implementations of apparatus 200, the command interface unit 102 of apparatus 200 performs voice recognition and interfaces with neural sensors, the neural sensors 202. The neural sensors are operable to identify electric signals naturally produced by the brain and reveal discreet emotional states and conscious thoughts. Sensors 202 detect as head movement, head rotation, eye and eyelid movement, lip movement, hand movement, diaphragm movement, nose movement, tongue movement, muscle movement, heart and respiratory rate, body temperature and skin electrical conductivity. The PCD can be adapted operate patient-lifting-device by a wireless, universal, voice remote controllable program. In some implementations, the command interface unit 102 and the PCD 111 are adapted to the analog signal process of a particular electrical device 114 such as patient-lifting-device manufactured by Molift™ AS of Ole Deviks vei 44, 0668 Oslo, Norway. The interface unit 102 and the PCD 111 is interchangeable to adapt to other manufacturer's lift electrical device(s) 114, such as wheelchair lifts and paratransit conversions in public-use transportation for the disabled.

The apparatus 200 is so simple to use that a caregiver will be able to customize apparatus 200 to the physical and mental capabilities of a patient to control various electrical device(s) 114, regardless of whether the electrical device 114 is a motorized wheelchair, a ceiling lift, home medical equipment or a household appliance. For example, by programming voice commands to the command interface unit 102, an operator will be able to adjust a hospital bed position, call for a caregiver, and turn off and on the lights independently. The voice commands to adjust the position of a bed will save caregivers, nursing homes and hospital staff hundreds of man hours, thereby saving time and money not to mention the reduced risk of injury.

FIG. 3 is a block diagram of a plurality of electrical devices 300 that can be controlled by a device controller. Each of the electrical devices 300 in FIG. 3 are examples of the electrical device 114 in FIG. 1 and FIG. 2. Device controller 110 in FIG. 1 is one example of the device controller.

One example of an electrical device that is controlled by a device controller is a computer 302. Another example of an electrical device that is controlled by a device controller is a cell phone or smartphone 304. A further example of an electrical device that is controlled by device controller is a light 306 or other illumination device. Yet another example of an electrical device is controlled by a device controller is a nurse call device 308. Still yet another example of an electrical device that is controlled by a device controller is an electrically controlled bed 310. Still yet a further example of an electrical device that is controlled by a device controller is a medical therapeutic device 312 such as an intravenous fusion device. One more example of an electrical device that is controlled by a device controller is an environmental control 314 such as a heating an air-conditioning unit. An additional example of an electrical device that is controlled by a device controller is a patient-lifting-device 316. A different example of an electrical device that is controlled by a device controller is a television 318. Yet one more example of an electrical device that is controlled by a device controller is a door 320 that includes actuation apparatus to open and close and lock and unlock the door 320. Still an additional example of an electrical device that is controlled by a device controller is a window covering 322 such as shades or blinds that include actuation apparatus to open and close the window covering 322.

Figure 4:
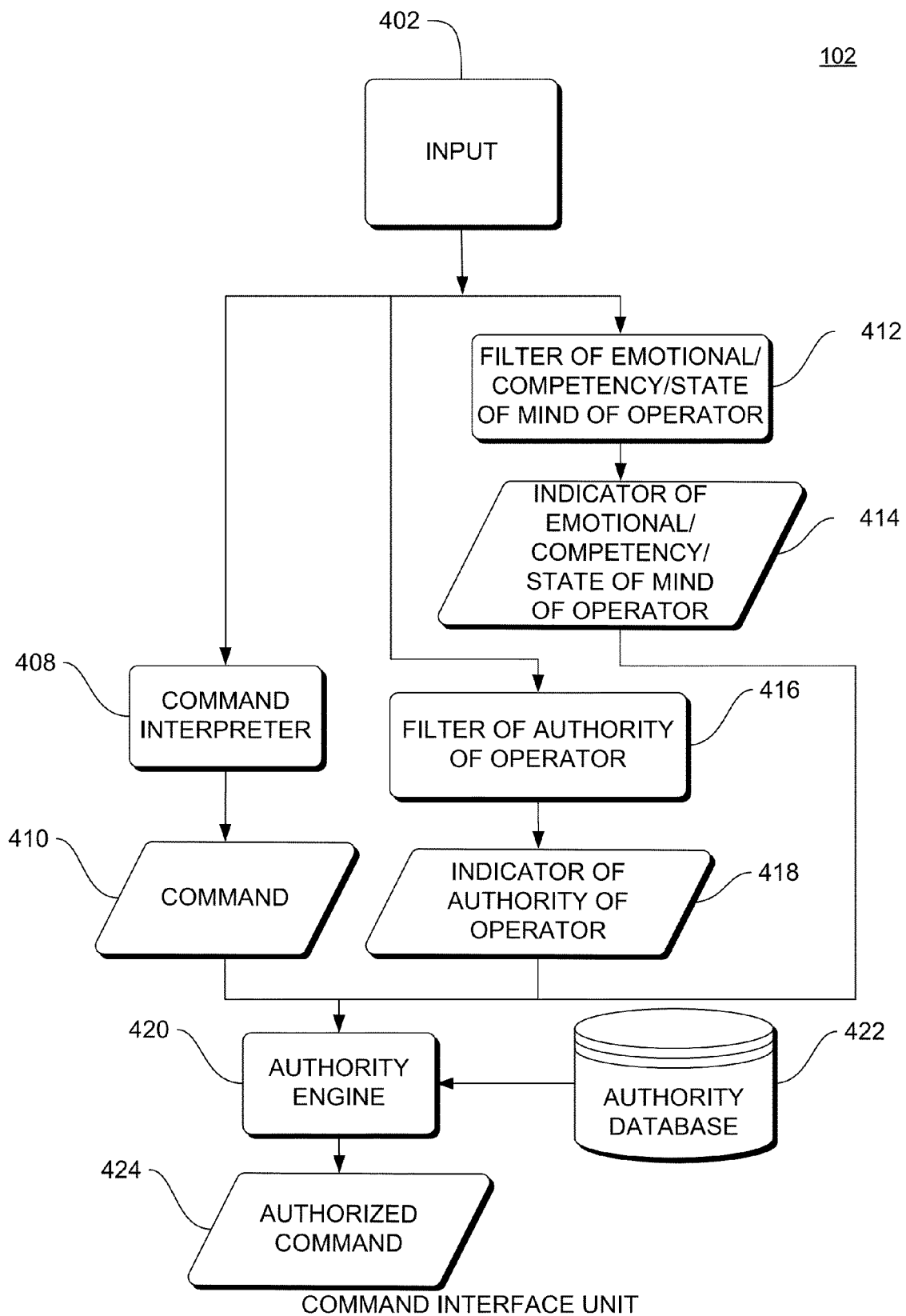
FIG. 4 is a block diagram of a command interface unit apparatus that according to an implementation receives information from a human and generates command(s) from the human information, in reference to authority of the human and the state of the mind of the human.

FIG. 4 is a block diagram of a command interface unit apparatus 400 that according to an implementation receives information from a human and generates command(s) 104 from the human information, in reference to authority of the human and the state of the mind of the human. Apparatus 400 provides command(s) 104 that are suitable to be processed by a processor in control of a patient-lifting-device that are generated in reference to the authority in the state of mind of the human. Apparatus 400 is one implementation of the command interface unit 102 and FIG. 1 and FIG. 2.

The command interface unit 102 shown in FIG. 4 includes an input device 402 that receives information in any one of a number of different communication methods. One implementation of a number of different input devices 402 is described in FIG. 6. The received information is processed in a three-pronged approach. In a first prong, the information is processed by a command interpreter 408. The command interpreter analyzes the information and extracts a command 410 from the information. Examples of commands 410 include "lift up" "move up" "lower down" "move down" "move forward" "forward" "move backward "reverse" "stop" "goto sleep" "sleep" "activate" and "help." In a second prong, the information is processed by a state-of-mind filter 412. The state-of-mind filter 412 analyzes the information and extracts from the information indicators of the emotional state of the operator, indicators of the competency of the operator, and/or indicators of the state-of-mind of the operator 414. In a third prong, the information is processed by an authority filter 416. The authority filter 416 analyzes the information and extracts from the information an indicator 418 of the authority of the operator. The identification of an individual by the authority filter 416 can be done through biometric identification such as voice identification, fingerprint identification or through external means such as a identification badge.

An authority engine 420 receives the command 410, the state-of-mind 414 and the indicator of authority of the operator 418. The authority engine 420 analyzes the command 410, the state-of-mind 414 and the indicator of authority of the operator 418 in reference to an authority database 422. In one implementation the authority engine 420 determines whether or not the command 410 is authorized by the authority of the operator 418. If the command 410 is not authorized by the authority of the operator 418, the command 410 is rejected. In another implementation the authority engine 420 determines whether or not the state-of-mind 414 of the operator is of a sufficient level for the command 410. If the state-of-mind 414 for the operator is not of a sufficient level for the command 410, the command 410 is rejected. If the command 410 is rejected (e.g. if the authority of the operator 518 is insufficient or the state-of-mind 414 of the operator is insufficient) a rejection process is initiated. In one implementation, the rejection process includes notifying a nurse of the rejection. In some implementations, no notice of the nurse is provided until the number of rejections equals or exceeds a threshold number of rejections w/in a predetermined amount of time.

If the authority engine 420 determines that both the state-of-mind 414 and the authority 418 of the operator are sufficient for the command 410, the authority engine 420 generates or designates an authorized command 424 from the command 410.

Figure 5:
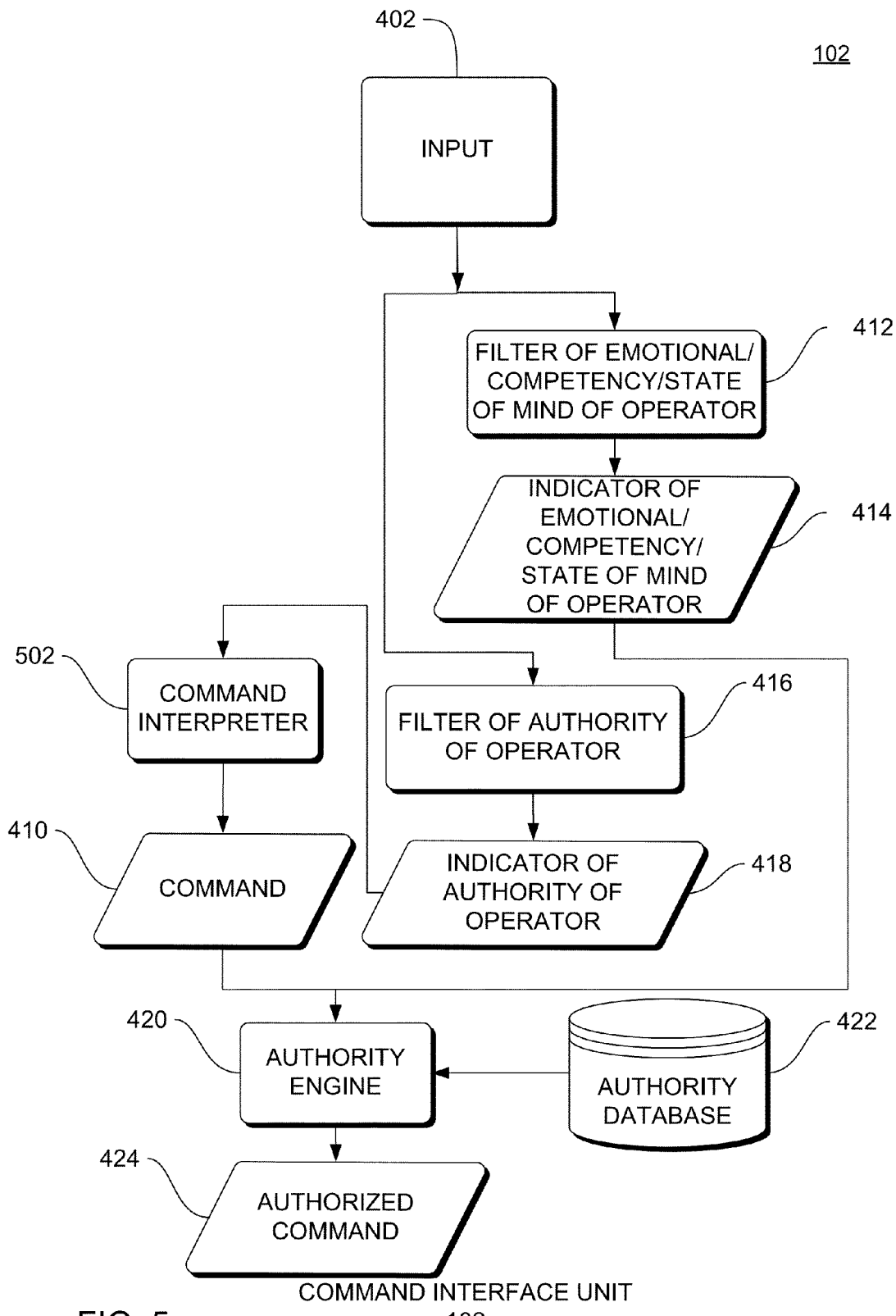
FIG. 5 is a block diagram of a command interface unit apparatus that according to an implementation receives information from a human and generates command(s) from the human information, in reference to authority of the human and the state of the mind of the human.

FIG. 5 is a block diagram of a command interface unit apparatus 500 that according to an implementation receives information from a human and generates command(s) 104 from the human information, in reference to authority of the human and the state of the mind of the human. Apparatus 500 provides command(s) 104 that are suitable to be processed by a processor in control of a patient-lifting-device that are generated in reference to the authority in the state of mind of the human. Apparatus 500 is one implementation of the command interface unit 102 and FIG. 1 and FIG. 2.

The command interface unit 102 shown in FIG. 5 includes an input device 502 that receives information in any one of a number of different communication methods. One implementation of a number of different input devices 502 is described in FIG. 6. The received information is processed in a two-pronged approach. In a first prong, the information is processed by an authority filter 416. The authority filter 416 analyzes the information and extracts from the information an indicator 418 of the authority of the operator. Thereafter, the information is processed by a command interpreter 502. The command interpreter analyzes the information and extracts a command 410 from the information. Examples of commands 410 include "lift up" "move up" "lower down" "move down" "move forward" "forward" "move backward "reverse" "stop" "goto sleep" "sleep" "activate" and "help." In a second prong, the information is processed by a state-of-mind filter 412. The state-of-mind filter 412 analyzes the information and extracts from the information indicators of the emotional state of the operator, indicators of the competency of the operator, and/or indicators of the state-of-mind of the operator 414.

An authority engine 412 receives the command 410, the state-of-mind 414 and the indicator of authority of the operator 418. The authority engine 420 and analyzes the command 410, the state-of-mind 414 and the indicator of authority of the operator 418 in reference to an authority database 422. In one implementation the authority engine determines whether or not the command 410 is authorized by the authority of the operator 418. If the command 410 is not authorized by the authority of the operator 418, the command 410 is rejected. In another implementation the authority engine 420 determines whether or not the state-of-mind 414 of the operator is of a sufficient level for the command 410. If the authority for the operator is not of a sufficient level for the command 410, command 410 is rejected. If the authority for the operator is of a sufficient level for the command 410, command 410 is accepted.

Figure 6:
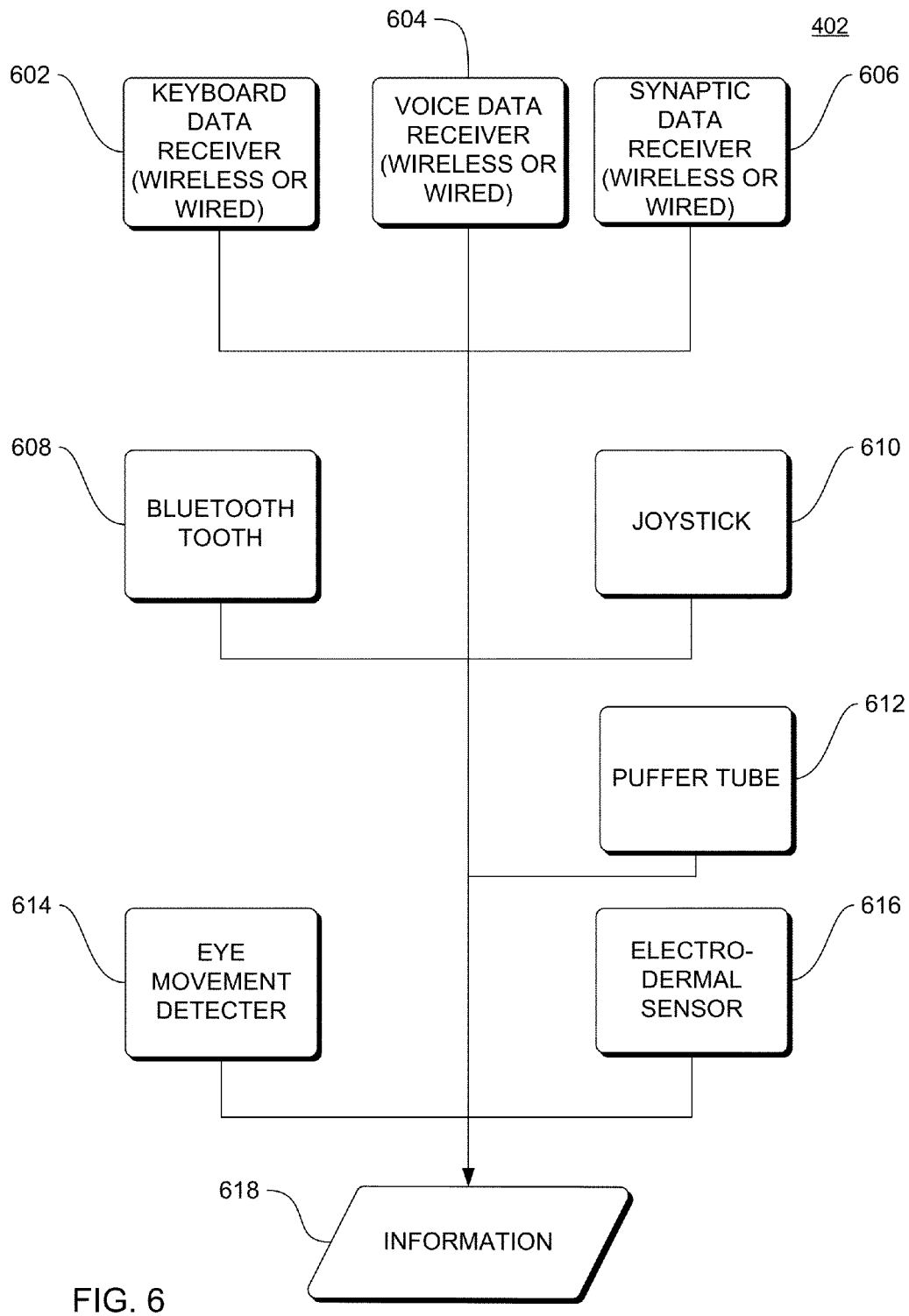
FIG. 6 is a block diagram of a plurality of input devices that receive information in any one of a number of different communication methods, according to an implementation.

FIG. 6 is a block diagram of a plurality of input devices 600 that receive information in any one of a number of different communication methods, according to an implementation. Input devices 600 are implementations of the input devices 402 and FIG. 4 and FIG. 5.

Input devices 402 include a conventional keyboard data receiver 602, commonly known as a keyboard. In some implementations the keyboard includes alphanumeric keys for entering alphanumeric data. Input devices 402 also include an audio data receiver 604. Input devices also include a synaptic data receiver 606. The receivers 602, 604 and 606 can be implemented either with a wireless connection to the command interface unit 102 and/or with a wired connection to the command interface unit 102. The receivers 602, 604 and 606 capture information 618 from an operator that is processed by the command interface unit 102 in FIG. 1, FIG. 2 and/or FIG. 4.

Another example of an input device 402 is a pressure sensitive device (piezo electric device) 608 mounted on and/or in the top of a tooth, that detects/senses pressure and transmits the pressure reading via a wireless connection (e.g. a Bluetooth communication link, or Zigbee communication link) to a processor. The pressure reading/measurement and/or time duration of the pressure reading/measurement is interpreted as an indicator or command to an external device, such as an indicator of a speed and/or direction of a lift device. Specifications for the Bluetooth communication link are published by the Bluetooth Special Interest Group located at 500 108th Avenue NE, Suite 250, Bellevue, Wash. 98004 Phone Number: +1.425.691.3535. Specifications for the ZigBee communication link are published by the ZigBee Alliance located at 2400 Camino Ramon, Suite 375, San Ramon, Calif. 94583. Some implementations the wireless tooth device tooth also detects/senses audio vibrations and transmits representations of the audio vibrations via the wireless connection to the processor. The representations of the audio vibrations are interpreted as an indicator or command to an external device, such as an indicator of a speed, amplitude or throttle (variation of power output) and/or direction of a lift device. The audio vibrations include vibrations transmitted through the solid matter of the tooth and the jaw bone and/or audio vibrations transmitted through the air and the mouth surrounding the audio receiver. Various implementation of the device mounted on a tooth include audio microphone, temperature monitor, saliva acidity sensor, pulse monitor sensor, voice vibration sensor (to sense jawbone vibrations), and with bit control for throttling of the speed of the patient-lifting-apparatus.

Other examples of an input device 402 include a joystick 610, a puffer tube 612, an eye movement detector 614, and an electro-dermal anxiety sensor 616.

Figure 7:
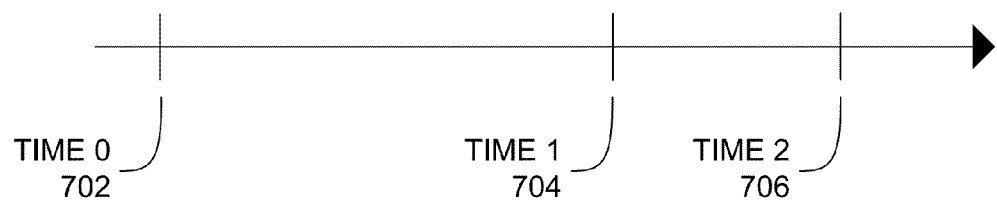
FIG. 7 is a diagram of a timeline to control a patient-lifting-device, according to an implementation involving trigger override command set words.

FIG. 7 is a diagram of a timeline 700 to control a patient-lifting-device, according to an implementation involving trigger override command set words. While audio is received after time-0 702, a determination is made as to whether or not the volume of the audio is above a threshold for at least a predetermined amount of time between time-1 704 and time-2 706. The audio level being above the threshold for predetermined amount of time between time-1 704 and time-2 706 is interpreted to indicate a possible emergency situation which might be dangerous to operate the patient-lifting apparatus. One example of the threshold volume of audio in method 1500 is 90 dB, however other implementations of other threshold levels of audio volume are implemented. If the audio level is determined to be not above the threshold for the predetermined amount of time between time-1 704 and time-2 706, audio is continued to be received. If the audio level is greater than the audio volume threshold for at least the predetermined amount of time between time-1 704 and time-2 706, a safety procedure is performed. Examples of the safety procedure are stopping movement of the patient-lifting-device, reversing movement, and reversing a previous action. After performing the safety procedure, audio is received starting at time-0 702. In some implementations the amount of predetermined time and/or the threshold level of audio volume can be modified through a user configuration interface.

Figure 8:
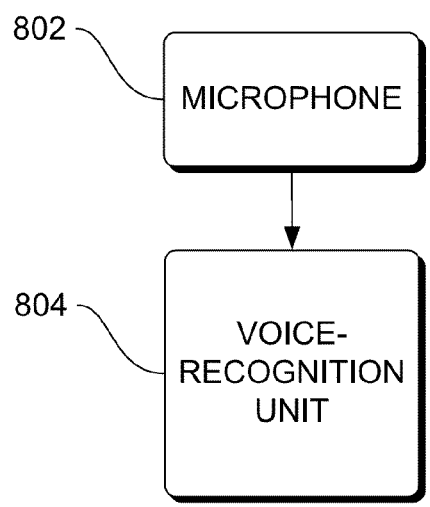
FIG. 8 is a block diagram of a voice data receiver that receives audio information, according to an implementation.
Figure 33:
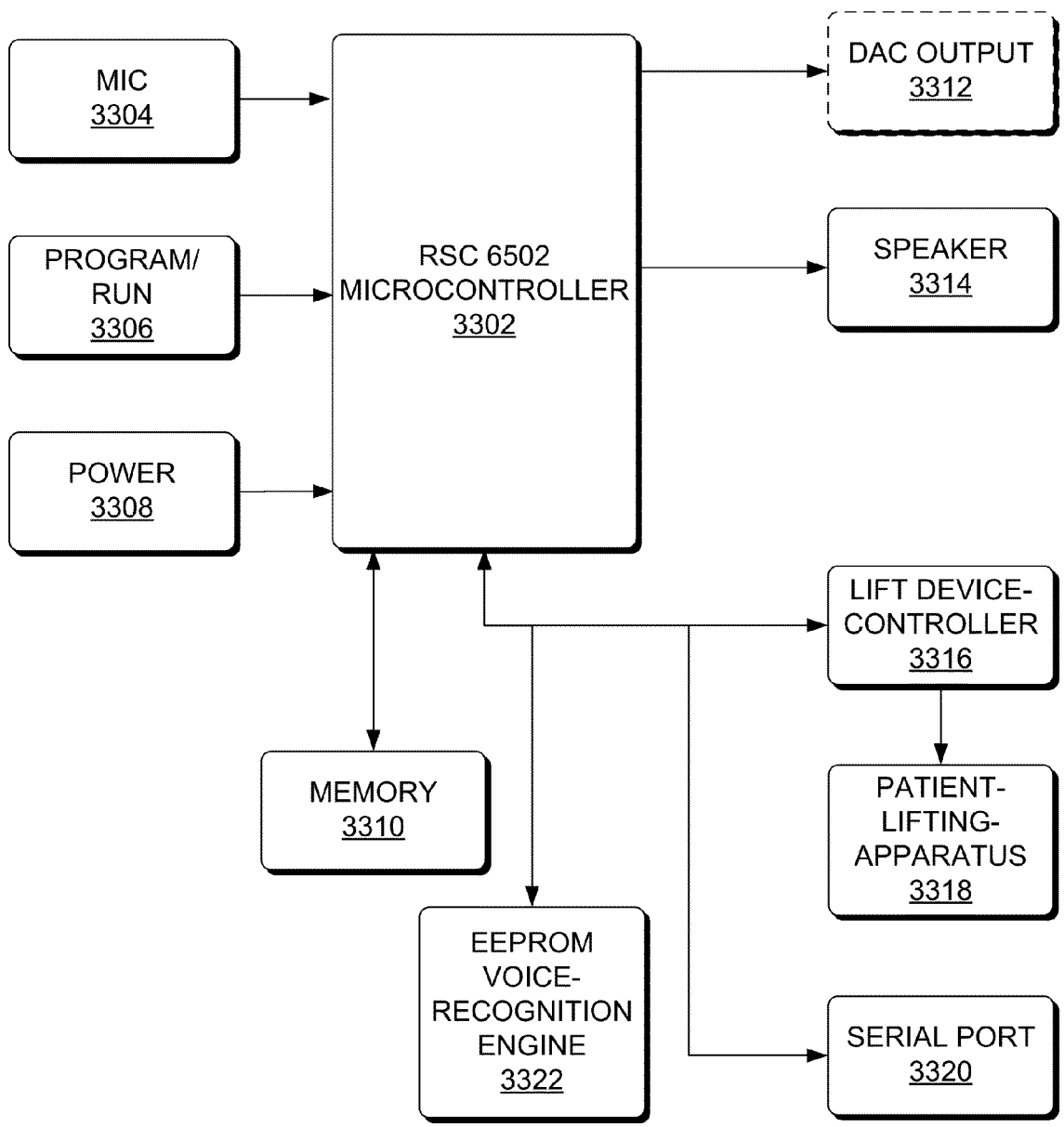
FIG. 33 is a block diagram of a voice-recognition unit for a patient-lifting-apparatus, according to an implementation.
Figure 34:
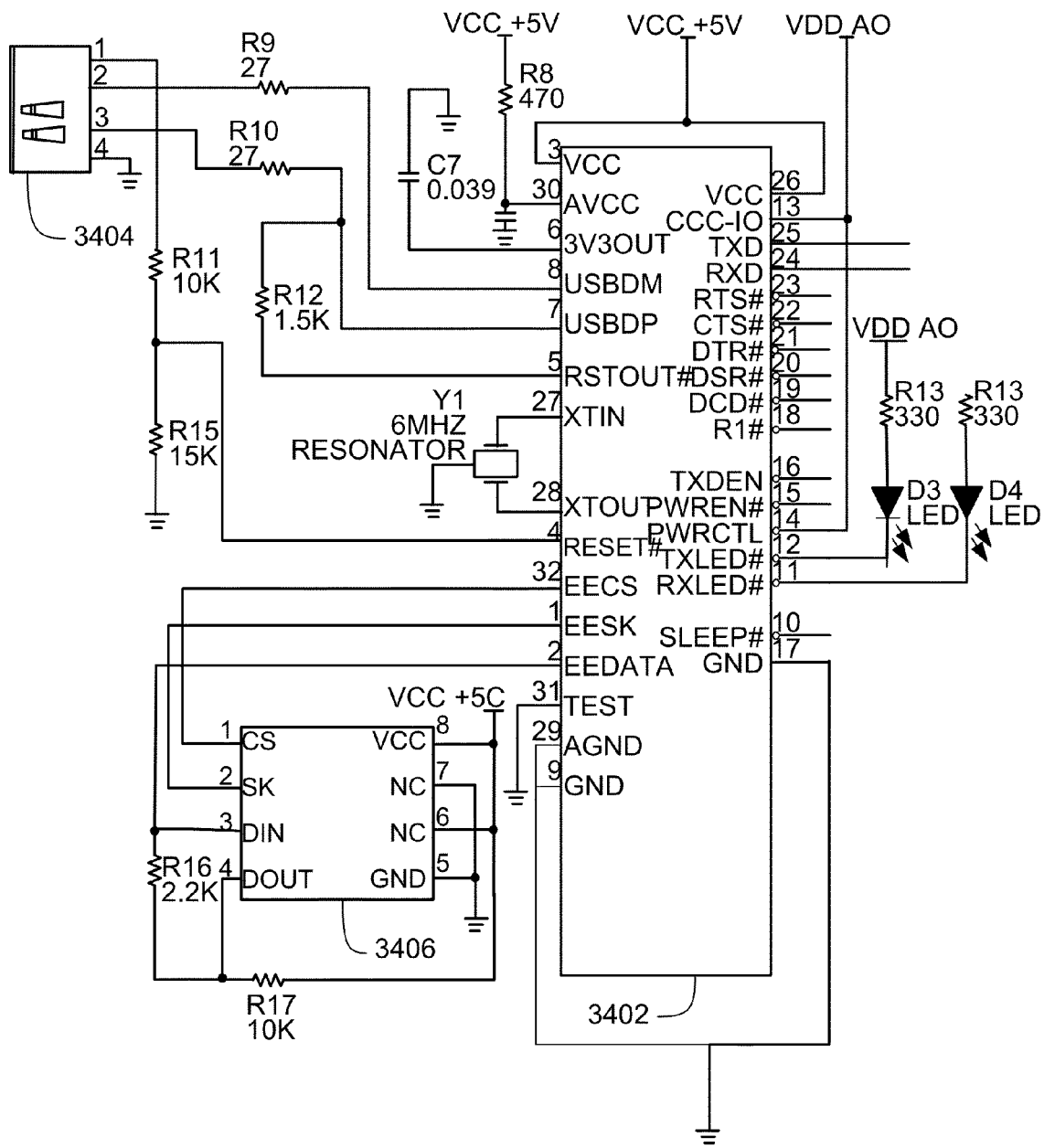
FIG. 34 is an electrical schematic diagram of a voice-recognition apparatus to control a patient-lifting-apparatus, according to an implementation.

FIG. 8 is a block diagram of a voice data receiver 800 that receives audio information, according to an implementation. Voice data receiver 604 in FIG. 8 is one implementation of the voice data receiver 604 in FIG. 6. The voice data receiver 604 in FIG. 8 includes a microphone 802 that is operably coupled to a voice-recognition unit 804. In some implementations, the voice-recognition unit 804 includes a component (not shown)

that suppresses or filters background environmental noise. Voice-recognition apparatus 3300 in FIG. 33 shows an implementation of voice-recognition unit 804. Voice-recognition apparatus 3400 in FIG. 34 shows an implementation of voice-recognition unit 804.

In some implementations the microphone 802 is located in close proximity to the mouth of the speaker in order to obtain clear audio data from the speaker. For example in some further implementations, the microphone 802 is located on a Bluetooth enabled earpiece. In other implementations, the microphone 802 is mounted on the end of a stalk of a headset. In other implementations, the microphone is mounted on a lapel clip.

Figure 9:
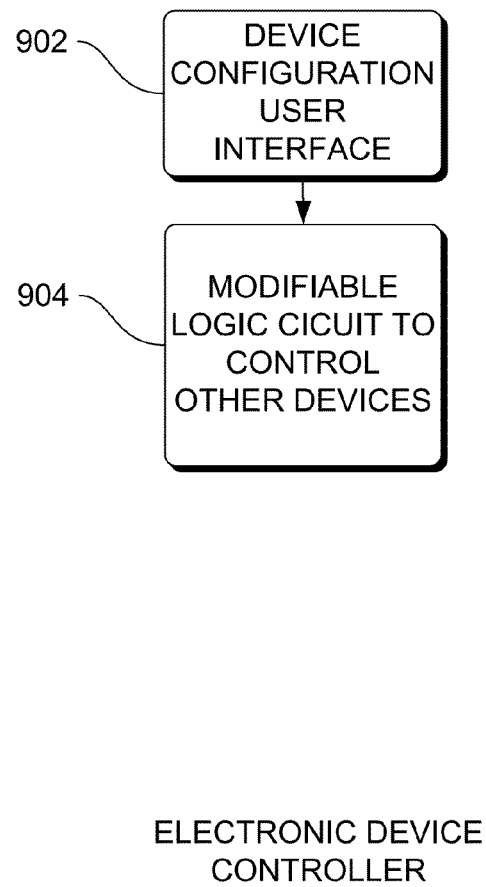
FIG. 9 is a block diagram of a patient-lifting-device controller that receives instructions and generates electrical signals that control a patient-lifting-device, according to an implementation.

FIG. 9 is a block diagram of a patient-lifting-device controller 900 that receives instructions and generates electrical signals that control a patient-lifting-device, according to an implementation. Lift controller 900 is one example of system 100 in FIG. 1 and apparatus 200 in FIG. 2. The patient-lifting-device controller 900 includes a user interface 902 for device configuration that is operable to display, receive and/or store device configuration information for a patient-lifting-device, such as lift 112 in FIG. 1 and FIG. 2. The device configuration user interface 902 is operably coupled to a modifiable logic circuit 904 that is operable to control the lift.

In one implementation, the modifiable logic circuit 904 is a field-programmable gate-array (FPGA) circuit in reference to the device configuration. In the FPGA implementation, the FPGA circuit is operable to receive digital audio input, and extract a command (e.g. command 104 in FIG. 1) that is relevant to a patient-lifting-device (e.g. electrical device 114 in FIG. 1) and the patient-lifting-device controller 900 includes a transmitter that is operable to send the command to a patient-lifting-device-controller (e.g. 111 in FIG. 1).

Figure 10:
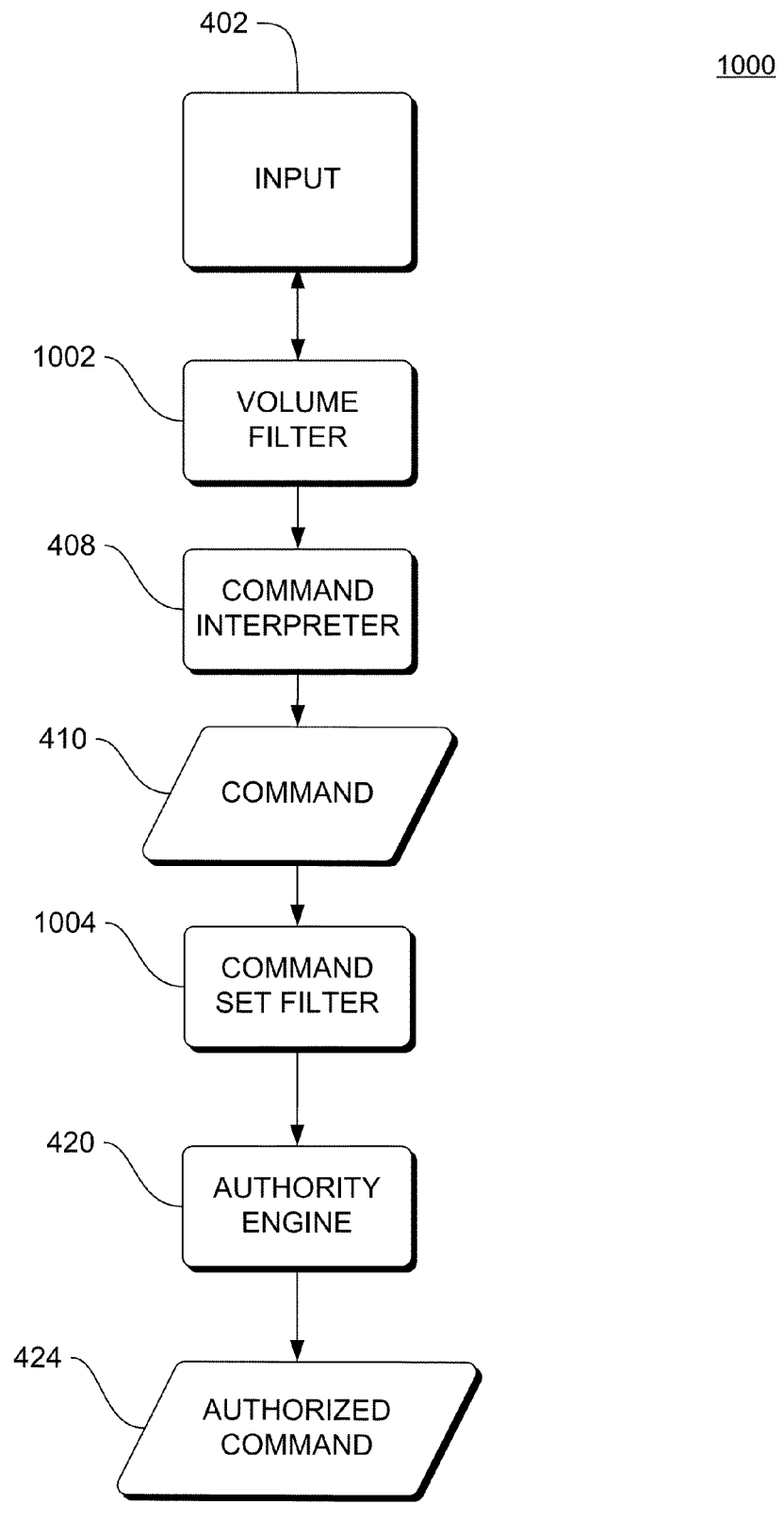
FIG. 10 is a block diagram of a voice-recognition unit that receives audio information and generates commands that control a patient-lifting-device, according to an implementation.

FIG. 10 is a block diagram of a voice-recognition unit 1000 that receives audio information and generates commands that control a patient-lifting-device, according to an implementation. Voice-recognition unit 1000 includes an input device 402 that receives information in any one of a number of different communication methods. Examples of communication methods include audio and/or synaptic communication.

Figure 19:
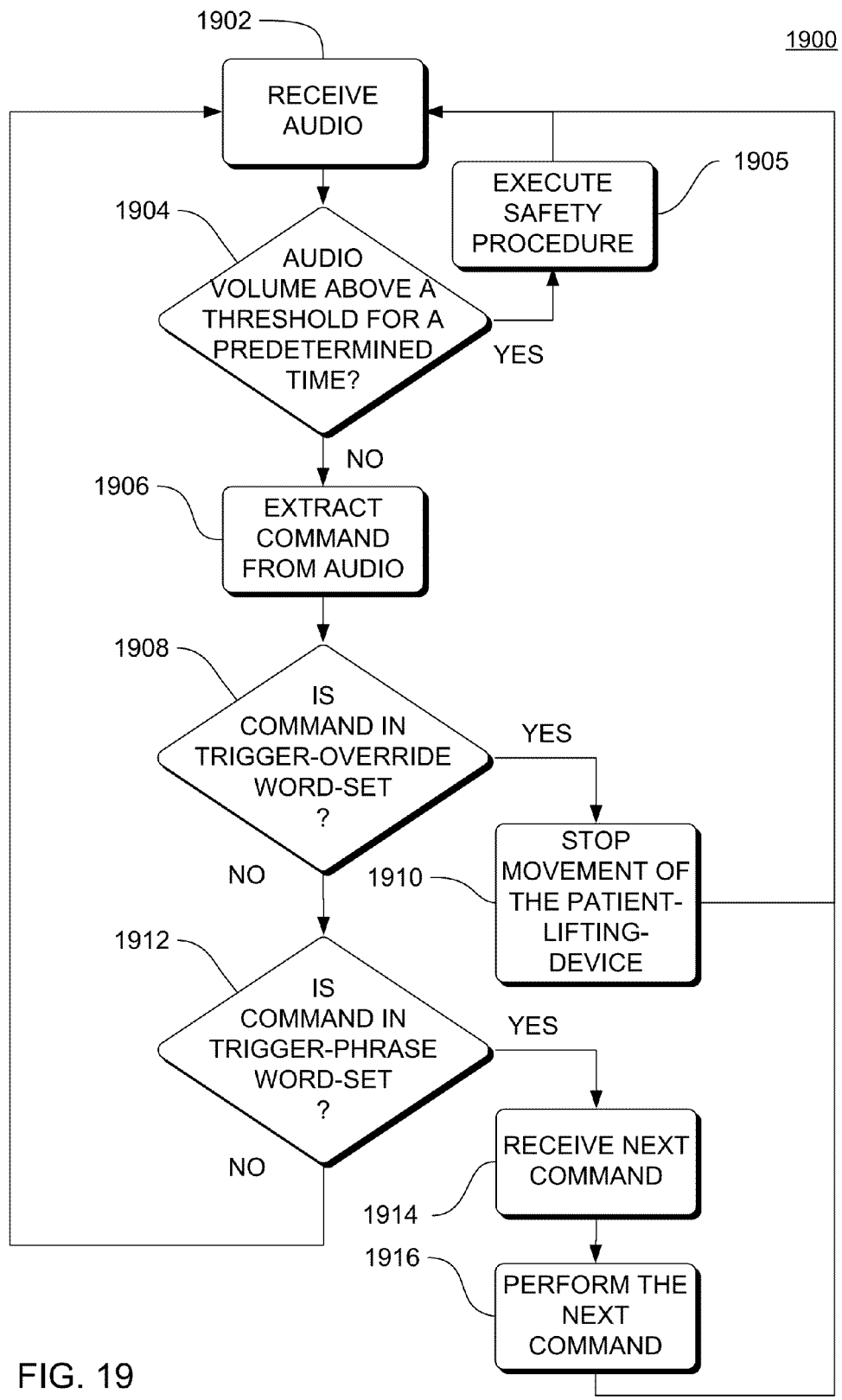
FIG. 19 is a flowchart of a method to control a patient-lifting-device, according to an implementation involving trigger words.
Figure 20:
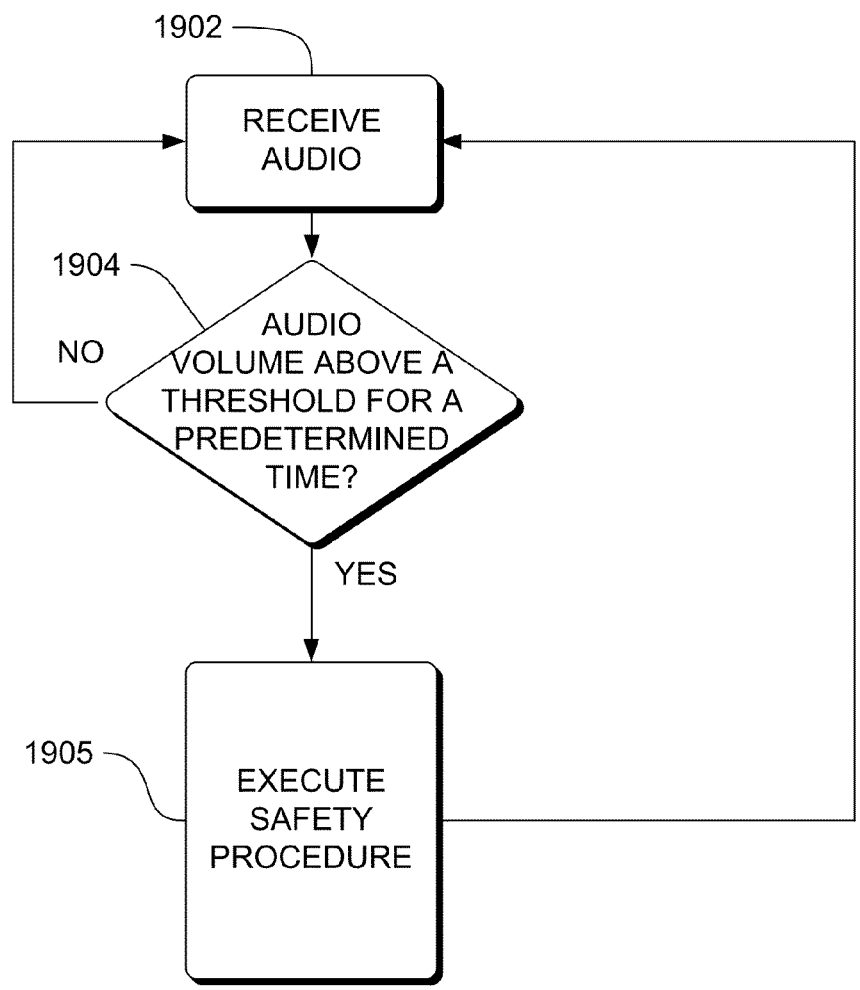
FIG. 20 is a flowchart of a method to control a patient-lifting-device, according to an implementation involving trigger override command set words.

Voice-recognition unit 1000 also includes a volume filter 1002 that performs action 1904 in FIG. 19 and/or action 2004 in FIG. 20 on the information received from the input device 402.

The information received from the input device is processed by a command interpreter 408. The command interpreter analyzes the information and extracts a command 410 from the information.

Some implementations of voice-recognition unit 1000 includes a command set filter 1004 that includes one or more filters of the command set. For example, in some implementations, the command set filter 1004 includes the authority filter 416 of FIG. 4. Some implementations of the command set filter 1004 also include the state-of-mind filter 412 of FIG. 4. The implementations of apparatus 100 that include the command set filter 1004 also include an authority engine 420 as described in FIG. 4. The authority engine 420 generates an authorized command 424.

Figure 11:
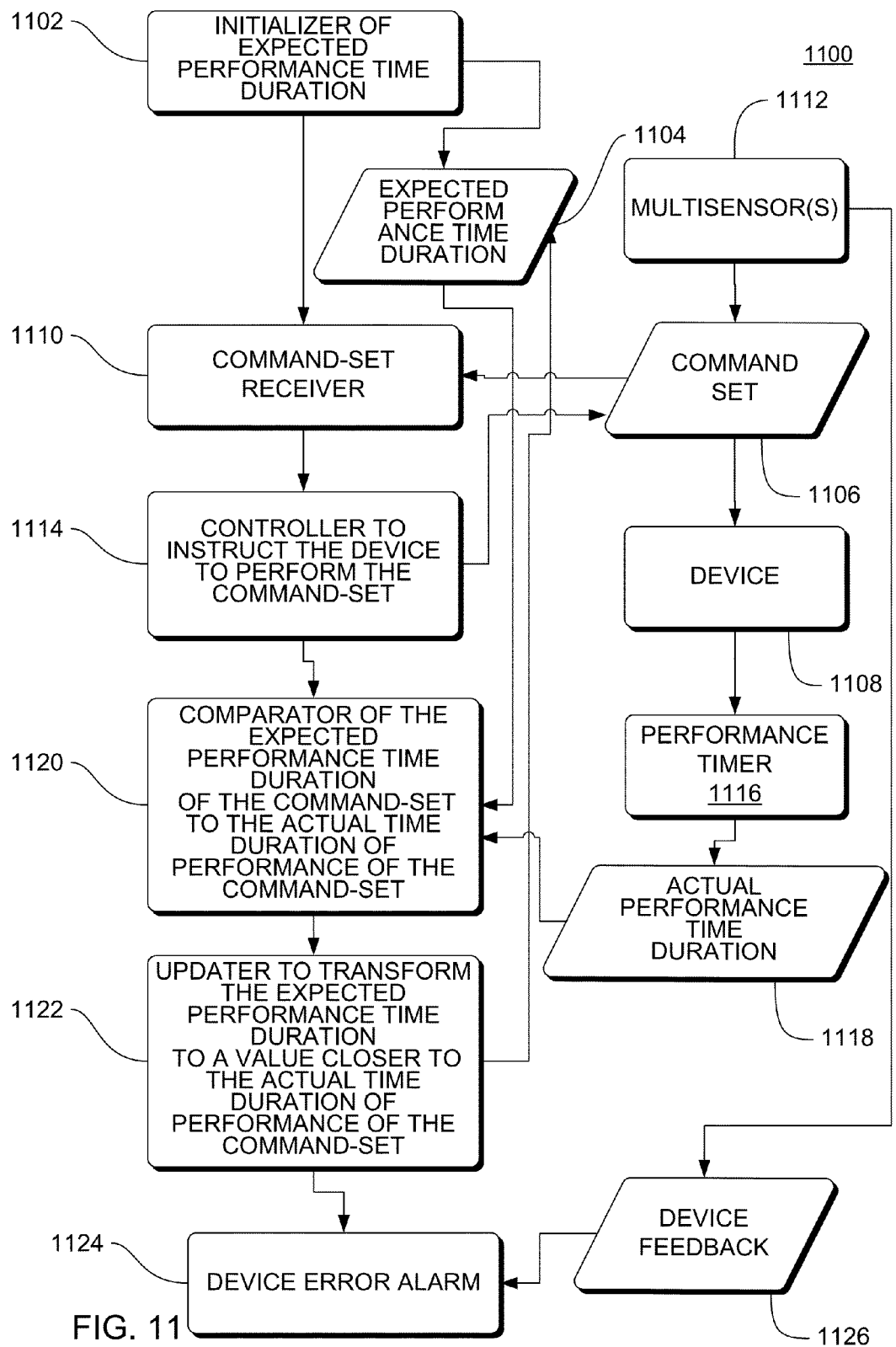
FIG. 11 is a block diagram of a machine to heuristically adapt to sensory input, according to an implementation.

FIG. 11 is a block diagram of a machine 1100 to heuristically adapt to sensory input, according to an implementation. In some implementations, machine 1100 includes an initializer 1102 of a value of an expected time duration of performance 1104 of a command-set 1106 by a device 1108. The source of the expected time duration of performance 1104 can be a human from which the expected time duration of performance 1104 is entered manually or the source of the expected time duration of performance 1104 can be a file that is accessed by the machine. In some implementations, the expected time duration 1104 is a value that is referenced or accessed over long periods of time, during which the machine 1100 can be expected to be shutdown and powered off at least one time, in which case the expected time duration of performance 1104 is stored in a nonvolatile storage medium that is operably coupled to or a part of the machine 1100 so that the expected time duration of performance 1104 is available after any instance of the machine 1100 being powered-off. For example, in some implementations, the machine 1100 is implemented as the voice-recognition apparatus 3300 in which the expected time duration of performance 1104 is stored in nonvolatile memory in the voice-recognition apparatus 3300.

In some implementations, the command-set is generated based on a combination sequence of at least one stimuli signal from the multisensor 1112, the stimuli signal being selected from a group of a unisensory stimuli signals and a multisensory stimuli signal.

Some implementations of machine 1100 also include a receiver 1110 of a representation of the command-set 1106. The representation of the command-set 1106 is received from one of a plurality of operable sensors 1112. In some implementations, the receiver 1110 receives a command-set 1106 from a plurality of human sensory devices (e.g. plurality of operable sensors 1112) by reading a sequence of 1 or more sensory stimulus and reading a sequence of 1 or more multisensory stimulus. In some implementations, the receiver 1110 receives a command-set 1106 from a plurality of human sensory devices (e.g. plurality of operable sensors 1112) by reading a sequence of 1 or more sensory action and reading a sequence of 1 or more multisensory action. In some implementations, the receiver 1110 receives a command-set 1106 from a plurality of human sensory devices (e.g. plurality of operable sensors 1112) by reading a sequence of 1 or more sensory input and reading a sequence of 1 or more multisensory input.

Some implementations of the machine 1100 also include a controller 1114 that is operable to instruct the device 1108 to perform the command-set 1106 in response to receipt of the representation of the command-set 1106.

Some implementations of the machine 1100 also include a real-time performance timer 1116 that records the duration of the actual performance time-1118 by the device 1108 of the command-set 1106.

Some implementations of the machine 1100 also include a real-time monitor 1116 that is operable to compare the expected time duration of performance 1104 of the command-set 1106 by the device 1108 to the actual time duration of performance 1118 of the command-set 1106 by the device 1108.

Some implementations of the machine 1100 also include an updater 1122 that is operable to transform the expected time duration 1104 to a value that is closer to the actual time duration of performance 1118 of the command-set 1106 by the device in response to completion of the command-set 1106 by the device 1108. In some implementations, the updater 1122 is operable to transform the expected time duration 1104 in reference to a frequency of the representation of the performance quality of the device 1108 and to update the expected time duration 1104 in reference to an expected frequency of the representation of the performance quality of the device 1108. For example, if the frequency of the representation of the performance quality of the device 1108 is greater than the expected frequency of the representation of the performance quality of the device 1108, the expected time duration 1104 is updated by a value that is more heavily weighted towards the actual performance time duration 1118.

Some implementations of the machine 1100 also include an alarm component 1124 that is operable to activate in response to receipt of a representation of feedback 1126 of the device 1108. The feedback 1126 is received through one of the plurality of operable sensors 1112. The feedback 1126 indicates that the device 1108 is in error after instruction to the device to perform the command-set 1106. The representation of feedback 1126 is received before completion of expected time duration 1104 of performance of the command-set 1106 by the device 1108.

In some implementations, the feedback 1126 is adjusted according for one or more factors. For example, in some implementations the feedback 1126 is adjusted heuristically in reference to evaluations received from a human (e.g. a "stop" command-set 1106 received from a human indicates the previous command-set 1106 was a mistake). For example, in some implementations the feedback 1126 is adjusted by weighting of the heuristic adjustment based on the expected frequency of particular forms of feedback 1126 and/or the length of time from the command-set 1106 to receipt of the feedback 1126 (e.g. actual duration of the command). For example, a particular command-set 1106 that is expected to be followed frequently or commonly by a "stop" command will be weighted lightly in regards to the heuristic score of feedback 1126. In another example, receiving a "Stop" command-set 1106 as feedback 1126 during the expected execution/performance duration of the previous command-set 1106 is highly weighted as negative feedback, the more immediately that a "Stop" command-set 1106 is received as feedback 1126 after the expected execution/performance duration of the previous command-set 1106 is lightly-weighted (e.g. less than 20%) or zero-weighted as negative feedback. For example, if a command-set is weighted lower and the expected duration of the command-set is 8 seconds, if 4 seconds into the expected duration, a "Stop" command-set is received, that "stop" command-set is heavily.

In some implementations the representation of the feedback 1126 of the device 1108 that is received through one of the plurality of operable sensors 1126 that indicates that the device 1108 is in error includes a representation of performance quality of the device 1108 that is received from a human through one of the plurality of operable sensors 1112 that further indicates that the device 1108 is in error. In some implementations, the representation of performance quality of the device 1108 that is received from the human through one of the plurality of operable sensors 1112 indicates that the device is in error includes a stop command-set. For example, the stop command-set is a verbal enunciation of "stop" by a human that will cease movement of the device 1108. In some implementations of the machine 1100, the machine also includes a receiver from a human of the value of the expected time duration 1104 of performance of the command-set by the device 1108; one example of the receiver being a conventional keyboard text entry facility and interface in the machine 1100.

Figure 12:
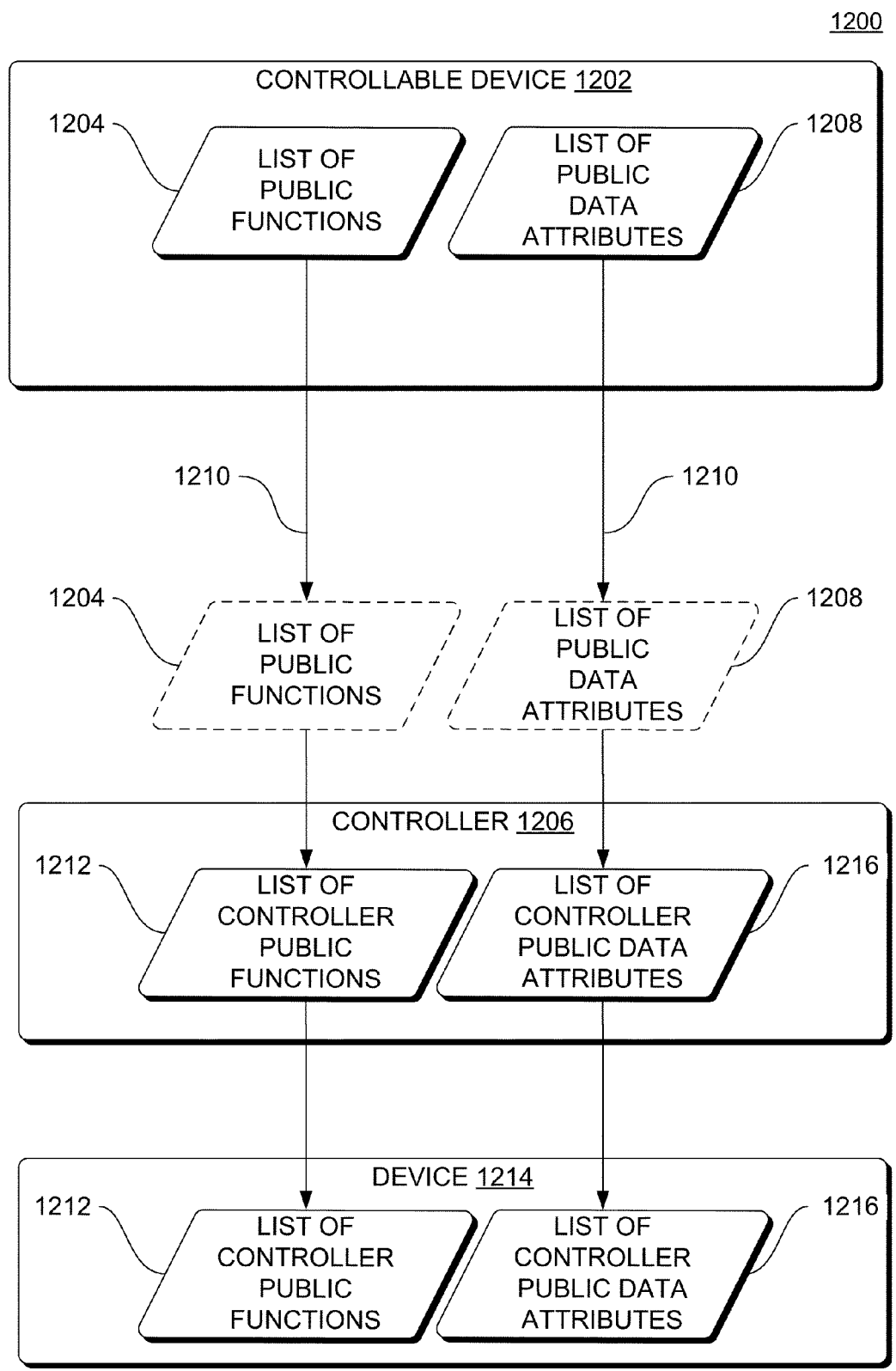
FIG. 12 is a block diagram of a hierarchical system of machines, according to an implementation.

FIG. 12 is a block diagram of a hierarchical system 1200 of machines, according to an implementation. In some implementations of system 1200, system 1200 includes at least one controllable device 1202 operable. In some implementation system 1200 includes more than one controllable device 1202. At least one of the controllable devices 1202 is operable to transmit a list of public functions 1204. The public functions 1204 are functions that can be performed by the controllable device 1204 and that are available to be controlled, invoked and/or monitored by another device other than the at least one controllable device 1202, such as controller 1206. The controllable device 1202 also includes a list of public data attributes 1208 of the at least one controllable device 1202. The public data attributes can include data items that are stored in the controllable device 1202 that that are available to be accessed, referenced, retrieved and/or updated by another device other than the at least one controllable device 1202, such as the controller 1206. One example of controller 1206 is microcontroller, processor or microprocessor 3302 in FIG. 33, such as a RSC 6502 microcontroller.

Some implementations of system 1200 also include the controller 1206. The controller 1206 is operable to control the at least one controllable device 1202. The controller 1206 can be operably coupled to the at least one controllable device 1202 through a communication link 1210, such as a wireless communication path. Some implementations of the controller 1206 are operable to receive the list of public functions 1204 of the at least one controllable device 1202. Some implementations of the controller 1206 are operable to receive the list of public data attributes 1208 of the at least one controllable device 1202.

Some implementations of the controller include a list of public functions 1212. The public functions 1212 are functions that can be performed by the controller 1206 and that are available to be controlled, invoked and/or monitored by another device other than the controller 1206, such as device 1214.

Some implementations of the public functions 1212 include aggregations of the public functions 1204 of one or more controllable devices 1202. In some further implementations, the public functions 1212 are aggregated by receiving public functions 1204 of one or more controllable devices 1202 and adding the list of public functions 1204 of the controllable device 1202 to the list of public functions 1212 of the controller 1206.

Some implementations of the controller 1206 also include a list of public data attributes 1216 of the controller 1206. The public data attributes 1216 can include data items that are stored in the controller 1206 that that are available to be accessed, referenced, retrieved and/or updated by another device other than the controller 1206, such as the device 1214.

Some implementations of the public data attributes 1216 include aggregations of the public data attributes 1208 of one or more controllable devices 1202. In some further implementations, the public data attributes 1216 are aggregated by receiving public data attributes 1208 of one or more controllable devices 1202 and adding the list of public data attributes 1208 of the controllable device 1202 to the list of public data attributes 1216 of the controller 1206.

In some implementations of the controller 1206, the controller 1206 is operable to transmit to another device (e.g. device 1214) other than the at least one controllable device, the internal list of public functions 1212 of the controller 1206 and the internal list of public data attributes 1216 of the controller 1206.

In some implementations device 1214 is a controllable controller that performs substantially the same functions in regards to aggregating public functions and public data attributes from other machines in the system 1200 that are lower in the hierarchy of devices and controllers and the controllable controller 1214 also is capable of publishing public functions and public data attributes to machines in the system 1200 that are higher in hierarchy of machines in the system 1200.

One implementation of system 1200 merely includes at least one controllable device 1202, at least one controllable controller 1214 that is operable to control the at least one controllable device 1202 and the system 1200 includes a controller 1206 that is operable to control the at least controllable controller 1214.

Figure 13:
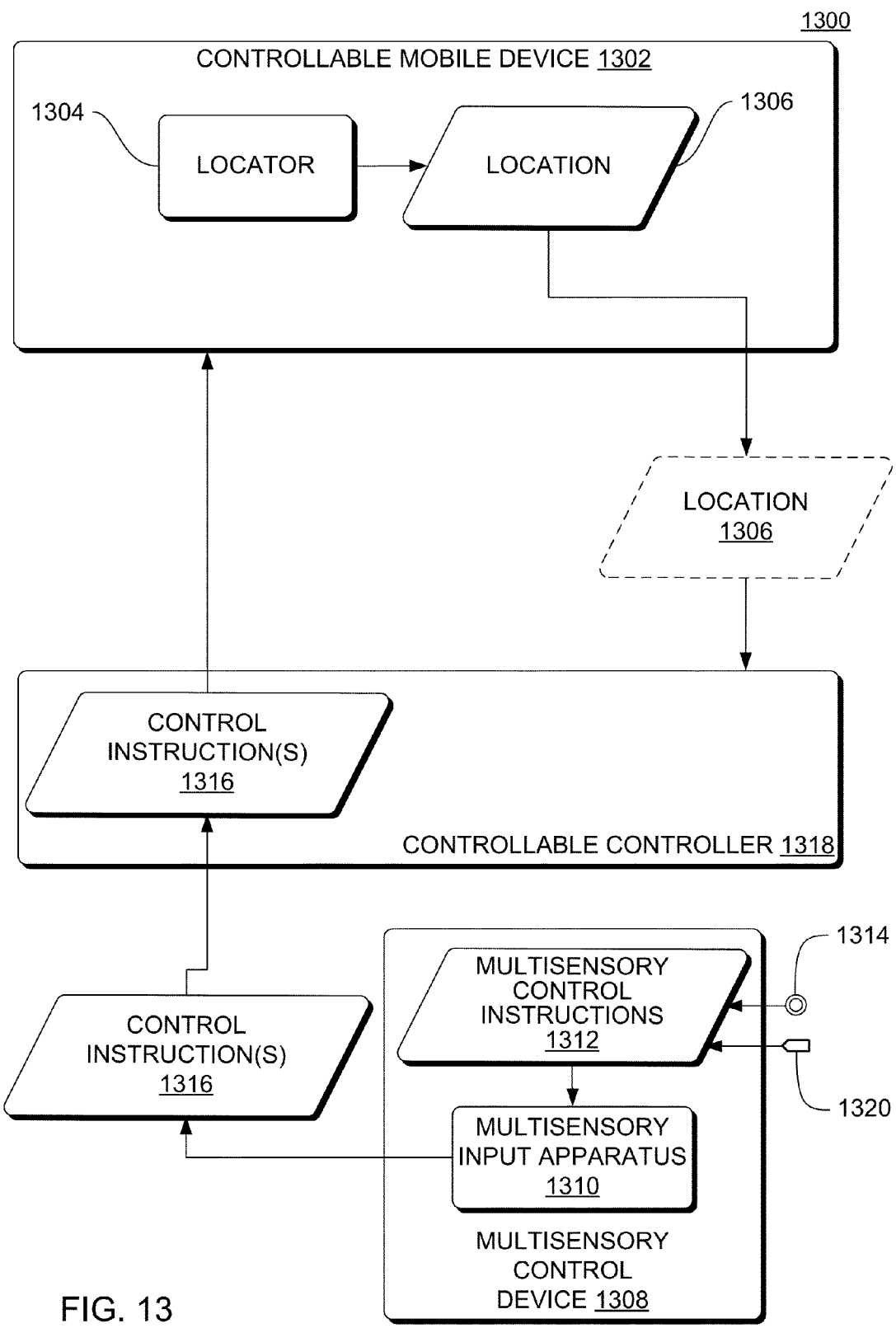
FIG. 13 is a block diagram of a mobile device control system, according to an implementation.

FIG. 13 is a block diagram of a mobile device control system 1300, according to an implementation. Some implementations of system 1300 include at least one controllable mobile device 1302. Examples of controllable mobile devices 1302 are powered wheelchairs and patient-lifting devices. Each controllable mobile device 1302 includes a component 1304 to identify a location 1306 of the at least one controllable mobile device 1302. Examples of the component 1304 include a global positioning system (GPS) receiver that is operable to receive GPS satellite signals from which a position of the controllable mobile device 1302 is triangulated.

Some implementations of mobile device control system 1300 include one or more multisensory control device(s) 1308. Each multisensory control device 1308 includes at least one multisensory input apparatus 1310 that is operable to transform multisensory control instructions 1312 (from a human through a sensor e.g. microphone 1314) to one or more control instruction(s).

Some implementations of the multisensory control device 1308 include a sensory input apparatus 1310 that is an electrodermal sensor 1320. The electrodermal sensor 1320 senses electrical resistance in skin surface of a subject. The multisensory input apparatus 1310 interprets the electrodermal resistance as a measure of stress in the subject and the multisensory control device 1308 generates control instruction(s) in accordance with the measure of stress. In some implementations, the multisensory control device 1308 generates control instruction(s) 1316 to stop or halt movement or operation of the controllable mobile device 1302 the device when the interpreted measure of stress exceeds a threshold and multisensory control device 1308 generates control instruction(s) 1316 to activate or enable movement of the controllable mobile device 1302 when the interpreted measure of stress is less than a threshold.

Some implementations of mobile device control system 1300 include one or more controllable controller(s) 1318 that are operable to control the at least one controllable mobile device 1302 in reference to the location 1306 of the at least one controllable mobile device 1302 and the control instructions(s) 1316.

Figure 14:
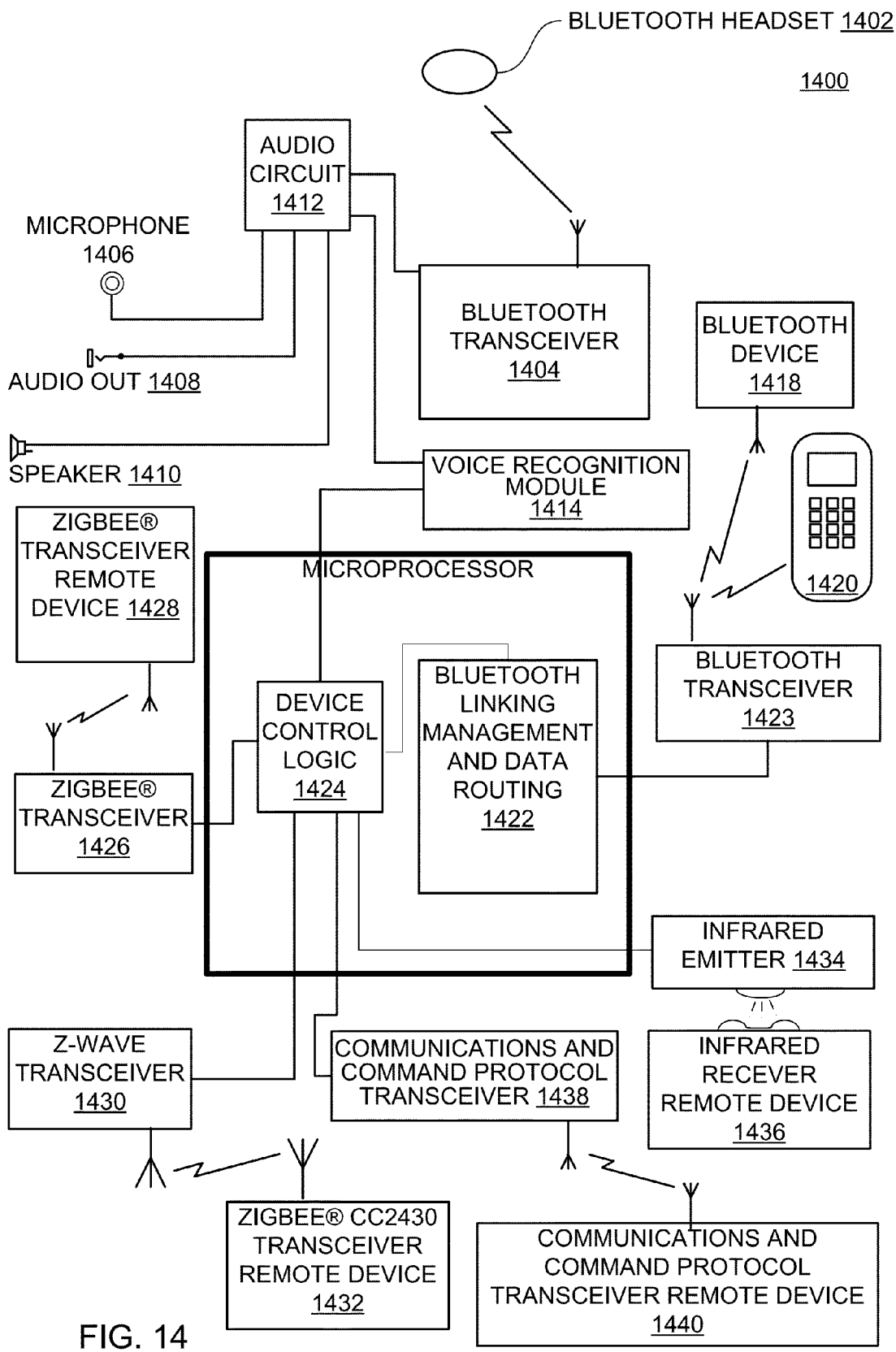
FIG. 14 is a block diagram of a voice recognition enabled universal wireless remote control, according to an implementation.

FIG. 14 is a block diagram of a voice recognition enabled universal wireless remote control 1400, according to an implementation. Bluetooth headset 1402 and Bluetooth transceiver 1404 facilitate verbal communications.

The user can send and receive verbal and audio communications either through the use of microphone 1406 and speaker 1410 or through the use of Bluetooth headset 1402 which communicates through Bluetooth transceiver 1404. Audio circuit 1412 communicates the sound information to the voice recognition module 1414. Voice recognition module 1414 monitors the input sound information with pattern recognition to identify trigger phrases. Once a trigger phrase is identified, the voice recognition module 1414 enters a command recognition mode for a pre-determined time, during which the voice recognition module 1414 monitors the input sound information with pattern recognition to identify commands. Once a command is recognized by the voice recognition module 1414, the control logic 1424 routes an appropriate ActionSet to a Bluetooth Linking Management and Data Routing Module 1422. If device control logic 1424 identifies the ActionSet being a Zigbee instruction set, the device control logic 1424 routes the predefined instruction set of the ActionSet to the Zigbee transceiver 1426 which in turn communicates the instruction set to Zigbee transceiver remote device 1428 which executes the appropriate action.

If device control logic 1424 identifies the ActionSet as being a Z-Wave instruction set, then the device control logic 1424 routes the predefined instructions set to the Z-Wave transceiver 1430 which in turn communicates the instructions set to Z-Wave transceiver remote device 1432 which executes the appropriate action.

If device control logic 1424 identifies the ActionSet being a Z-Wave instruction set, the device control logic 1424 routes the predefined instructions set to the Z-Wave transceiver 1428 which in turn communicates the instruction set to Z-Wave transceiver remote device 1430 which executes the appropriate action.

Some implementations of the Bluetooth Linking Management and Data Routing Module 1422 relates to radio transceiver devices for communicating voice and data using a predetermined protocol. Bluetooth transceivers such as Bluetooth distal transceiver are an example of such devices. Apparatus 1400 performs voice recognition to link and associate two or more devices in addition to routing voice and data communications.

In some implementations, the Bluetooth Linking Management and Data Routing Module 1422 provides audio and visual notification of previously associated devices. In some implementations, the Bluetooth Linking Management and Data Routing Module 1422 provides device audio and textual naming protocol. In some implementations, the Bluetooth Linking Management and Data Routing Module 1422 provides device sensing and acquisition. In some implementations, the Bluetooth Linking Management and Data Routing Module 1422 provides audio and visual notification of previously unassociated devices.

In some implementations, the Bluetooth Linking Management and Data Routing Module 1422 incorporates one or more Bluetooth compatible transceivers and a voice controlled Bluetooth device that links devices and routes data.

In some implementations, the Bluetooth Linking Management and Data Routing Module 1422 includes device connection specification that is a set of criteria and specifications that are use to manage the linking, data flow and interaction of Bluetooth devices. The device connection specification includes but is not limited to a device identity, a device audio name, a device text name, activity state, activity priority, interrupt threshold, start time and end time.

In some implementations, the Bluetooth Linking Management and Data Routing Module 1422 provides linking and associations between Bluetooth devices through voice commands.

In some implementations, the Bluetooth Linking Management and Data Routing Module 1422 provides different modes of notification, in which, the Bluetooth Linking Management and Data Routing Module 1422 is operable to track other Bluetooth devices available to the Bluetooth Linking Management and Data Routing Module 1422 and notify the user of any changes in status including but not limited to the introduction of a new device that is communicating in conformance to the Bluetooth protocol, the absence of a previously detected device, change in the signal strength of previously detected devices, activity on previously detected devices, request for linking, request for association.

A Bluetooth connection specification is a set of criteria and specifications that define linking, data flow and interaction of device that communicate in accordance to the Bluetooth protocol. The Bluetooth connection specification includes but is not limited to a device identity, a device audio name, a device text name, activity state, activity priority, interrupt threshold, start time and end time.

In some implementations, the Bluetooth Linking Management and Data Routing Module 1422 recognizes multiple variations and versions of the Bluetooth connection specification for any given Bluetooth device.

In some implementations, the Bluetooth Linking Management and Data Routing Module 1422 provides a facility for a user to access to create criteria sets for notification for individual devices and groups of devices. For example, a Bluetooth device named "headset" incorporates a voice controlled Bluetooth device that links to the Bluetooth Linking Management and Data Routing Module 1422 through a Bluetooth transceiver 1423. In addition, the user can create a criteria set named "Cell phone one daytime home" for one or more remote Bluetooth devices, such as Bluetooth-capable device 1418 or Bluetooth-capable cell phone 1420, each of which can include multiple remote voice command device activity states for each of which can have its own interrupt threshold, wherein the user can define device activity state's with specific interrupt threshold that can be associated with particular devices and activities. Activities can include notification of the introduction of the availability of one or more Bluetooth devices 1418 or 1420 by and audio notification of "cell phone two is available." Activities can also include notification of the absence of a previously detected Bluetooth device 1418 or 1420 by an audio notification of "cell phone two is no longer available." Activities can also include notification of a weak signal strength in the Bluetooth-capable cell phone 1420 by an audio notification of "cell phone one signal is weak."

If device control logic 1424 identifies the ActionSet as being an Infrared instruction set that the device control logic 1424 routes the predefined instructions set to the Infrared Emitter 1434 which in turn communicates the instructions set to Infrared Emitter remote device 1436 which executes the appropriate infrared action.

If device control logic 1424 identifies the ActionSet as being a Communications and Command Protocol instruction set that the device control logic 1424 routes the predefined instructions set to a Communications and Command Protocol transceiver 1438 which in turn communicates the instructions set a Communications and Command Protocol remote device 1440 which executes the appropriate Communications and Command Protocol action.

Figure 15:
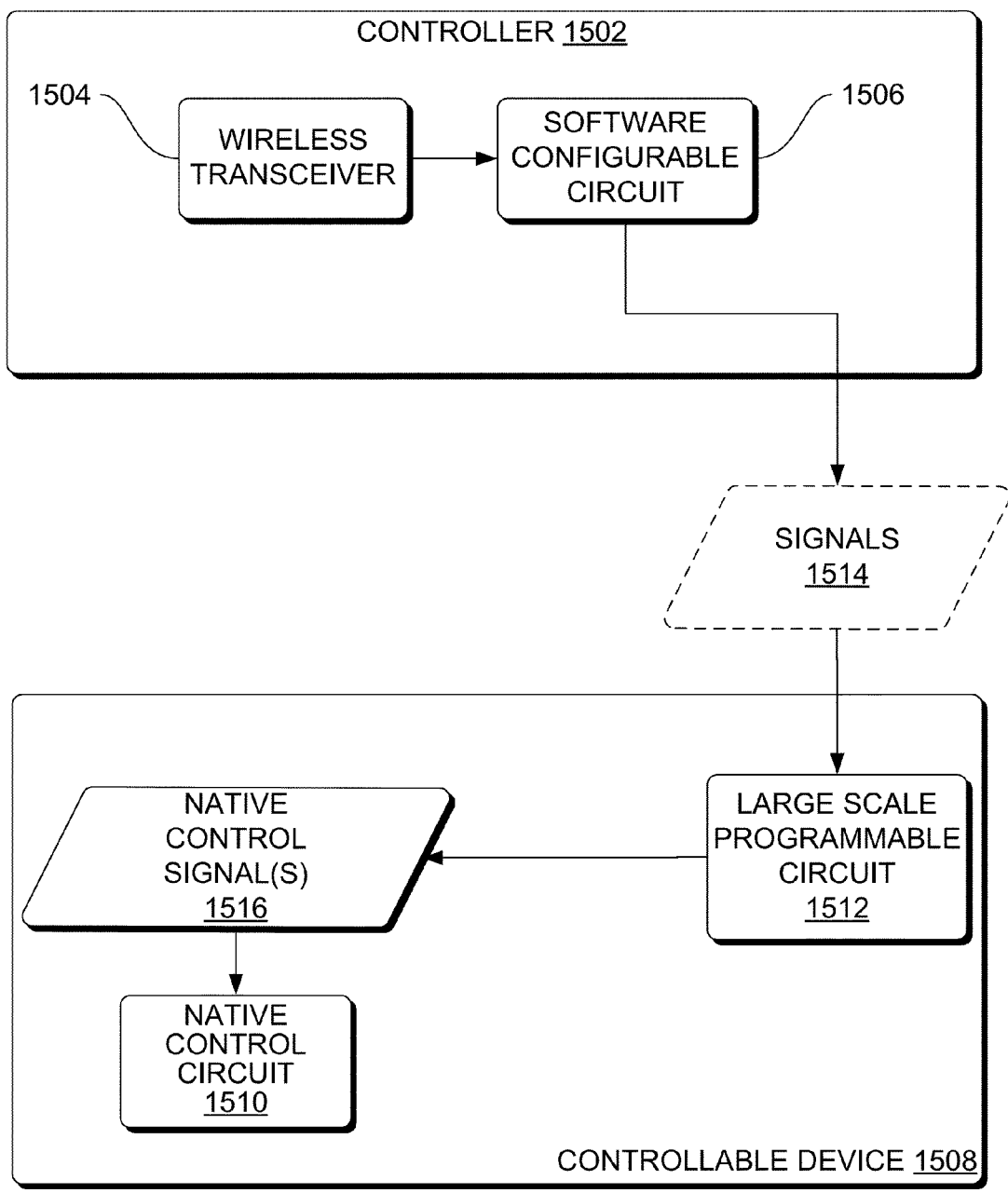
FIG. 15 is a block diagram of an apparatus, according to an implementation.

FIG. 15 is a block diagram of an apparatus 1500, according to an implementation. Apparatus 1500 includes a controller 1502. The controller 1502 includes a wireless transceiver component 1504 and a software configurable circuit 1506 having multisensory recognition capability. In some implementations, the software configurable circuit 1506 further comprises a field-programmable gate array (FPGA).

Apparatus 1500 also includes a controllable device 1508 that includes a native control circuit 1510 and a large scale programmable circuit 1512 that is operable to receive signals 1514 from the controller 1502 and is operable to transform the signals 1514 from the controller into native control signals 1516 of the controllable device 1508, and the large scale programmable circuit 1512 is operable to transmit the native control signals 1516 to the native control circuit 1510. In some implementations, the large scale programmable circuit 1512 is a very-large-scale integrated (VLSI) circuit that includes power relays.

Figure 16:
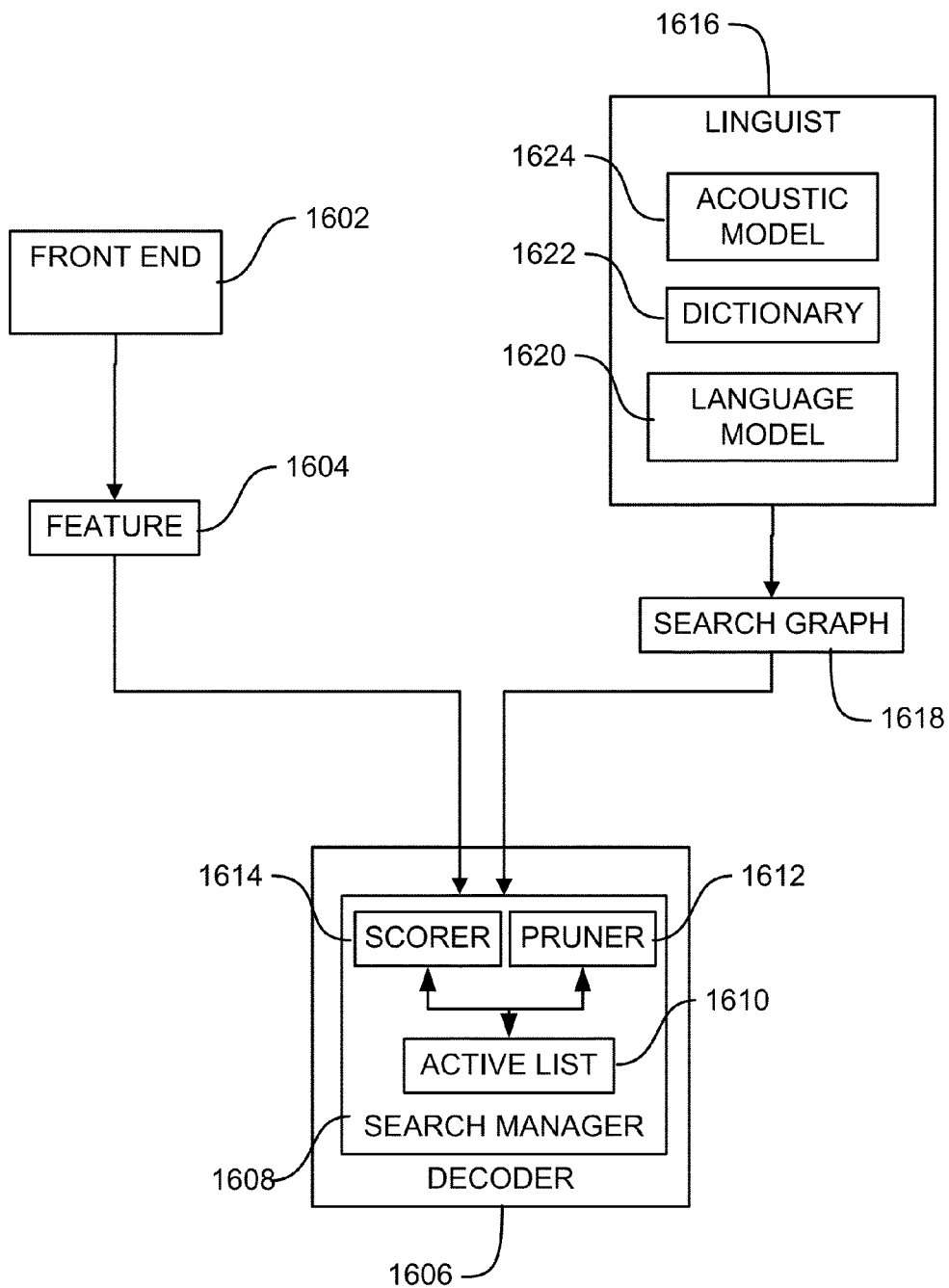
FIG. 16 is a block diagram of a voice-recognition engine, according to an implementation.

FIG. 16 is a block diagram of a voice-recognition engine 1600, according to an implementation. The voice-recognition engine 1600 includes a frontend component 1602 parameterizes an input signal (e.g., audio) into a sequence of output features 1604. The frontend component 1602 includes one or more parallel chains of replaceable communicating signal processing modules called data-processors (not shown). Supporting multiple chains of data-processors of the front-end 1602 permits simultaneous computation of different types of parameters from the same or different input signals. The simultaneous computation enables simultaneous decoding using different parameter types, and even parameter types derived from non-speech signals such as video.

Each data-processor in the frontend component 1602 provides an input and an output that can be connected to another data-processor of the front-end 1602, permitting arbitrarily long sequences of chains of data-processors. The inputs and outputs of each data-processor of the front-end 1602 are generic data objects that encapsulate processed input data as well as markers that indicate data classification events such as end-point detection. The last data-processor of the front-end 1602 in each chain produces a data object composed of parameterized signals (e.g. features 1604) to be used by a decoder component 1606.

The voice-recognition engine 1600 produces parallel sequences of features 1602. The voice-recognition engine 1600 allows for an arbitrary number of parallel streams.

Communication between blocks follows a pull design. With a pull design, a data-processor of the front-end 1602 requests input from an earlier module only when needed, as opposed to the more conventional push design, where a module propagates its output to the succeeding module as soon as the output is generated. This pull design enables the processors to perform buffering, allowing consumers to look forwards or backwards in time.

The ability to look forwards or backwards in time not only permits the decoder component 1606 to perform frame-synchronous Viterbi searches, but also allows the decoder component 1606 to perform other types of searches such as depth-first and A*.

Within the generic frontend component 1602 framework, the voice-recognition engine 1600 provides a suite of data-processors of the front-end 1602 that implement conventional signal processing techniques. These implementations include support for the following: reading from a variety of input formats for batch mode operation, reading from the system audio input device for live mode operation, preemphasis, windowing with a raised cosine transform (e.g., Hamming and Hanning windows), discrete fourier transform (EFT), mel frequency filtering, bark frequency warping, discrete cosine transform (DCT), linear predictive encoding (LPC), end pointing, cepstral mean normalization (CMN), mel-cepstra frequency coefficient extraction (MFCC), and perceptual linear prediction coefficient extraction (PLP).

The voice-recognition engine 1600 includes a search-manager component 1608 generates active-lists 1610 from currently active tokens in the search trellis by pruning using a pluggable pruner component 1612. A pruner component 1612 can perform relative and/or absolute beam pruning. The implementation of the pruner component 1612 is greatly simplified by the garbage collector of a Java platform. With garbage collection, the pruner component 1612 prunes a complete path by merely removing the terminal token of the path from the activelist 1610. The act of removing the terminal token identifies the token and any unshared tokens for that path as unused, allowing the garbage collector to reclaim the associated memory.

The search-manager component 1608 sub-framework also includes a scorer component 1614, a pluggable state probability estimation module that provides state output density values on demand. When the Search-manager component 1608 requests a score for a given state at a given time, the scorer component 1614 accesses the feature vector for that time and performs the mathematical operations to compute the score. In the case of parallel decoding using parallel acoustic models, the scorer component 1614 matches the acoustic model set to be used against the feature type.

The scorer component 1614 retains all information pertaining to the state output densities. Thus, the search-manager component 1608 need not store data indicating whether the scoring is done with continuous, semi-continuous or discrete hidden Markov models (HMMs). Furthermore, the probability density function of each HMM state is isolated in the same fashion. Any heuristic algorithms incorporated into the scoring procedure for speeding the scorer component 1614 can also be performed locally within the scorer component 1614. In addition, the scorer component 1614 can take advantage of multiple processors if they are available.

The voice-recognition engine 1600 includes a linguist component 1616 generates a search-graph 1618 that is used by the decoder component 1606 during the search, while at the same time hiding the complexities involved in generating a graph. The linguist component 1616 is a pluggable module, allowing people to dynamically configure the system with different linguist components 1616.

A typical linguist component 1616 constructs the search-graph 1618 using the language structure as represented by a given language-model 1620 and the topological structure of the acoustic-model 1624 (HMMs for the basic sound units used by the system). The linguist component 1616 may also use a dictionary 1622 (typically a pronunciation lexicon) to map words from the language-model 1620 into sequences of acoustic-model 1624 elements. When generating the search-graph 1618, the linguist component 1616 may also incorporate sub-word units with contexts of arbitrary length.

The graph is a directed graph in which each node, called a search state, represents either an emitting or a non-emitting state. Emitting states can be scored against incoming acoustic features while non-emitting states are generally used to represent higher-level linguistic constructs such as words and phonemes that are not directly scored against the incoming features 1602. The arcs between states represent the possible state transitions, each of which has a probability representing the likelihood of transitioning along the arc.

By allowing different implementations of the linguist component 1616 to be plugged in at runtime, the voice-recognition engine 1600 permits individuals to provide different configurations for different system and recognition requirements. For instance, a simple numerical digits recognition application might use a simple linguist component 1616 that keeps the search space entirely in memory. On the other hand, a dictation application with a 100K word vocabulary might use a sophisticated linguist component 1616 that keeps only a small portion of the potential search space in memory at a time.

The linguist component 1616 itself includes of three pluggable components: a language-model 1620, a dictionary 1622, and an acoustic-model 1624, which are described in the following sections.

The language-model 1620 module of the linguist component 1616 provides word-level language structure, which can be represented by any number of pluggable implementations. These implementations typically fall into one of two categories: graph-driven grammars and stochastic N-Gram models. The graph-driven grammar represents a directed word graph where each node represents a single word and each arc represents the probability of a word transition taking place. The stochastic N-Gram models provide probabilities for words given the observation of the previous n−1 words.

The dictionary 1622 provides pronunciations for words found in the language-model 1620. The pronunciations break words into sequences of sub-word units found in the acoustic-model 1624. The dictionary 1622 interface also supports the classification of words and allows for a single word to be in multiple classes. The various implementations optimize for usage patterns based on the size of the active vocabulary. For example, one implementation will load the entire vocabulary at system initialization time, whereas another implementation will only obtain pronunciations on demand.

The acoustic-model 1624 module provides a mapping between a unit of speech and an HMM that can be scored against incoming features 1602 provided by the frontend component 1602. As with other systems, the mapping may also take contextual and word position information into account. For example, in the case of triphones, the context represents the single phonemes to the left and right of the given phoneme, and the word position represents whether the triphone is at the beginning, middle, or end of a word (or is a word itself). The contextual definition is not fixed by the voice-recognition engine 1600, allowing for the definition of the acoustic-model 1624 that contain allophones as well as the acoustic-model 1624 whose contexts do not need to be adjacent to the unit.

Typically, the linguist component 1616 breaks each word in the active vocabulary into a sequence of context-dependent sub-word units. The linguist component 1616 then passes the units and their contexts to the acoustic-model 1624, retrieving the HMM graphs associated with those units. The linguist component 1616 then uses these HMM graphs in conjunction with the language-model 1620 construct the search-graph 1618.

The HMM is a directed graph of objects. In this graph, each node corresponds to an HMM state and each arc represents the probability of transitioning from one state to another in the HMM. By representing the HMM as a directed graph of objects instead of a fixed structure, an implementation of the acoustic-model 1624 can easily supply HMMs with different topologies. For example, the acoustic-model 1624 interfaces do not restrict the HMMs in terms of the number of states, the number or transitions out of any state, or the direction of a transition (forward or backward). Furthermore, the voice-recognition engine 1600 allows the number of states in an HMM to vary from one unit to another in the same acoustic-model 1624.

Each HMM state is capable of producing a score from an observed feature. The actual code for computing the score is done by the HMM state itself, thus hiding its implementation from the rest of the system, even permitting differing probability density functions to be used per HMM state. The acoustic-model 1624 also allows sharing of various components at all levels. That is, the components that make up a particular HMM state such as Gaussian mixtures, transition matrices, and mixture weights can be shared by any of the HMM states to a very fine degree.

Individuals can configure the voice-recognition engine 1600 with different implementations of the acoustic-model 1624 based upon their needs. The voice-recognition engine 1600 provides a single acoustic-model 1624 implementation that is capable of loading and using acoustic models.

Even though the linguist component 1616 may be implemented in very different ways and the topologies of the search spaces generated by these, the linguist component 1616 can vary greatly, the search spaces are all represented as a search-graph 1618. The search-graph 1618 is the primary data structure used during the decoding process.

Method Implementations

In the previous section, apparatus of the operation of an implementation was described. In this section, the particular methods performed by a processor of such an implementation are described by reference to a series of flowcharts.

Figure 46:
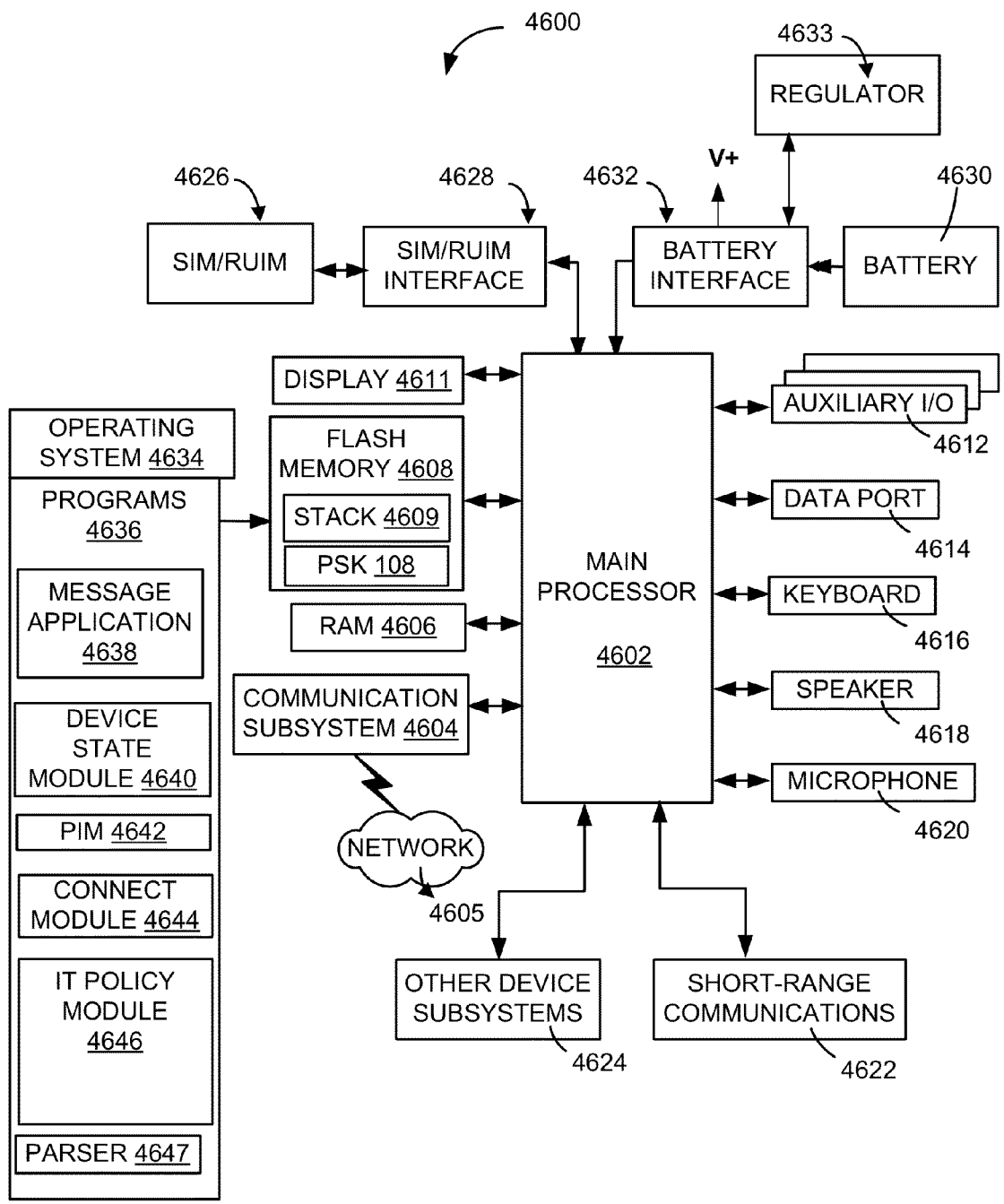
FIG. 46 is a block diagram of a mobile device, according to an implementation.
Figure 47:
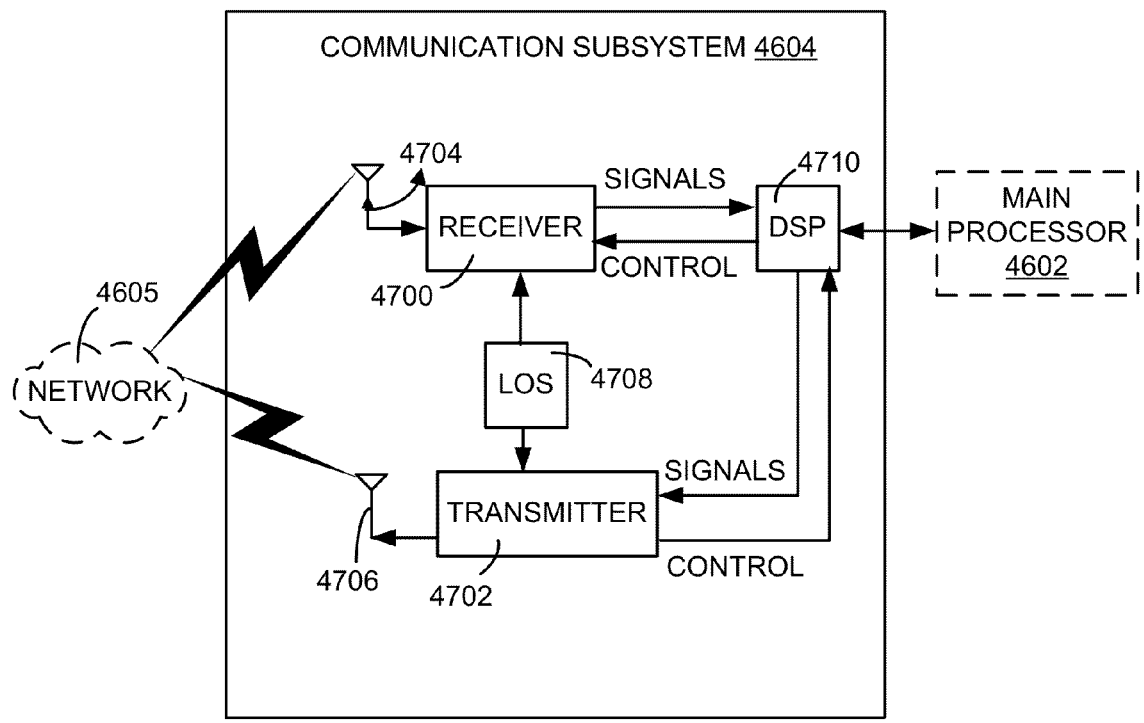
FIG. 47 is a block diagram of a communication subsystem component of the mobile device of FIG. 46, according to an implementation.

In some implementations, methods 1700-3000 are implemented as a sequence of instructions which, when executed by a processor, such as processor unit 4704 in FIG. 47, microcontroller 3302 in FIG. 33 or processor 106 in FIG. 1 and FIG. 2, cause the processor to perform the respective method. In other implementations, methods 1700-3000 are implemented as a computer-accessible or a computer-usable medium having executable instructions capable of directing a processor, such as microprocess for in FIG. 14, microcontroller 3302 in FIGS. 33 and 3402 in FIG. 34 or main processor 4602 in FIG. 46, to perform the respective method. In varying implementations, the medium is a magnetic medium, an electronic medium, or an optical medium.

Figure 17:
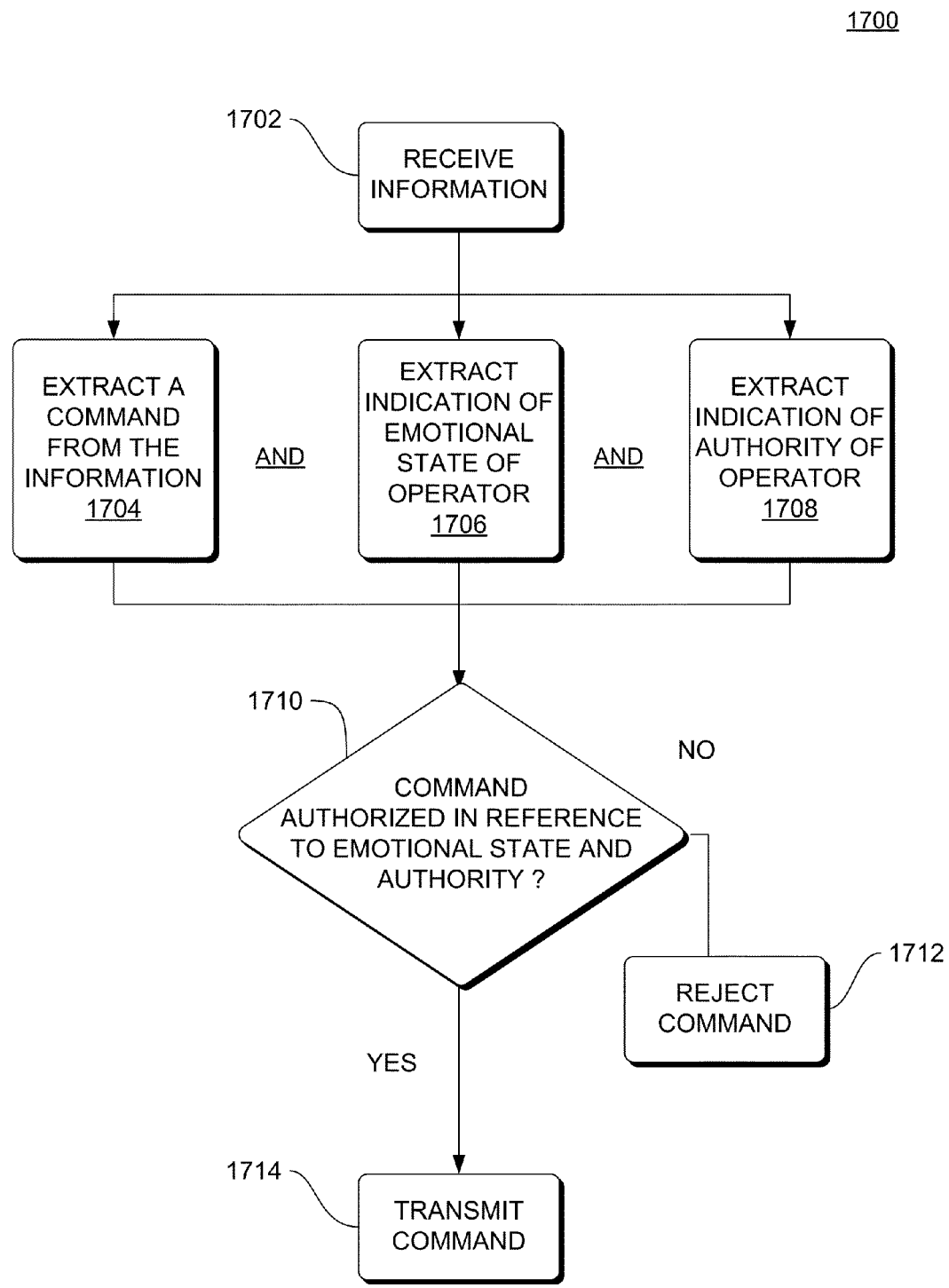
FIG. 17 is a flowchart of a method to control a patient-lifting-device, according to an implementation.
Figure 18:
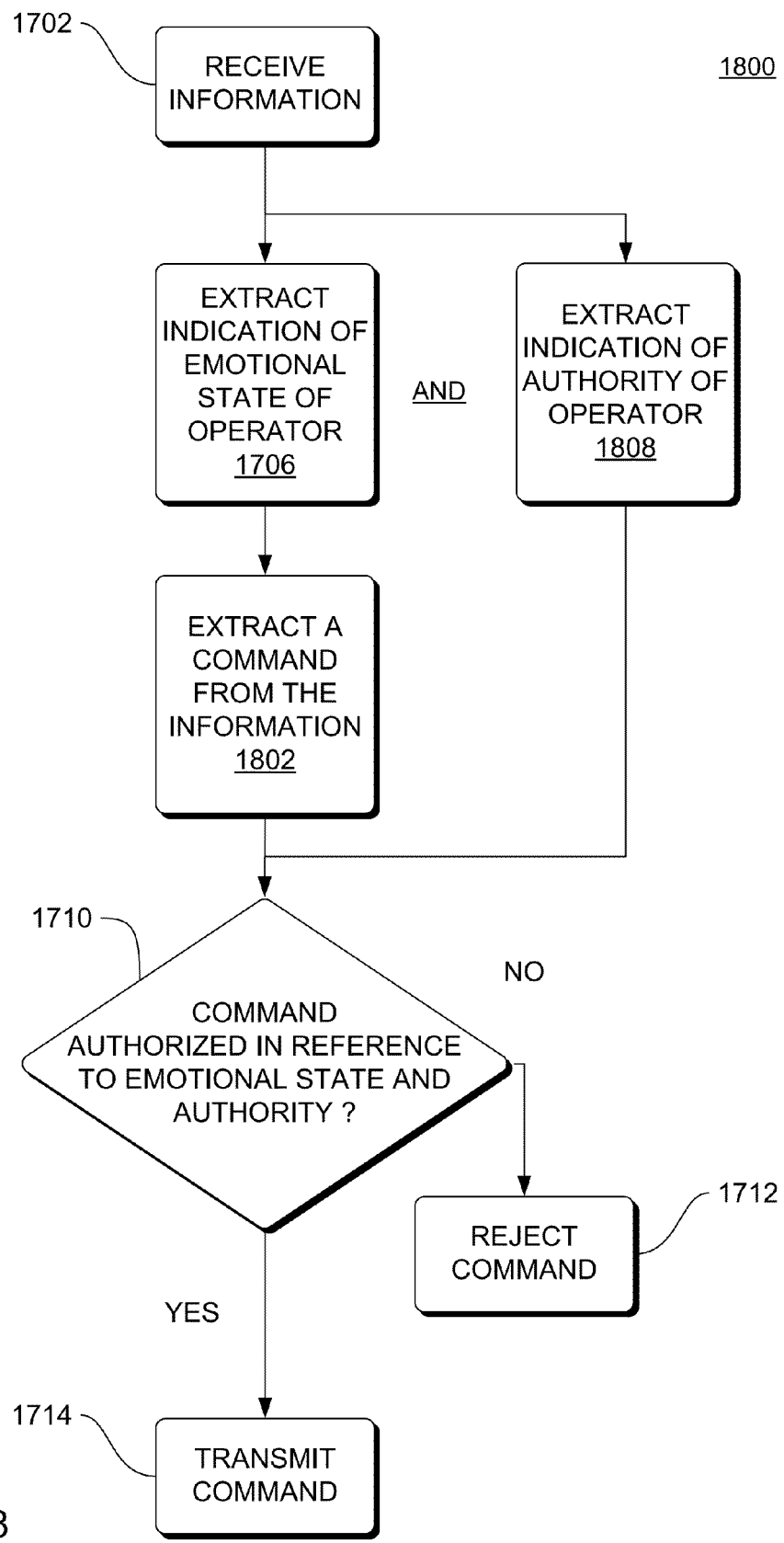
FIG. 18 is a flowchart of a method to control a patient-lifting-device, according to an implementation.

FIG. 17 is a flowchart of a method 1700 to control a patient-lifting-device, according to an implementation. Method 1700 receives information from a human and generates a command from the human information, in reference to authority of the human and the state of the mind of the human. Method 1700 generates command(s) that are suitable to be processed by a processor in control of a patient-lifting-device. In some implementations, method 1700 is performed by the command interface unit 102 and FIG. 1 and FIG. 2.

Method 1700 includes receiving 1702 information from any one of a number of different communication devices. FIG. 6 describes some implementations of communication devices. Method 1700 includes processing the information by analyzing the information and extracting 1704 a command from the information. Examples of the command include "lift up" "move up" "lower down" "move down" "move forward" "forward" "move backward "reverse" "stop" "goto sleep" "sleep" "activate" and "help." Method 1700 includes processing the information by analyzing and extracting 1706 from the information indicators of the emotional state of the operator, indicators of the competency of the operator, and/or indicators of the state-of-mind of the operator.

Method 1700 includes processing the information by analyzing the information and extracting 1708 from the information an indicator of the authority of the operator. In some implementations, extracting an indication of authority of the operator includes identifying the operator. For example, where the information 1702 is audio information from a human speaker, the identity of the human speaker is determined and the authority of that speaker is then determined. In some implementations, the speech pattern of the human speaker is compared to a database of known humans. The database is created prior to the performance of method 1700 from recorded speech sample recordings of humans who are authorized to enter the healthcare facility, such a healthcare providers, non-professional employees of the healthcare facility, patients, and friends, relatives and/or coworkers of the patient. Each human whose speech sample is recorded in the database is associated with a particular authority. An example of an authority is "full authority" in which the human is authorized to exercise or command all functions of the lift. Another example of an authority is "no authority in which the human is not authorized to exercise or command any function of the lift. In method 1700, the database is accessed and a comparison of the information 1702 to the speech samples in the database is performed. When the comparing determines the identity of the human speaker, the authority of the identified human is accessed and used as the indicator of authority of the operator.

In method 1700, the command, the state-of-mind and the indicator of authority of the operator is analyzed 1710 to an authority database to determine whether or not the command is authorized by the authority of the operator in consideration of the emotional state of the operator. If the command is not authorized by the authority and emotional state of the operator, the command is rejected 1712. In some implementations, rejecting 1712 the command can include transmitting a notice of an attempted unauthorized command to supervisory personnel or law enforcement agency. If the command is determined to be authorized, the command is transmitted 1714 to the processor (e.g. 106 in FIG. 1) and the command 1712 is performed by the lift. In some implementations, a log or journal of all extracted commands in action 1704 and the determination 1710 of the authority of the extracted commands is stored.

Method 1800 includes receiving 1702 information from any one of a number of different communication devices. FIG. 6 describes some implementations of communication devices.

Method 1800 includes processing the information by analyzing the information and extracting 1708 from the information an indicator of the authority of the operator. In some implementations, extracting an indication of authority of the operator includes identifying the operator. For example, where the information 1702 is audio information from a human speaker, the identity of the human speaker is determined and the authority of that speaker is then determined. In some implementations, the speech pattern of the human speaker is compared to a database of known humans. In method 1800, the database is accessed and a comparison of the information 1702 to the speech samples in the database is performed. When the comparing determines the identity of the human speaker, the authority of the identified human is accessed and used as the indicator of authority of the operator.

Method 1800 includes processing the information by analyzing the information and extracting 1802 a command from the information. Examples of the command include "lift up" "move up" "lower down" "move down" "move forward" "forward" "move backward "reverse" "stop" "goto sleep" "sleep" "activate" and "help." Method 1800 includes processing the information by analyzing and extracting 1706 from the information indicators of the emotional state of the operator, indicators of the competency of the operator, and/or indicators of the state-of-mind of the operator.

In method 1800, the command, the state-of-mind and the indicator of authority of the operator is analyzed 1710 to an authority database to determine whether or not the command is authorized by the authority of the operator in consideration of the emotional state of the operator. If the command is not authorized by the authority and emotional state of the operator, the command is rejected 1712. In some implementations, rejecting 1712 the command can include transmitting a notice of an attempted unauthorized command to supervisory personnel or law enforcement agency. If the command is determined to be authorized, the command is transmitted 1714 to the processor (e.g. 106 in FIG. 1) and the command 1712 is performed by the lift. In some implementations, a log or journal of all extracted commands in action 1802 and the determination 1710 of the authority of the extracted commands is stored.

FIG. 19 is a flowchart of a method 1900 to control a patient-lifting-device, according to an implementation involving trigger words. Some implementations of method 1900 include receiving audio, at block 1902. A determination is made as to whether or not the volume of the audio is below a threshold for a predetermined amount of time, at block 1904. The audio level being below the threshold for predetermined amount of time is interpreted to be the end of a command sequence from the operator. If the audio level is determined to be not below the threshold for the predetermined amount of time at block 1904, method 1900 continues with receiving audio at block 1902. If the audio level is equal to and/or greater than the audio volume threshold for the predetermined amount of time at block 1904 method 1900 continues by extracting a command from the audio, at block 1906. In some implementations method 1900 also includes determining whether or not the command is a word or phrase in a trigger override word set, at block 1908. Examples of a trigger override word set include the words "stop," "wait" and "help." If the command is determined to be in the trigger override word set at block 1908 then the command is performed at block 1910, and/or movement of the patient-lifting-device is ceased. If the command is not determined to be in the trigger override word set at block 1908 then a determination is made as to whether or not the command is in a trigger phrase word set, at block 1912. The trigger phrase word set includes commands such that indicate the intention by the operator to provide a functional command to the patient-lifting-device. Examples of a trigger phrase word set include "molift command," "lift command," and "attention." If the command is determined to not be in the trigger phrase word set at block 1912, method 1900 continues with receiving audio at block 1902. If the command is determined to be in the trigger phrase word set at block 1912, the method continues by receiving a next command, at block 1914, and then performing the next command, at block 1916. Examples of commands that are performed at block 1916 include "lower down," "move down," "move forward," "forward," "move backward," "reverse," "goto sleep," "sleep," "faster," "slower," "left," "right," "up," "down," "forward," and "backward" or other commands to move the patient lifting device in a particular direction and/or any particular speed.

One example of the predetermined amount of time in method 1900 and method 2000 is two (2) seconds, however other implementations other amounts of time are implemented. One example of the threshold volume of audio in method 1900 is 70 dB, however other implementations of other threshold levels of audio volume are implemented. In some implementations the amount of predetermined time and/or the threshold level of audio volume can be modified through a user configuration interface.

FIG. 20 is a flowchart of a method 2000 to control a patient-lifting-device, according to an implementation involving trigger override command set words. Some implementations of method 2000 include receiving audio, at block 1902. A determination is made as to whether or not the volume of the audio is above a threshold for at least a predetermined amount of time, at block 1904. The audio level being above the threshold for predetermined amount of time is interpreted to indicate a possible emergency situation which might be dangerous to operate the patient-lifting apparatus. One example of the threshold volume of audio in method 1500 is 90 dB, however other implementations of other threshold levels of audio volume are implemented. If the audio level is determined to be not above the threshold for the predetermined amount of time at block 1902, in which method 2000 continues with receiving audio at block 1902. If the audio level is greater than the audio volume threshold for at least the predetermined amount of time at block 1904, method 2000 continues by performing a safety procedure at block 1905. Examples of the safety procedure are stopping movement of the patient-lifting-device, reversing movement, and reversing a previous action. After performing the safety procedure at block 1905, method 2000 continues with receiving audio at block 1902. In some implementations the amount of predetermined time and/or the threshold level of audio volume can be modified through a user configuration interface.

Figure 21:
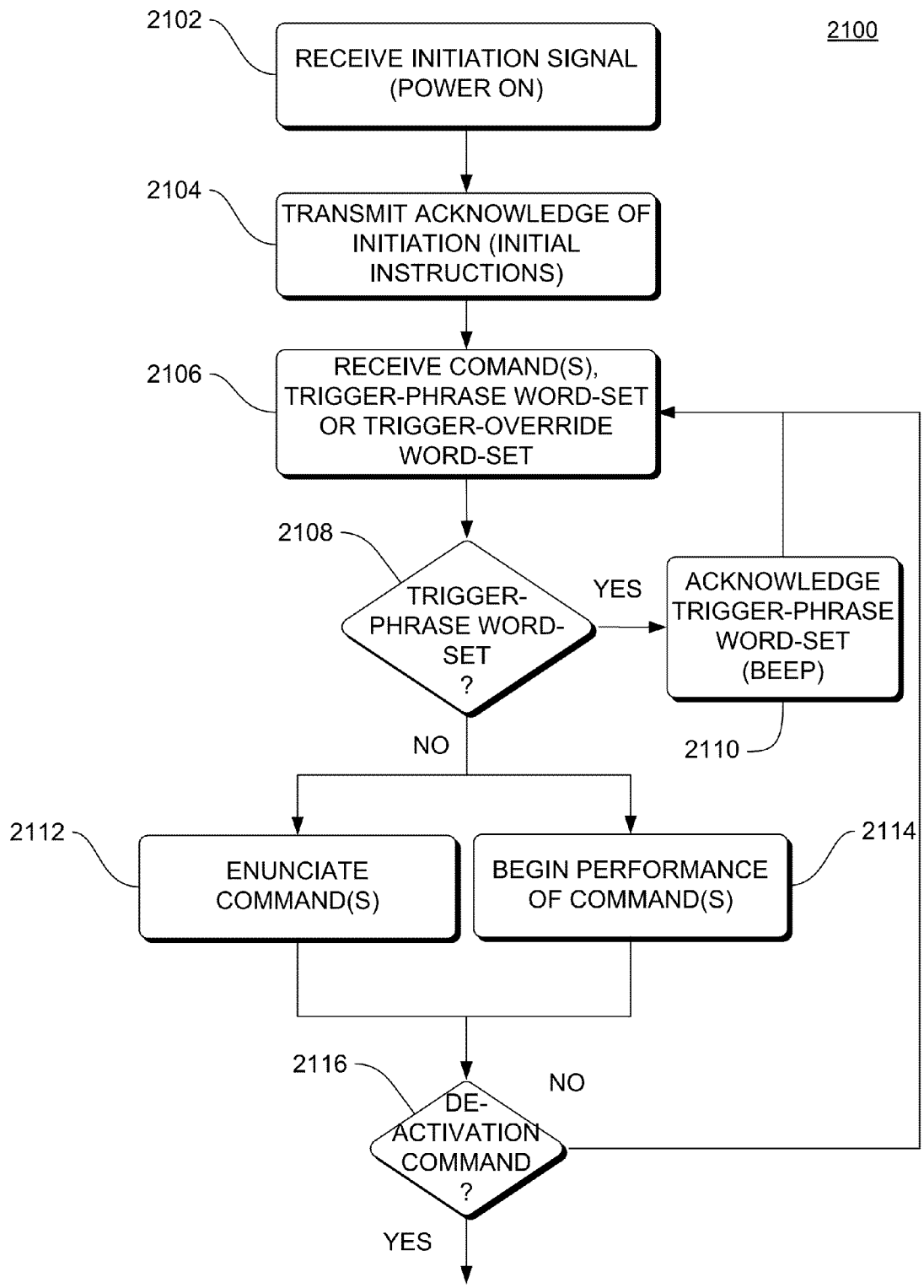
FIG. 21 is a flowchart of a method to control a patient-lifting-device, according to an implementation involving trigger words.

FIG. 21 is a flowchart of a method 2100 to control a patient-lifting-device, according to an implementation involving disruptive audio volume. Some implementations of method 2100 include receiving an initiation signal at block 2102 and then transmitting an acknowledgment of the initiation signal at block 2104. One example of an initiation signal is an indication of the processor or the patient-lifting-device being powered on. One example of an acknowledgment of the initiation is an audio enunciation of instructions on how to operate the system. In some implementations the instructions include a recitation of voice command instructions.

Method 2100 includes receiving a command, a trigger-phrase word-set or trigger-override word-set, at block 2106. In some implementations, trigger-phrase word-set or trigger-override word-set is a recognition of verbiage from an audio signal. The trigger-phrase word-set or trigger-override word-set are described in conjunction with FIG. 19. The trigger-phrase word-set or trigger-override word-set is evaluated or compared to determine if the trigger-phrase word-set or trigger-override word-set is trigger-phrase word-set, at block 2108. If the trigger-phrase word-set or trigger-override word-set is a trigger-phrase word-set, then an acknowledgment of the trigger-phrase word-set presented and the local environment, at block 2110. For example if the trigger-phrase word-set "Molift™ command" is received at block 2106, then a "beep" sound is enunciated. The beep sound provides a cue to the speaker of the trigger-phrase word-set that the system understands that the user has enunciated a trigger-phrase word-set and that the speaker intends to enunciate a command for performance by the system. The command is substantially similar to the command-set 1106 of FIG. 11.

If the comparison at block 2108 determines that the trigger-phrase word-set or trigger-override word-set is not a trigger-phrase word-set, in which case the trigger-phrase word-set or trigger-override word-set is a trigger-override word-set or a command, then an acknowledgment of the command or trigger-override word-set is presented to the local environment, at block 2112. For example, the command or the trigger-override word-set is enunciated by a speech generation module. The presentation of the command or the trigger-override word-set at block 2112 provides an acknowledgment of the function that is to be performed by the lift. In method 2100, performance of the command or trigger-override word-set is started at block 2114 and the command or trigger-override word-set is performed simultaneously during the enunciation representation of the command or trigger-override word-set at block 2112. In other implementations not shown the representation or enunciation of the command or trigger-override word-set is completed at block 2112 before performance of the command begins at block 2114.

After the command or trigger-override word-set is presented or enunciated to the user at block 2112 and performance of the command or trigger-override word-set has begun, a determination as to whether or not the command or trigger-override word-set is a command to deactivate, at block 2116. If the command or trigger-override word-set is not a deactivation command, such as "sleep" then control is passed to block 2106. If the command or trigger-override word-set is a deactivation command, then the method 2100 ends.

Figure 22:
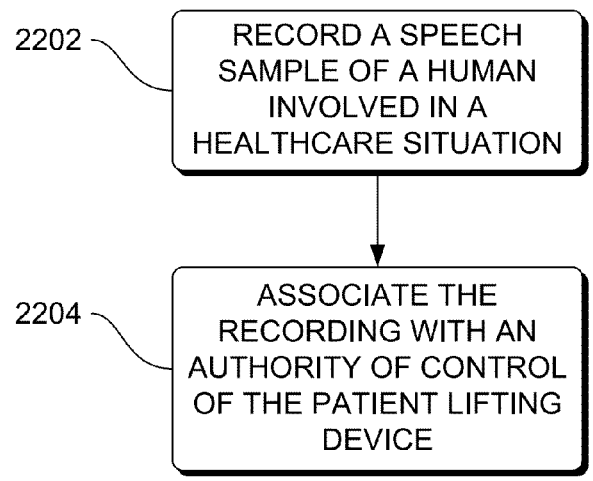
FIG. 22 is a flowchart of a method to update a database of authorities of a patient-lifting-device, according to an implementation.

FIG. 22 is a flowchart of a method 2200 to update a database of authorities of a patient-lifting-device, according to an implementation. A database of authorities is a database that associates a recording a speech sample of a human with a healthcare relationship authority of control of the patient-lifting-device. The database can be accessed as a reference to determine if particular speaker has authority to direct the patient-lifting-device to perform a particular command or any commands at all.

Method 2200 includes recording a speech sample of a human, at block 2202. In some implementations, the human is someone who will or could come into contact with a patient in a healthcare facility. For example, the human is selected from the group of humans comprising human professional healthcare providers (e.g. physicians, nurses, psychiatrists/psychologists and/or counselors), human non-professional employees of a healthcare facility (e.g. receptionists and/or janitors), patients, and friends, relatives and coworkers of the patient. In other implementations, the human is not only someone who will or could come into contact with a patient in a hospital, but also is someone who works in the healthcare facility but whose job functions do not ordinarily call them into contact with any patients, such as an IT worker in the computer data processing department. The benefit of recording a speech sample of only humans who might ordinarily come into contact with a patient is that the database of authorities will be more narrowly tailored in scope to the voices that that a voice recognition system might ordinarily be called upon to analyze. The benefit of recording a speech sample of a human whose job functions do not ordinarily call them into contact with any patients is that the database of authorities will include speech samples of people who are clearly not authorized to be involved in patient care, thus providing more definitive and conclusive negative identification of authorization by a voice recognition system, which decreases to likelihood of a false positive identification of a speaker by the voice recognition system and/or a false negative identification of the speaker by the voice recognition system.

Method 2200 also includes associating the recording with a healthcare relationship authority of control of the patient-lifting-device, at block 2204. In some implementations, the healthcare relationship authority of the human to the at least one patient is selected from the group of authorities includes 1) full authority and 2) no authority. A healthcare relationship authority of full authority provides authorization of the human to exercise or command all functions of the lift. A healthcare relationship authority of no authority provides no authority of the human to exercise or command any function of the lift.

Figure 23:
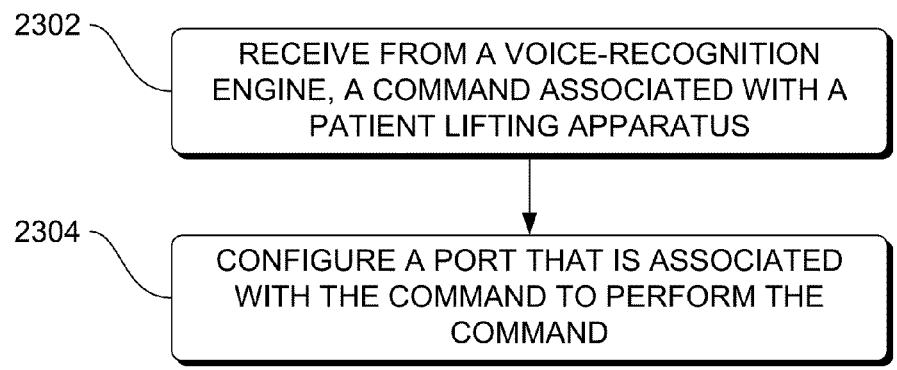
FIG. 23 is a flowchart of a method to control a device-controller of a patient-lifting-device, according to an implementation.

FIG. 23 is a flowchart of a method 2300 to control a device-controller of a patient-lifting-device, according to an implementation.

Method 2300 includes receiving from a voice-recognition unit, a command associated with a patient-lifting-device, at block 2302. Method 2300 also includes configuring a port to perform the command, at block 2304. The port is associated with the command. The mere configuring the port causes the patient-lifting-device to perform the command Methods 2400 and 2500 describe more specific implementations of method 2300.

Figure 24:
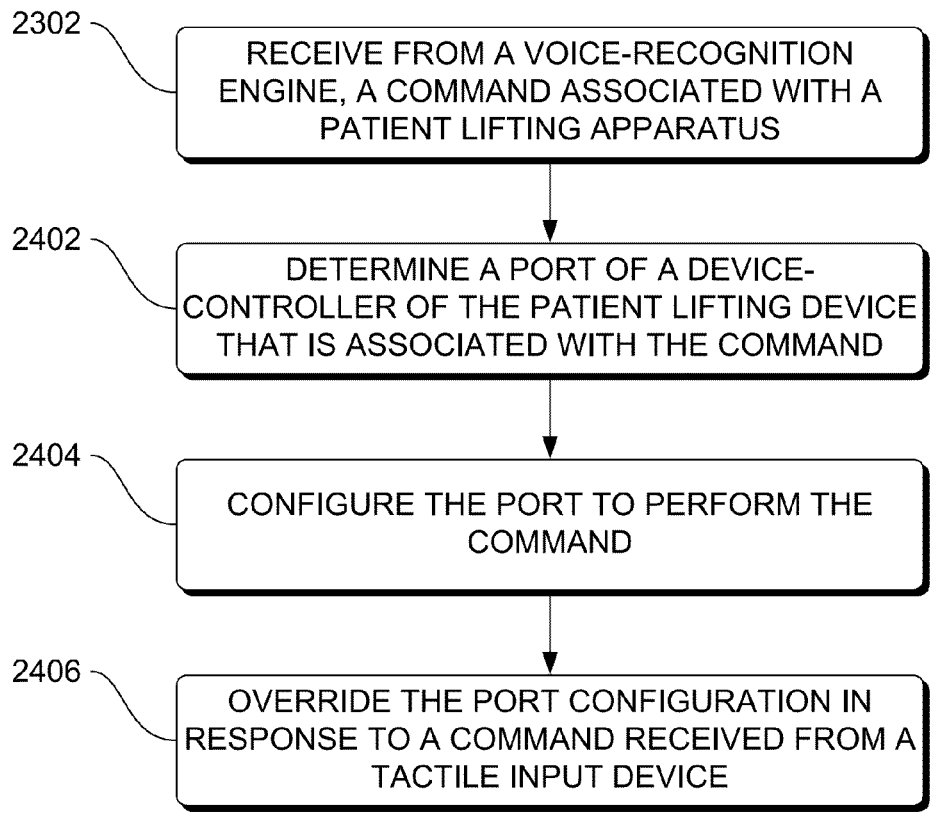
FIG. 24 is a flowchart of a method to control a device-controller of a patient-lifting-device, according to an implementation.

FIG. 24 is a flowchart of a method 2400 to control a device-controller of a patient-lifting-device, according to an implementation. Method 2400 is one implementation of method 2300.

Method 2400 includes receiving from a voice-recognition unit, a command associated with a patient-lifting-device, at block 2302. Method 2400 also includes determining or identifying which port of the device-controller of the patient-lifting-device is associated with the command, at block 2402. In some implementations, the association between the port of the device-controller of the patient-lifting-device and the command is a direct correspondence.

Method 2400 also includes configuring the identified port in order to perform the command, at block 2404. Various techniques of configuring the port using relays are described in methods 2500 and 2600.

Some implementations of method 2400 also include overriding the configuration of the port in response to a command received from a tactile input device, such as a hand-held controller, or an input device other than a microphone and voice-recognition unit. The configuration of the port is overridden to provide higher priority to the other input device, which is helpful in some situations where the command from the other input device is considered to be more reliable and/or accurate or where the command from the other input device is designated for any reason or even arbitrarily as being the input device with the highest priority.

Figure 25:
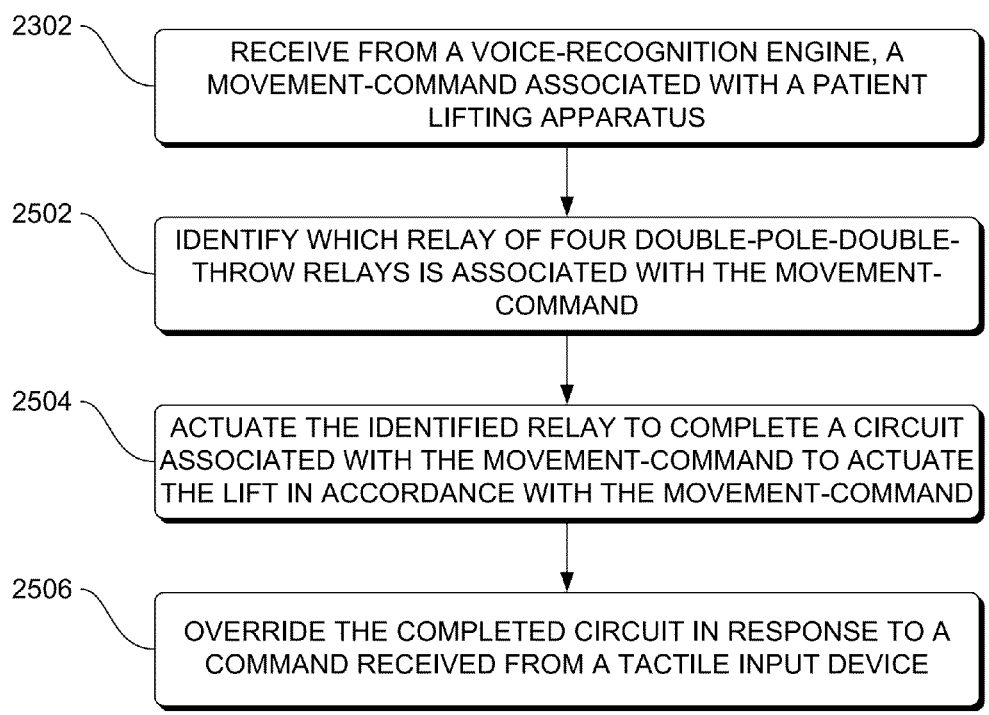
FIG. 25 is a flowchart of a method to control a device-controller of a patient-lifting-device, according to an implementation.

FIG. 25 is a flowchart of a method 2500 to control a device-controller of a patient-lifting-device, according to an implementation. Method 2500 is one implementation of method 2300.

Method 2500 includes receiving from a voice-recognition unit, a movement-command associated with a patient-lifting-device, at block 2302. The movement command can be in anyone of a number of electronic formats, such as a transient signal, a text-encoded binary representation, and/or a numerical representation encoded in binary.

Figure 44:
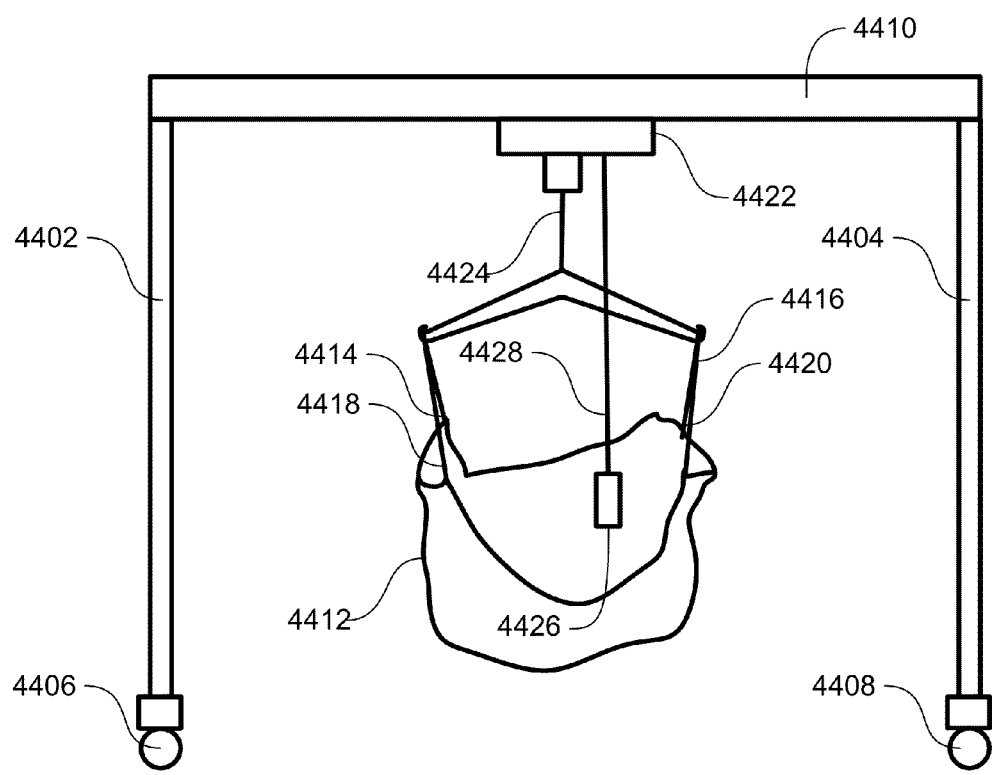
FIG. 44 is a block diagram of a two dimensional patient-lifting-device, according to an implementation that is specifically adapted for lifting a patient out of bed.
Figure 45:
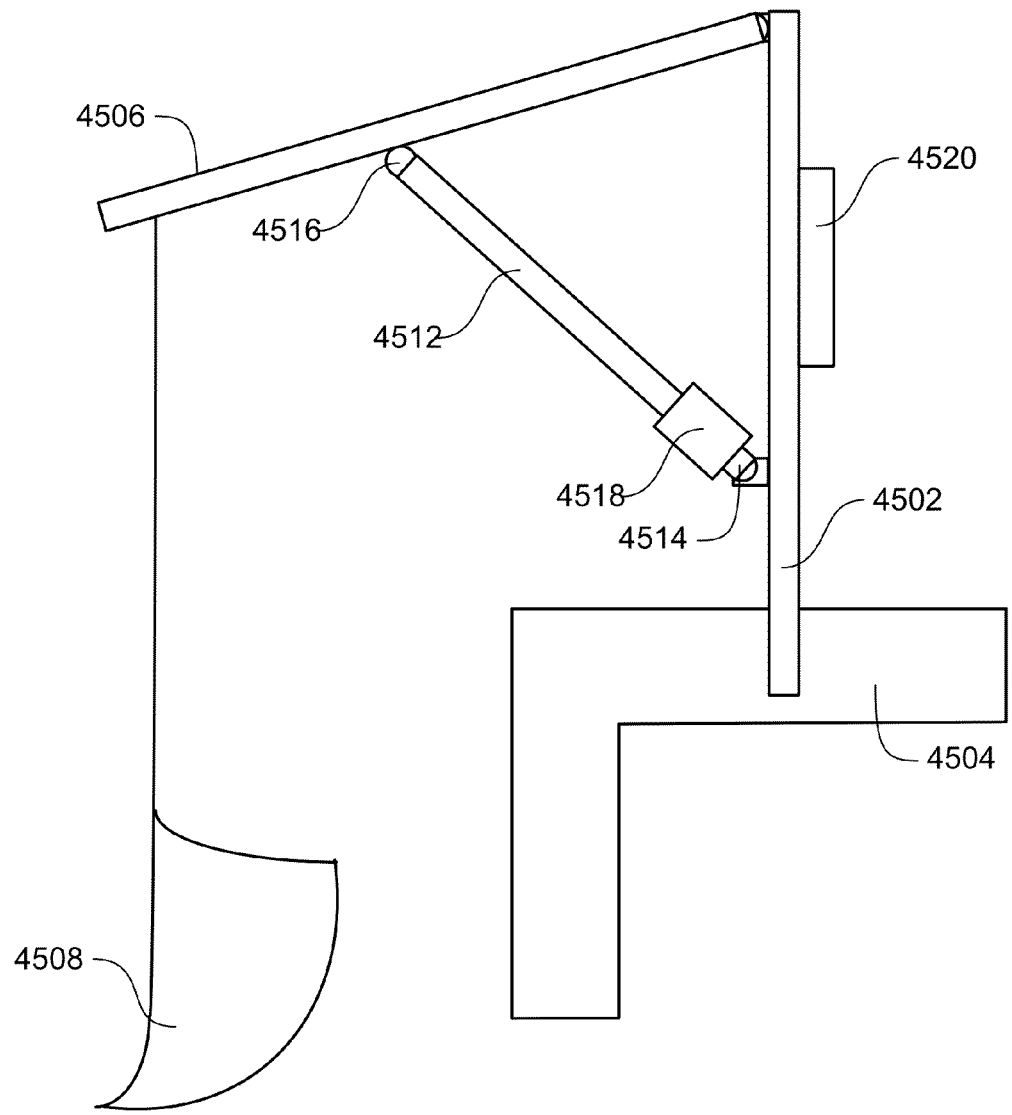
FIG. 45 is a block diagram of a one dimensional patient-lifting-device, according to an implementation that is specifically adapted for lifting a patient in and out of a pool.

In regards to the movement-command, in some implementations in which the lifting apparatus provides electrically or hydraulically actuated movement in one dimension (along a line) such as shown in the one dimensional patient-lifting-device 4500 is in FIG. 45, the movement-command is one of two different commands, "up," and "down." In some implementations in which the lifting apparatus provides electrically or hydraulically actuated movement in two dimensions (along a plane) such as shown in the two dimensional patient-lifting-device 4500 in FIG. 44, the movement-command is one of four different commands, "up," "down," "forward," and "backward." In some implementations in which the lifting apparatus provides electrically or hydraulically actuated movement in three dimensions (throughout a volume), the movement-command is one of six different commands, "left," "right," "up," "down," "forward," and "backward."

Further in regard to the movement-command, in some implementations in which the lifting apparatus has a safety halt feature and that provides electrically or hydraulically actuated movement in one dimension (along a line) such as shown in the one dimensional patient-lifting-device 4500 in FIG. 45, the movement-command is one of five different commands, "up," "down," "stop," halt," and "help." The "stop," halt," and "help" commands are cessation-commands that can be enunciated by an operator to end movement of the lifting apparatus. In some implementations in which the lifting apparatus has a safety halt feature and that provides electrically or hydraulically actuated movement in two dimensions (along a plane) such as shown in the two dimensional patient-lifting-device 4400 in FIG. 44, the movement-command is one of seven different commands, "up," "down," "forward," "backward," "stop," halt," and "help." In some implementations in which the lifting apparatus has a safety halt feature and that provides electrically or hydraulically actuated movement in three dimensions (throughout a volume), the movement-command is one of nine different commands, "left," "right," "up," "down," "forward," "backward," "stop," halt," and "help."

Method 2500 also includes identifying or determining which relay of a plurality of relays is associated with the movement-command, at block 2502. The number of relays is equal to the number of movement-commands that are not "halt" or "stop." One relay for each direction of movement. For example, where the movement-commands are "up," "down," "forward," and "backward" the number of relays is four. In another example, where the movement-commands are "left," "right," "up," "down," "forward," and "backward" the number of relays is six.

In some implementations, each of the plurality of relays is a single-pole-single-throw relay. In other implementations, each of the plurality of relays is a double-pole-double-throw (DPDT) relay. In other implementations, some of the plurality of relays is a single-pole-single-throw relay and some of the plurality of relays is a DPDT relay.

Method 2500 also includes actuating the identified relay, at block 2504. Actuating the identified relay causes a circuit to be completed or closed, in which the completed/closed circuit being associated with the movement-command. Completion/closing of the circuit that is associated with the direction of movement of the patient-lifting-device that is the same as the movement-command actuates the patient-lifting-device in accordance with the movement-command.

A normally open (NO) relay is implemented in situations where movement is actuated by completing a circuit, such as described at block 2504. However, in other implementations where movement is actuated by opening or breaking a circuit, a normally-closed (NC) relay is used.

Some implementations of method 2500 also include override the completed circuit in response to a command received from a tactile input device, such as a hand-held controller, or an input device other than a microphone and voice-recognition unit, at block 2506. One implementation of overriding the completed circuit is opening the circuit. The completed circuit is overridden to provide higher priority to the other input device, which is helpful in some situations where the command from the other input device is considered to be more reliable and/or accurate or the command from the other input device is designated rather arbitrarily as being the input device with the highest priority.

Figure 26:
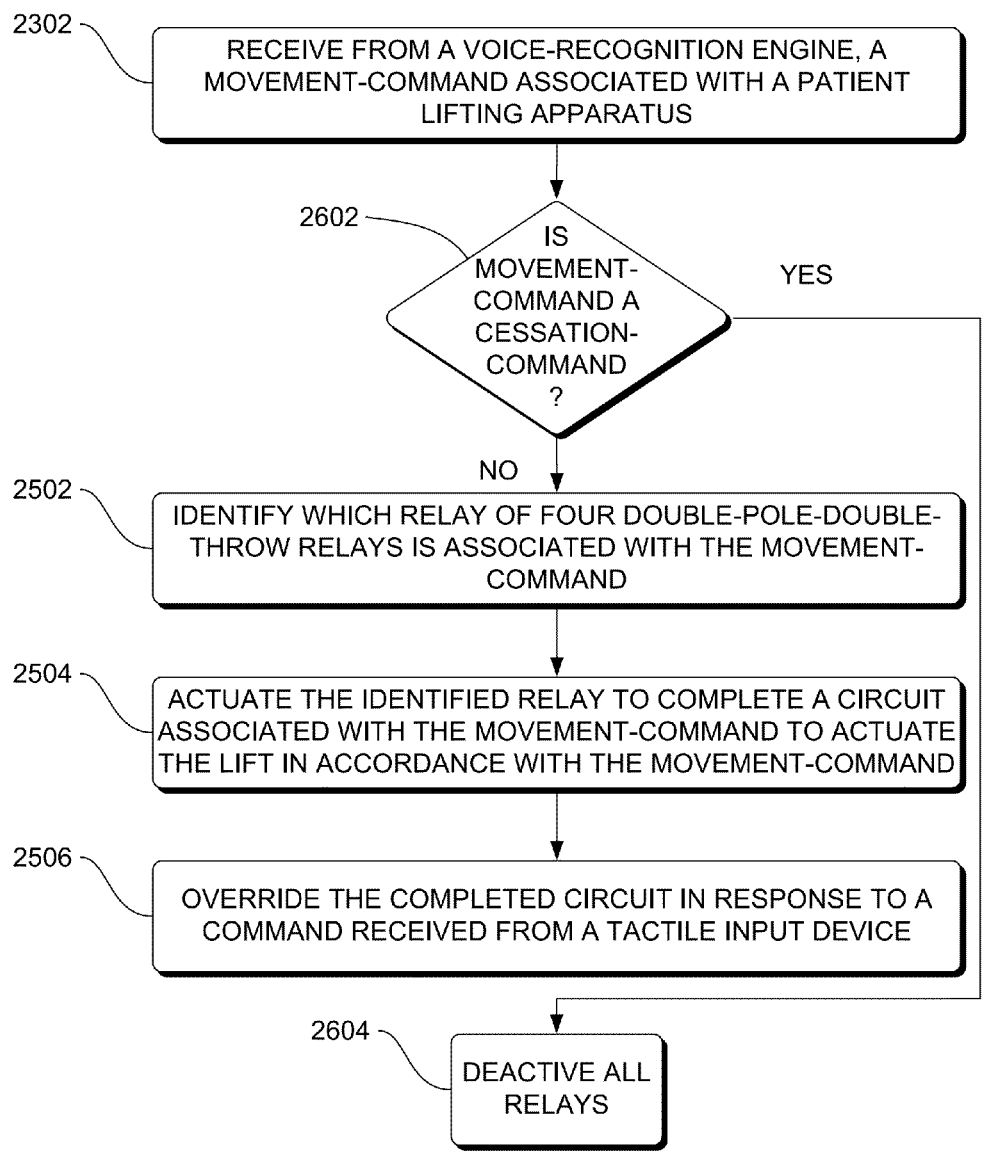
FIG. 26 is a flowchart of a method to control a device-controller of a patient-lifting-device, according to an implementation.

FIG. 26 is a flowchart of a method 2600 to control a device-controller of a patient-lifting-device, according to an implementation. Method 2600 is one implementation of method 2500.

In method 2600, after the movement-command is received from the voice-recognition engine, the movement-command is tested to determine or evaluate if the movement-command is a cessation-command, at block 2602. Examples of cessation-command include "stop," "halt" and "help." If the movement-command is a cessation-command, then in some implementations, all relays are deactivated (e.g. normally-open relays are opened) at block 2604. In other, implementations, if the movement-command is a cessation-command, then only the actuated (active) relay(s) are deactivated. If the movement-command is not a cessation-command, then the method proceeds with the next action of identifying or determining which relay of a plurality of relays is associated with the movement-command, at block 2502, and continuing thereafter.

Figure 27:
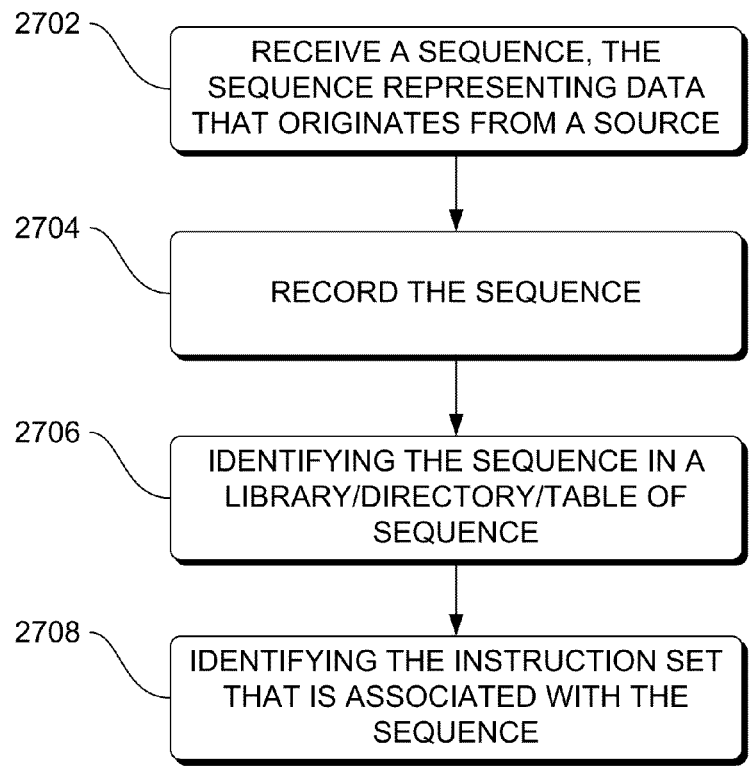
FIG. 27 is a flowchart of a method to control a device-controller of a patient-lifting-device, according to an implementation.

FIG. 27 is a flowchart of a method 2700 to control a device-controller of a patient-lifting-device, according to an implementation. Method 2700 includes receiving 2702 a sequence. The sequence represents data that originates from a source; the source is selected from the group consisting of a human and the device. One example of the device is the multisensor 1106 in FIG. 11. Some implementations of receiving 2702 includes reading a sequence of one or more sensory stimulus and reading a sequence of one or more multisensory stimulus. Some implementations of receiving 2702 includes reading a sequence of one or more sensory action and reading a sequence of one or more multisensory action. Some implementations of receiving 2702 includes reading a sequence of one or more sensory input and reading a sequence of one or more multisensory input. In one example, a sensory stimulus represents a position of an eye that relates to an action of a device.

Method 2700 also includes recording 2704 the sequence.

At least one sensory stimulus is uniquely associated to an instruction set in a dynamically configurable library/directory/table. Method 2700 includes identifying 2706 the sequence in a library/directory/table of sequences. Each sequence is associated with an instruction set. Method 2700 also includes identifying 2708 the instruction set that is associated with the sequence.

Figure 28:
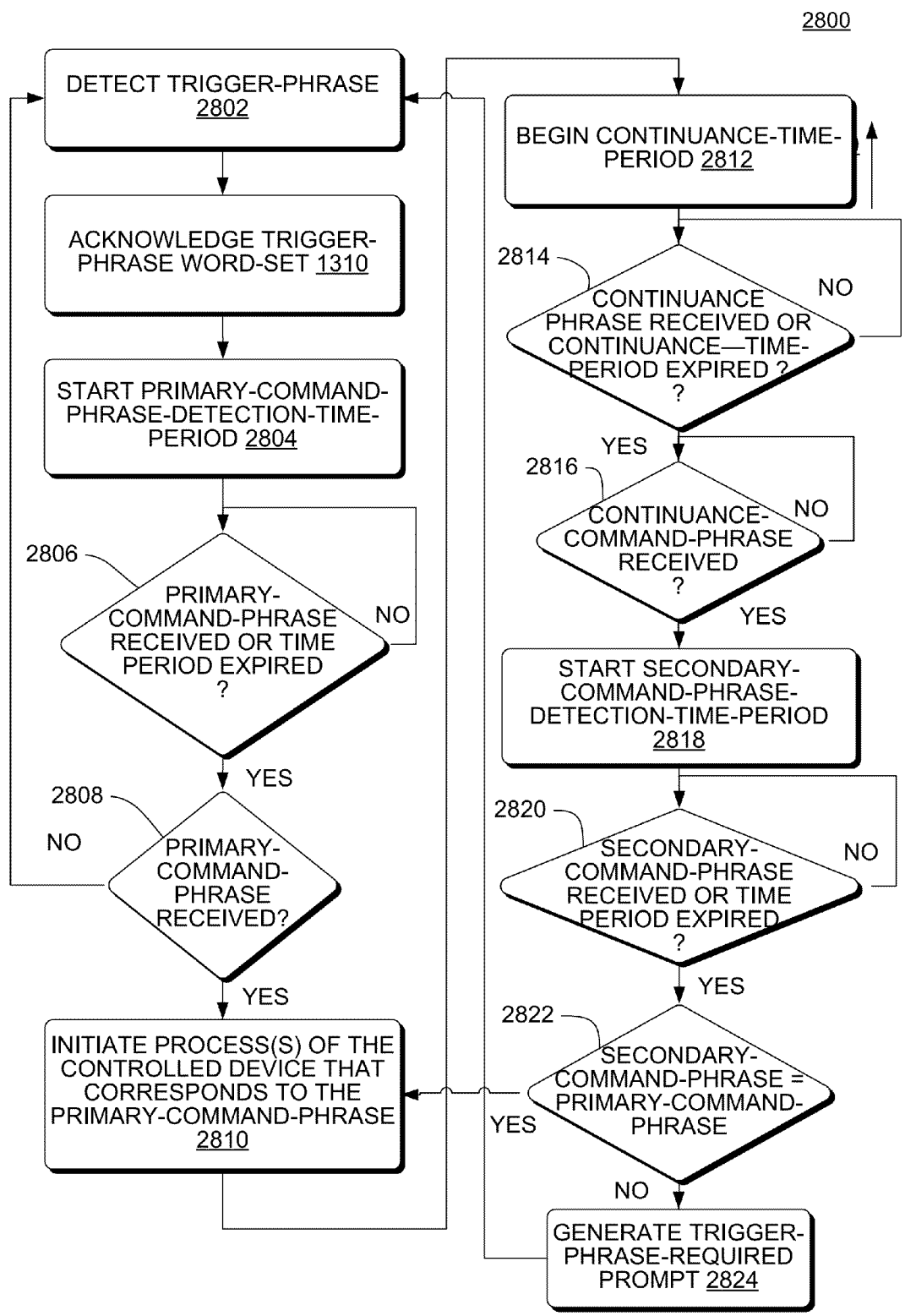
FIG. 28 is a flowchart of a method to control a device having a safety stop, according to an implementation.

FIG. 28 is a flowchart of a method 2800 to control a device having a safety stop, according to an implementation. In method 2800, movement of the controlled device will cease after a particular time period if no indication to continue movement is detected or received. In some implementations, system 100 defaults to stopping all movement after a duration of performance of a movement-command.

In some implementations, method 2800 is adapted for use in controlling devices in response to a command of an occupied-command-set. An occupied-command-set is a plurality of commands that are performed only when a controller device is occupied by a human or other subject that is being transported.

In some implementations, method 2800 is performed continuously starting when the controller device is powered on or otherwise available to use, until the controlled device is powered-off or otherwise becomes unavailable for use.

Some implementations of method 2800 include detecting a trigger-phrase, at block 2802. In some implementations, the trigger-phrase-word-set includes commands that indicate the intention by the operator to provide a functional command or directive to the patient-lifting-device. Examples of a trigger-phrase-word-set include "molift command," "lift command," and "attention." Some implementations of the action at block 2802 include the method 1100 in FIG. 11.

Thereafter, an acknowledgment of the trigger-phrase-word-set is generated and presented in the local environment, at block 1310. For example if the trigger-phrase-word-set "Molift™ command" is received at block 1306, then a "beep" sound is enunciated. The acknowledgement provides a cue to the speaker of the trigger-phrase-word-set that the system understands that the user has enunciated a trigger-phrase-word-set and that the speaker intends to enunciate a command for performance by the system. In other implementations, other acknowledgements other than a "beep" sound are generated and presented, such as generation of a vibration by a device that is placed adjacent to a human subject or placed adjacent to another item that is adjacent to the human subject.

Some implementations of method 2800 include starting or initiating a timer, the timer having a fixed duration or period, at block 2804. In the duration of the timer (during execution of the timer), before the timer expires, at least one device of at least one or more input devices is monitored for receipt of a primary-command-phrase. If a primary-command-phrase is not determined to be received or the timer has not expired, at block 2806, method 2800 continues at block 2806. This loop continues to poll until the primary-command-phrase is received or the timer expires. If a primary-command-phrase is determined to be received or the timer expires, at block 2806, method 2800 continues at block 2808. When the at least one or more input devices consists of at least two input devices, the two or more input devices are multisensory input devices.

In some implementations, the primary-command-phrase is a movement-command. In implementations where the device is a patient-lifting-device, and the patient-lifting-device provides electrically or hydraulically actuated movement in two dimensions (along a plane), such as shown in the two dimensional patient-lifting-device 4400 in FIG. 44, the movement-command is one of two different commands, "up," and "down." In some implementations in which the patient-lifting-device provides electrically or hydraulically actuated movement in two dimensions (along a plane) such as shown in the two dimensional patient-lifting-device 4400 in FIG. 44, the movement-command is one of four different commands, "up," "down," "forward," and "backward." In some implementations in which the patient-lifting-device provides electrically or hydraulically actuated movement in three dimensions (throughout a volume), the movement-command is one of six different commands, "left," "right," "up," "down," "forward," and "backward."

After a primary-command-phrase is received or the timer expires, a determination is made as to whether or not a primary-command-phrase is received, at block 2808. If a primary-command-phrase is not received, method 2800 continues at block 2802. Otherwise, if a primary-command-phrase is received, a process of the controlled device is initiated at block 2810, in which the process corresponds to the primary-command-phrase. In one example of initiating a process of a controlled device, FIG. 28 shows a device-controller 2800 in which a relay is actuated to complete an electrical circuit to provide current flow to a motor to provide movement of a patient-lifting-device in accordance with a primary-command-phrase, movement-command or other command.

Some implementations of method 2800 include starting or initiating a continuance-time-period timer, the continuance-time-period timer having a fixed duration or period, at block 2812. In the duration of the continuance-time-period timer (during execution of the continuance-time-period timer), before the continuance-time-period timer expires, at least one device of at least one or more input devices is monitored for receipt of a continuance-phrase. If a continuance-phrase is not determined to be received or the continuance-time-period timer has not expired, at block 2814, method 2800 continues at block 2814. This loop continues to poll until the continuance-phrase is received or the continuance-time-period timer expires. If a continuance-phrase is determined to be received or the continuance-time-period timer expires, at block 2814, method 2800 continues at block 2816.

Some implementations of method 2800 include after a continuance-command-phrase is received or the timer expires, a determination is made as to whether or not a continuance-command-phrase is received, at block 2816. If a continuance-command-phrase is not received, method 2800 continues at block 2812. Otherwise, if a continuance-command-phrase is received, a process of the controlled device initiated at block 2810, method 2800 continues at block 2804.

Some implementations of method 2800 include starting or initiating a timer, the timer having a fixed duration or period, at block 2818. In the duration of the timer (during execution of the timer), before the timer expires, at least one device of at least one or more input devices is monitored for receipt of a secondary-command-phrase. If a secondary-command-phrase is not determined to be received or the timer has not expired, at block 2820, method 2800 continues at block 2820. This loop continues to poll until the secondary-command-phrase is received or the timer expires. If a secondary-command-phrase is determined to be received or the timer expires, at block 2820, method 2800 continues at block 2822.

Some implementations of method 2800 include determining whether or not the secondary-command-phrase is the same as the primary-command-phrase, at block 2822. If the secondary-command-phrase is the same as the primary-command-phrase, the method continues at block 2810. If the secondary-command-phrase is not the same as the primary-command-phrase, then in some implementations of method 2800 include generating a trigger-phrase-required prompt and presenting the trigger-phrase-required prompt in the environment in the close vicinity of the controlled device and thereafter method 2800 continues at 2812.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic non-transitory storage devices, or any other media which can be used to store computer-intelligible information and which can be accessed by the computation resource 4702.

Figure 29:
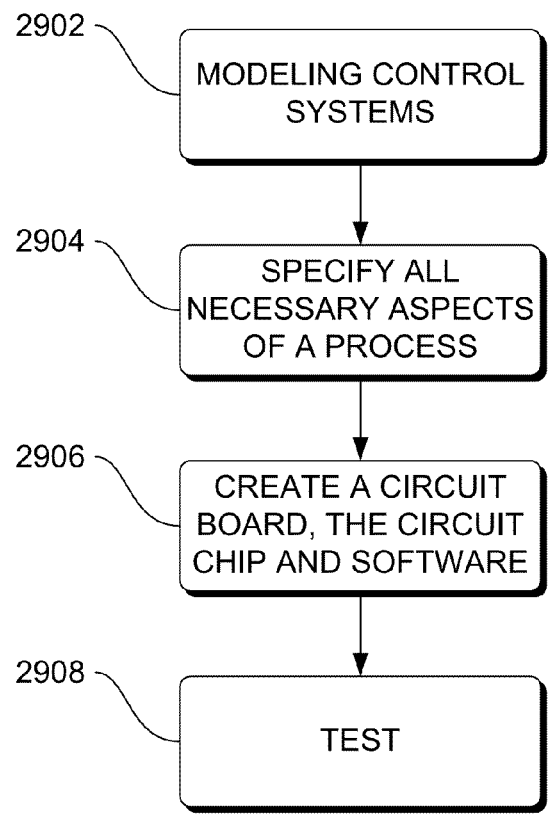
FIG. 29 is a flowchart of a method of customizing systems in FIG. 1 and FIG. 2, according to an implementation.

FIG. 29 is a flowchart of a method of customizing systems 100 and 200, according to an implementation. A family of controls and systems can be utilized by manufacturers and customizers. The family controls are organized into four general categories: (1) Wireless control receivers—incorporated into everyday electrical device(s) 114 by manufactures; (2) General purpose remote and voice controls; (3) Multisensory controls and (4) Programmable circuit controls. The general purpose remote and voice controls, multisensory controls and programmable circuit controls is operable to control the wireless remote receivers. The wireless control receivers are incorporated into everyday electrical device(s) 114 by manufacturers. For example, the On/Off Controller, Servomotor Controller, Stepping Motors Controller and Digitally Controlled Potentiometers (DCP's), all which are wireless. By simply replacing the standard on/off switch with the system, the wireless controller with a remote and its built into device is operable to adapt to any product that has an on/off component. This process to manufacture and distribute is very inexpensive. The Stepping Motors Controller could regulate the speed progression of a ceiling fan. Each Controller has a specific function using a globally unique identifier (GUID). Every device must be identifiable. Working together, the functions that are controllable are numerous. These wireless remotes will be programmed as a radio frequency device and not an IR (line of sight). The Multisensory Integrated Programmable Control (MIPC) is an important tool in developing a product accordingly. MIPC is a system of hardware and software that is operable to detect multiple sensory stimulus and other inputs and is operable to interface to control virtually any device or process on the market that is electric. An example use of the MIPC is that of a motorized wheelchair. Motorized wheelchairs are commonly controlled by a joystick device.

Method 2900 includes modeling each control system to the components as (objects) in a Visualization Modeler, at block 2092. Modeling 2902 an object can include creating a graphical representation of the object and assigning attributes to the graphical representation. In some implementations, a wide variety of standard bus interfaces, hardware and software tools that allow for the creation of physical circuits and related process logic strictly through its software, are integrated.

Working through a sensory stimulus event (SSE), any detected stimulus forms a voice command to pressure on a micro switch in the circuit. Thus, for simplicity's sake the stimulus enables the voice command to control the device and process. Working in conjunction with Process Definition Languages (PDL), VHDL, VHSIC, hardware description language, used as a design-entry language for field-programmable gate arrays and application-specific integrated circuits in electronic design automation of digital circuits, and a Control Process Definition (CPD), a set of data expressed in OPDL sufficient to specify all necessary aspects of a process, at block 2094. CPD is used to state explicitly in detail the sequence of actions, extent, limits, and criteria of a process that is sufficient for the system to successfully execute the process.

A Process and Circuit Integration Modeler as a tool that enables modeling, design, analysis and generation of Control Process Definitions and related circuit synthesis to create a circuit board, the circuit chip and software, at block 2906. The manufacturer or customizer uses process and Circuit Integration Modeler (CIM). The CIM produces a physical circuit. The 3 sensory interfaces are built into our circuit board and are accessible through software. Considering the time consuming problem of customizing a wheelchair for the individual with no movement of his hand, the system makes the accommodation relatively simple.

Method 2900 also includes interviewing the operator and testing a menu system through the blow tube and the directional movement from his head, at block 2098. In some implementations, the customization process 2900 is flexible to the extent that the customizer is operable to create an actual control system and the individual is operable to create and modify the system on the spot through software changing actual circuits. In an independent survey, it was estimated that approximately 75% of all service providers for customized wheelchairs ordered were funded through Medicaid waivers. The cost effectiveness greatly reduces the existing dollars expended by Federal and State Medicaid and Medicare programs thereby increasing the ability to service more people.

Figure 30:
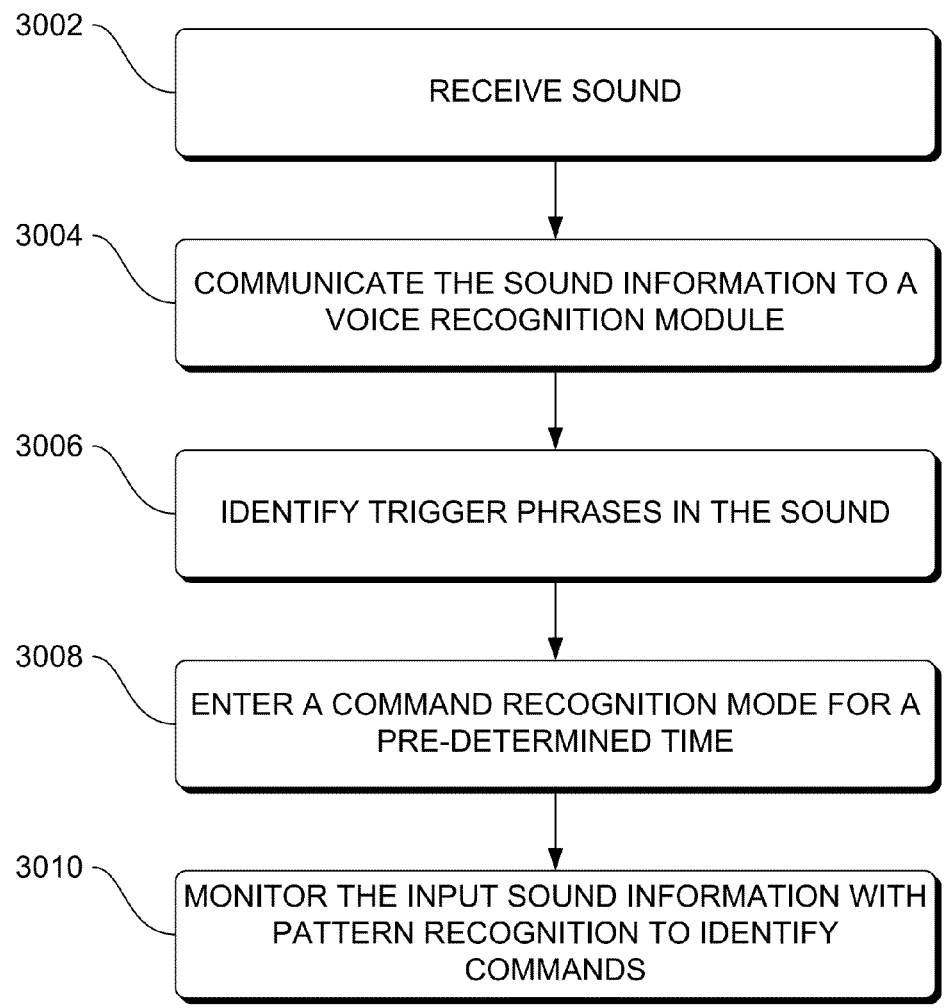
FIG. 30 is flowchart of a process of a voice and manual controlled switch, such as switch 3600 in FIG. 36, according to an implementation.

FIG. 30 is flowchart of a process of a voice and manual controlled switch, such as switch 3600 in FIG. 36, according to an implementation. Method 3000 includes receiving sound inputs into an audio circuit 3604, at block 3002, and method 3600 includes the audio circuit 3604 communicating the sound information to a voice recognition module 3606, at block 3004. Method 3000 includes identifying trigger phrases in the sound, at block 3006. Once a trigger phrase is identified voice recognition module 3606 enters a command recognition mode for a pre-determined time, at block 3008. During the command recognition mode voice recognition module 3606 monitors the input sound information with pattern recognition to identify commands "on", "light on", "off", "light off" or user specified commands, at block 3010. If voice recognition module 3606 identifies a command phrase the module 3606 then compares the value of command phrase, to the value of the previously received command phrase or the default value of (off) if no previous command phrase is recorded. If the value of the command phrase differs from the previously received command phrase then the energized state of terminal 3608 is reversed by reversing the energized stay of transistor 3610 and in turn reversing the state of single-pole double-throw relay 3612.

Figure 31:
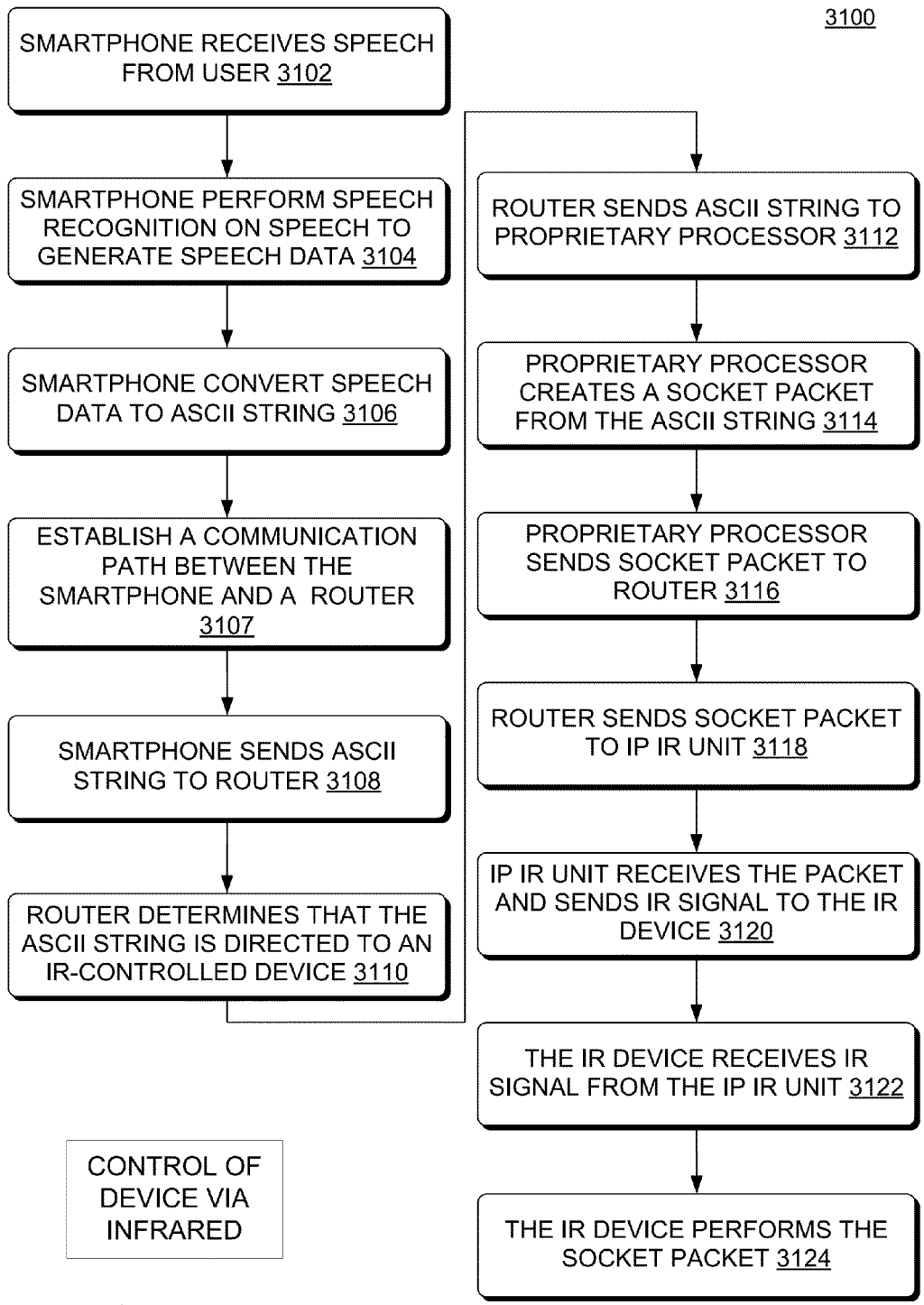
FIG. 31 is a flowchart of a method of a wireless mobile device controlling one or more controllable electrical devices that have an infrared control interface, according to an embodiment.

FIG. 31 is a flowchart of a method 3100 of a wireless mobile device controlling one or more controllable electrical devices that have an infrared control interface, according to an embodiment.

Method 3100 includes a smartphone (or other wireless mobile device) receiving audio speech, at block 3102. The audio speech is associated with one of the controllable electrical devices. The audio speech is received at a microphone of the wireless mobile device. One example of the smartphone is the mobile device in FIG. 46.

Method 3100 also includes the smartphone determining which controllable electrical device the smartphone is directed. To which controllable electrical device the smartphone is directed is determined from the screen on the smartphone that the user has selected, as described in FIG. 51-56. A vocabulary set is selected that is specifically limited to the selected controllable electrical device. The selected vocabulary set includes data that is relevant only to the selected controllable electrical device, which is greatly helpful providing faster processing of the speech data in action 3104, but also is greatly helpful in providing more accurate processing of the speech data in action 3104. Using a vocabulary set that is specifically limited to the selected controllable electrical device is faster and more accurate because the vocabulary set does not include information and commands for devices other than the selected controllable electrical device, which greatly reduces the information and commands that the smartphone needs to consider, which is not only faster, but reduces the nuances that introduce ambiguity in a large vocabulary set for many more devices than the selected controllable electrical device. For example, when the selected controllable electrical device is a light that supports only the functions of ON and OFF, the selected vocabulary set for the light includes only information and commands that are relevant to the ON and OFF functions of the light, and does not include information relevant to the whole "universe" of other controllable electrical devices. Processing the vocabulary set for the light is very much faster and more accurate than processing the vocabulary for all controllable electrical devices. In one implementation, a linguist component 1616 in FIG. 16 is limited to the selected controllable electrical device.

Method 3100 also includes the smartphone performing speech recognition on the audio speech in reference to the selected vocabulary set to generate speech data, at block 3104. Method 3100 also includes the smartphone converting speech data to an ASCII string, at block 3106. The ASCII string represents control data of the selected controllable electrical device. Method 3100 also includes establishing a WIFI communication path with a wireless WIFI wireless router that is associated with the at least one controllable electrical device at the wireless mobile device, at block 3107, which can be and needs to be performed at any point before action 3108. Method 3100 also includes the smartphone sending the ASCII string to a WIFI wireless router that is associated with the at least one controllable electrical device (either through WIFI or through the Internet), at block 3108.

Method 3100 also includes the router receiving the ASCII string from the smartphone and the router determining that at the least one controllable electrical device of the ASCII string is controlled through an infrared interface, which yields an associated infrared interface and the router determining a propriety processor that is associated with the associated infrared interface, which yields an associated proprietary processor, at block 3110. Method 3100 also includes the router sending the ASCII string from the WIFI wireless router to the associated proprietary processor; at block 3112.

Method 3100 also includes the associated proprietary processor receiving the ASCII string from the router and the associated proprietary processor creating a socket from the ASCII string, at block 3114. The socket packet includes data that is relevant only to the selected controllable electrical device. Method 3100 also includes the associated proprietary processor sending the socket packet from the associated proprietary processor to the WIFI wireless router that is associated with the selected controllable electrical device, at block 3116. The transmission of the sending has a destination address of an IP-to-IR controller that controls the selected controllable electrical device. The IP-to-IR controller is an Internet-protocol to infrared controller such as the model IP2IR manufactured by Global Cache, 160 East California Street, PO Box 1659, Jacksonville, Oreg. 97530). In some implementations, the IP-to-IR controller is capable of transceiving Internet protocol communications from and to infrared communications. In some implementations, the IP-to-IR controller is capable of only receiving Internet protocol communications and sending the communications over infrared.

For the IP2IR IP-to-IR controller manufactured by Global Cache, communication with the IP-to-IR controller is accomplished by opening a TCP socket on Port 4998. All commands and data, with the exception of serial (RS232) data, are communicated through Port 4998.

The ASCII string is sent using a 'sendir' command with the following syntax:

--- sendir,<connectoraddress>,<ID>,<frequency>,<repeat>,<offset>,<on1>,<off1>,<on2>,<off2>,....,<onN>,<offN> (where N is less than 260 or a total of 520)

--- where;

<connectoraddress> is A connector's address is its position within a module, starting at 1 on the left, and increasing sequentially as you move to the right. A complete connector address includes the module address and the connector location in the module, separated by a colon

---

<ID> is |0|1|2|...|65535|
<frequency> is |15000|15001|....|500000| (in hertz)
<repeat> is |1|2|....|50| (the IR command is sent <repeat> times)
<offset> is |1|3|5|....|383| (used if <repeat> is greater than 1, see below)
<on1> is |1|2|...|65635| (number of pulses)
<off1> is |1|2|...|65635|(absence of pulse periods of the carrier frequency)

---

The <repeat> is the number of times an IR transmission is sent, if it is not halted early via a stopir or another IR command. Values above 50 are accepted, but IR commands are sent only the maximum 50 times. In all cases, the preamble is only sent once (see <offset> below). An <offset> applies when the <repeat> is greater than 1. For IR commands that have preambles, an <offset> is employed to avoid repeating the preamble during repeated IR timing patterns. The <offset> value indicates the location within the timing pattern to start repeating the IR command as indicated below. The <offset> will always be an odd value since a timing pattern begins with an <on> state and must end with an <off> state.

Method 3100 also includes the WIFI wireless router that is associated with the at least one controllable electrical device receiving the socket packet at from the proprietary processor; and sending the socket packet to the IP-to-IR controller, at block 3118.

Method 3100 also includes the IP-to-IR controller receiving the socket packet and from the WIFI wireless router that is associated with the at least one controllable electrical device and the IP-to-IR controller sending an infrared signal in accordance with the socket packet to an infrared port of the selected controllable electrical device, at block 3120.

Method 3100 also includes the infrared port of the selected controllable infrared electrical device receiving the infrared signal in accordance with the socket packet from the IP-to-IR controller, at block 3122 and method 3100 also includes the selected controllable electrical device performing a function in accordance with the IR signal, and thus controlling the selected controllable electrical device in accordance to the audio speech, at block 3124.

Figure 32:
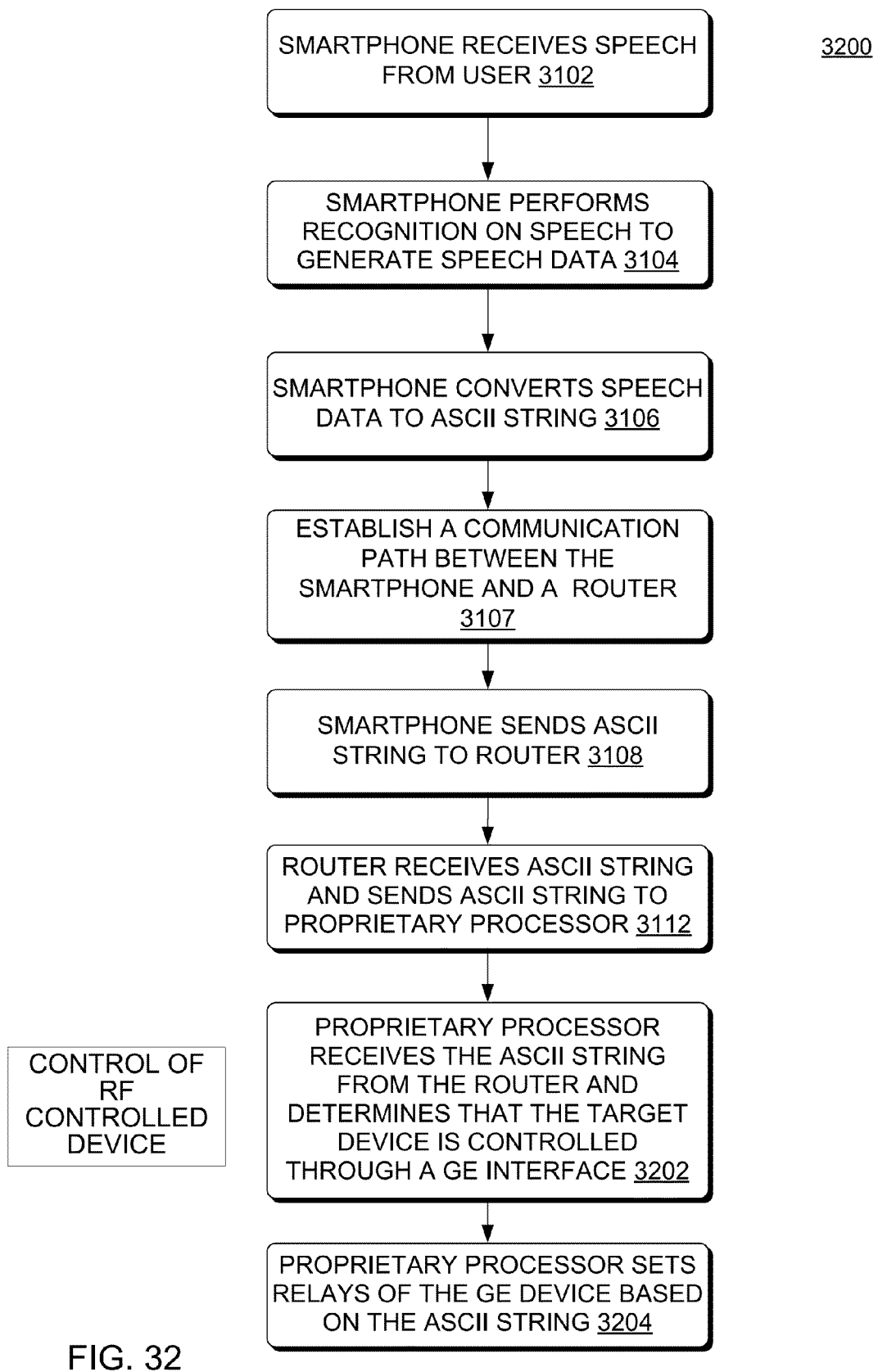
FIG. 32 is a flowchart of a method of a wireless mobile device controlling an electrical device that has an infrared control interface, according to an embodiment.

FIG. 32 is a flowchart of a method 3200 of a wireless mobile device controlling an electrical device that has an infrared control interface, according to an embodiment.

Method 3200 includes a smartphone or other wireless mobile device receiving audio speech from user through a microphone, at block 3102. Method 3200 also includes the smartphone performing speech recognition on the audio speech to generate speech data, which generates speech data, at block 3104. Method 3200 also includes the smartphone converting speech data to an ASCII string, at block 3106. Method 3100 also includes establishing a WIFI communication path between the WIFI wireless router and the smartphone, at block 3107. Method 3200 also includes the smartphone sending the ASCII string to a router (either through WIFI or through internet), at block 3108.

Method 3200 also includes the router receiving the ASCII string from the smartphone and the router sending the ASCII string to a proprietary processor, at block 3112.

Method 3200 also includes the proprietary processor receiving the ASCII string from the router and the proprietary processor determining that the target device is controlled through a radio frequency (RF) interface, such as a GE Smart Remote Plus Transmitter RF102TXPS, at block 3202. Method 3200 also includes the proprietary processor setting relays of the RF interfaces based on the ASCII string, at block 3204, and the RF controllable electrical device is operable to receive an RF signal at the RF interface 4822 of the RF controllable electrical device and operable to perform a function in accordance with the infrared signal, providing control of an IR controllable electrical device 4804 in accordance with the audio speech.

Hardware and Operating Environment

FIG. 33 is a block diagram of a voice-recognition apparatus 3300 to control a patient-lifting-apparatus, according to an implementation. The voice-recognition apparatus 3300 is one implementation of voice-recognition unit 804 in FIG. 8. The voice-recognition apparatus 3300 receives input from any one of a number of input mediums, such as audio, and therefrom controls a patient-lifting-apparatus. The voice-recognition apparatus 3300 can fit inside the housing of conventional patient-lifting-apparatus and can communicate with and control conventional patient-lifting-apparatus using the conventional existing electrical circuitry of patient-lifting-apparatus. The voice-recognition apparatus 3300 helps improve control of the patient-lifting-apparatus by receiving input from any one of a number of input mediums, such as audio. In the example of audio, the voice-recognition apparatus 3300 improves the ease and convenience with which an operator can control the patient-lifting-apparatus by providing a voice interface to the patient-lifting-apparatus. In general, the voice-recognition apparatus 3300 improves the ease and convenience with which an operator can control the patient-lifting-apparatus by providing a command interface to the patient-lifting-apparatus other than a handheld control device, such as the handheld control device 4426 shown in FIG. 44.

Voice-recognition apparatus 3300 includes a microcontroller, processor or microprocessor 3302, such as a RSC 6502 microcontroller. The 6502 is an 8-bit processor with a 16-bit address bus. The internal logic runs at the same speed as the external clock rate, and having clock speeds typically in the neighborhood of 1 or 2 MHz. The 6502 has a relatively simplistic state machine implemented by combinatorial (clockless) logic. A two phase clock (supplying two synchronizations per cycle) can thereby control the whole machine-cycle directly. The 6502 microcontroller is not sequenced by a microcode read-only-memory but uses a programmable logic array for instruction decoding and sequencing. Like most typical eight-bit microprocessors, the 6502 microcontroller does some limited overlapping of fetching and execution. The low clock frequency moderates the speed requirement of memory and peripherals attached to the 6502 microcontroller, as only about 50% of the clock cycle is available for memory access (due to the asynchronous design, this percentage varies strongly among chip versions). The 6502 microcontroller is minimalistically engineered and efficiently manufactured and therefore inexpensive. Like its precursor, the Motorola 6800 (but unlike Intel 8080 and similar microprocessors) the 6502 microcontroller has very few registers. The registers of the 6502 microcontroller include one 8-bit accumulator register (A), two 8-bit index registers (X and Y), an 8-bit processor status register (P), an 8-bit stack pointer (S), and a 16-bit program counter (PC). The subroutine call/scratchpad stack's address space is hardwired to memory page $01, i.e. the address range $0100-$01FF (256-511). Software access to the stack is performed via four implied addressing mode instructions whose functions are to push or pop (pull) the accumulator or the processor status register. The same stack is also used for subroutine calls via the JSR (Jump to Subroutine) and RTS (Return from Subroutine) instructions, and for interrupt handling. The 6502 microcontroller uses the index and stack registers effectively with several addressing modes, including a fast "direct page" or "zero page" mode, similar to that found on the PDP-8, that accessed memory locations from address 0 to 255 with a single 8-bit address (saving the cycle normally required to fetch the high-order byte of the address)—code for the 6502 use the zero page much as code for other processors do have used registers. Addressing modes also include implied (1 byte instructions); absolute (3 bytes); indexed absolute (3 bytes); indexed zero-page (2 bytes); relative (2 bytes); accumulator (1); indirect,x and indirect,y (2); and immediate (2). Absolute mode is a general-purpose mode. Branch instructions use a signed 8-bit offset relative to the instruction after the branch; the numerical range −128.127 therefore translates to 128 bytes backward and 127 bytes forward from the instruction following the branch (which is 126 bytes backward and 129 bytes forward from the start of the branch instruction). Accumulator mode uses the accumulator as an effective address, and did not need any operand data. Immediate mode uses an 8-bit literal operand. The indirect modes are useful for array processing and other looping. With the ⅚ cycle "(indirect),y" mode, the 8-bit Y register is added to a 16-bit base address in zero page, located by a single byte following the opcode. As the resulting address could be anywhere in the 16-bit memory range, the Y register is a true index register, as opposed to the 6800, which had one 16-bit address register. Incrementing the index register to walk the array byte-wise took only two additional cycles. With the less frequently used "(indirect,x)" mode the effective address for the operation is found at the zero page address formed by adding the second byte of the instruction to the contents of the X register. Using the indexed modes, the zero page effectively acted as a set of 128 additional (though very slow) address registers. The 6502 also includes a set of binary coded decimal (BCD) instructions, a feature normally implemented in software. Placing the CPU into BCD allowed numbers to be manipulated in base-10, with a set of conversion instructions to convert between base-10 and binary (base-2). For instance, with the "D" flag set, 99+1 do result in 00 and the carry flag being set. These instructions remove the need to convert numbers for display in the BASIC interpreter itself. However, this feature means other useful instructions can not be implemented easily, and is sometimes removed to make room for custom instructions. The RSC 6502 microcontroller is merely one example of microcontroller, processor or microprocessor that can be used in the voice-recognition apparatus 3300. The RSC 6502 microcontroller has been manufactured by Conexant Systems at 4000 MacArthur Boulevard, Newport Beach, Calif.

The microcontroller, processor or microprocessor 3302 is operably coupled to a voice-recognition apparatus 3300 includes at least one input device, such as one of the devices shown in FIG. 6 including a keyboard, a synaptic reader, and/or a microphone 3304 such as shown in FIG. 33.

And some implementations, the microcontroller, processor or microprocessor 3302 is operably coupled to a program/run switch 3306 that is set to indicate the mode that the microcontroller, processor or microprocessor 3302 is operating. When the microcontroller, processor or microprocessor 3302 is being programmed, the program/run switch 3306 is set to program. When the microcontroller, processor or microprocessor 3302 is being run, the program/run switch 3306 is set to run.

The microcontroller, processor or microprocessor 3302 is operably coupled to a power input 3306.

In some implementations, the microcontroller, processor or microprocessor 3302 is operably coupled to a memory 3310 that stores data and programs. In some implementations the 3310 is a nonvolatile memory. In some implementations, the microcontroller, processor or microprocessor 3302 is operably coupled to a digital-to-analog (DAC) converter that generates DAC output 3312. In some implementations, the microcontroller, processor or microprocessor 3302 is operably coupled to an audio speaker 3314.

In other implementations, the microcontroller, processor or microprocessor 3302 includes memory. In some implementations in which the microcontroller, processor or microprocessor 3302 includes memory, a microprocessor/microcontroller/processor provides an economical wireless voice control and communications system. The microprocessor/microcontroller/processor incorporates voice recognition, infrared (IR) and radio frequency (RF) wireless protocols including Zigbee and Bluetooth wireless protocols with positional awareness and a complex programmable logic device (CPLD) interface. The microprocessor/microcontroller/processor communicates with and controls multi-sensory controls for electrical device(s) 114 from microwaves and washing machines to spacecraft. The microprocessor/microcontroller/processors are selected from both 16-bit and 32-bit devices. The microprocessor/microcontroller/processor having 16-bit radio-frequency (RF) interfaces are well-suited for applications such as wireless keyboard/mouse, wireless voice-over-IP (VoIP), remote controls, wireless gaming accessories, home and building automation applications such as alarm and security systems, automatic meter reading systems, active radio-frequency identification (RFID) systems and other monitoring and control systems.

Microprocessor/microcontroller/processors having 32-bit word-length include high performance integrated peripherals designed for real-time control applications. An optimized core of the microprocessor/microcontroller/processor performs multiple complex control algorithms at speeds necessary for demanding control applications. Integrated peripherals such as a 16-channel, 12-bit analog-to-digital conversion (ADC) running at up to 12.5 megasamples per second and high resolution pulse-width modulation (PWM) modules with 150 picosecond resolution provide sufficient bandwidth for communication with analog devices. Further including the serial peripheral interface (SPI), universal asynchronous receiver/transmitter (UART), inter-IC (I2C), campus area network (CAN), and multi-channel buffered serial port (McBSP) communication peripherals provides device control on a single microprocessor/microcontroller/processor. Applications include appliances, alternating current/direct current (AC/DC), direct current/alternating (DC/AC) and direct current/direct current (DC/DC) digital power supplies, solar inverters, digital motor control, and power line communication.

Figure 35:
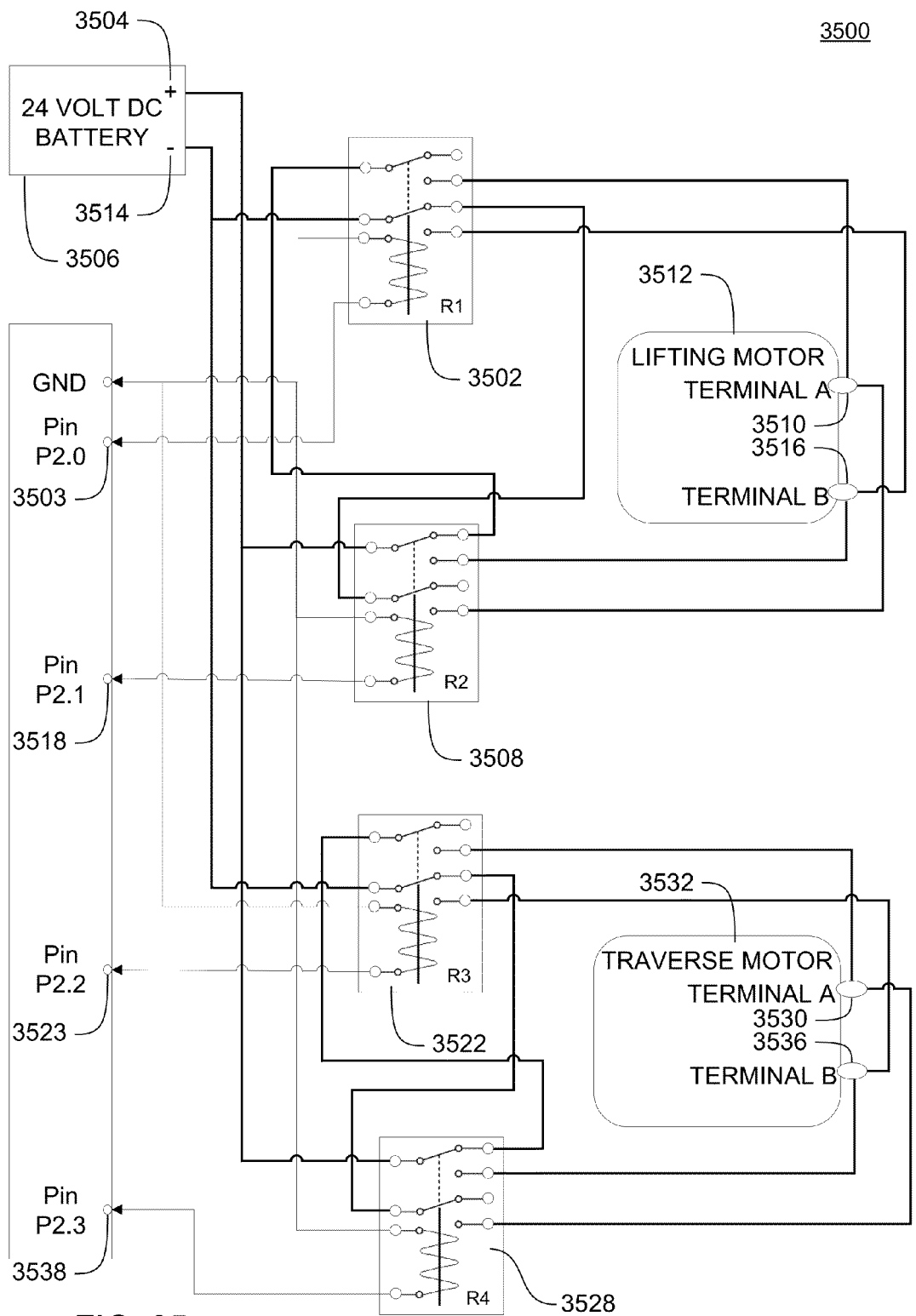
FIG. 35 is a block diagram of a device-controller of a patient-lifting-device, according to an implementation using DPTD relays.

The microcontroller, processor or microprocessor 3302 is operably coupled to a lift device-controller 3316 that can perform action 2304 in FIG. 23, actions 2402, 2404 and 2406 in FIG. 24, actions 2502, 2504 and 2506 in FIG. 25 and action 2602 in FIG. 26. The lift device-controller 3316 is electrically coupled to at least one patient-lifting-apparatus 3318. Examples of the patient-lifting-apparatus 3318 include the two dimensional patient-lifting-device 4400 in FIG. 44 and the one dimensional patient-lifting-device 4500 in FIG. 45. Device-controller 3500 in FIG. 35 is one implementation of the lift device-controller 3316 for a two dimensional patient-lifting-device, such as two dimensional patient-lifting-device 4400 in FIG. 44, that implements a double-pole-double-throw (DPDT) relay for each direction of movement of the two dimensional patient-lifting-device.

In some implementations, the microcontroller, processor or microprocessor 3302 is operably coupled to a serial port 3320 through which program instructions can be loaded onto the microcontroller, processor or microprocessor 3302.

In some implementations, the microcontroller, processor or microprocessor 3302 is operably coupled to a nonvolatile memory that stores a voice-recognition engine, such as voice-recognition engine 1600 in FIG. 16. In the implementation shown in FIG. 33, the nonvolatile memory is electrically erasable programmable read only memory (EEPROM) 3322. The voice-recognition engine 3322 includes a predefined set of functions that are called during voice-recognition operations.

FIG. 34 is an electrical schematic diagram of a voice-recognition apparatus 3400 to control a patient-lifting-apparatus, according to an implementation. The voice-recognition apparatus 3400 is one implementation of voice-recognition unit 804 in FIG. 8. The voice-recognition apparatus 3400 receives input from any one of a number of input mediums, including audio, and therefrom controls a patient-lifting-apparatus. The voice-recognition apparatus 3400 can fit inside the housing of conventional patient-lifting-apparatus and can communicate with and control the conventional patient-lifting-apparatus using the conventional existing electrical circuitry of patient-lifting-apparatus. The voice-recognition apparatus 3400 helps improve control of the patient-lifting-apparatus by receiving input from any one of a number of input mediums, including audio. In the example of audio, the voice-recognition apparatus 3400 improves the ease and convenience with which an operator can control the patient-lifting-apparatus by providing a voice interface to the patient-lifting-apparatus. In general, the voice-recognition apparatus 3400 improves the ease and convenience with which an operator can control the patient-lifting-apparatus by providing a command interface to the patient-lifting-apparatus other than a handheld control device, such as the handheld control device 4426 shown in FIG. 44.

Voice-recognition apparatus 3400 includes a microcontroller, processor or microprocessor 3402, such as a RSC 6502 microcontroller. The microcontroller, processor or microprocessor 3402 includes non-volatile memory (not shown) such as Flash memory that can be electrically erased and reprogrammed. The RSC 6502 microcontroller is merely one example of a microcontroller, processor or microprocessor that can be used in the voice-recognition apparatus 3400. The RSC 6502 microcontroller has been manufactured by Conexant Systems at 4000 MacArthur Boulevard, Newport Beach, Calif.

The microcontroller, processor or microprocessor 3402 is operably coupled to at least one input device (not shown), such as one of the devices shown in FIG. 6 including a keyboard, a synaptic reader, and/or a microphone. And some implementations, the microcontroller, processor or microprocessor 3402 is operably coupled to a program/run switch (not shown) that is set to indicate the mode that the microcontroller, processor or microprocessor 3402 is operating.

In some implementations, the microcontroller, processor or microprocessor 3402 is operably coupled to another memory (not shown) that stores data and programs. In some implementations, the microcontroller, processor or microprocessor 3402 is operably coupled to a digital-to-analog (DAC) converter that generates DAC output (not shown). In some implementations, the microcontroller, processor or microprocessor 3402 is operably coupled to an audio speaker (not shown).

In some implementations, the microprocessor/microcontroller/processor incorporates infrared (IR) and radio frequency (RF) wireless protocols including Zigbee and Bluetooth wireless protocols with positional awareness and a complex programmable logic device (CPLD) interface. The microprocessor/microcontroller/processor communicates with and controls multi-sensory controls for electrical device (s) 114 from microwaves and washing machines to spacecraft. The microprocessor/microcontroller/processor is selected from both 16-bit and 32-bit devices. The microprocessor/microcontroller/processor having 16-bit radio-frequency (RF) interfaces are well-suited for applications such as wireless keyboard/mouse, wireless voice-over-IP (VoIP), remote controls, wireless gaming accessories, home and building automation applications such as alarm and security systems, automatic meter reading systems, active radio-frequency identification (RFID) systems and other monitoring and control systems. Microprocessor/microcontroller/processors having 32-bit word-length include high performance integrated peripherals designed for real-time control applications. An optimized core of the microprocessor/microcontroller/processor performs multiple complex control algorithms at speeds necessary for demanding control applications. Integrated peripherals such as a 16-channel, 12-bit analog-to-digital conversion (ADC) running at up to 12.5 megasamples per second and high resolution pulse-width modulation (PWM) modules with 150 picosecond resolution provide sufficient bandwidth for communication with analog devices. Further including the serial peripheral interface (SPI), universal asynchronous receiver/transmitter (UART), inter-IC (I2C), campus area network (CAN), and multi-channel buffered serial port (McBSP) communication peripherals provides device control on a single microprocessor/microcontroller/processor. Applications include appliances, alternating current/direct current (AC/DC), direct current/alternating (DC/AC) and direct current/direct current (DC/DC) digital power supplies, solar inverters, digital motor control, and power line communication.

The microcontroller, processor or microprocessor 3402 is operably coupled to a lift device-controller (not shown) that can perform action 2304 in FIG. 23, actions 2402, 2404 and 2406 in FIG. 24, actions 2502, 2504 and 2506 in FIG. 25 and action 2602 in FIG. 26. The lift device-controller is electrically coupled to at least one patient-lifting-apparatus (not shown). Examples of the patient-lifting-apparatus (not shown) include the two dimensional patient-lifting-device 4400 in FIG. 44 and the one dimensional patient-lifting-device 4700 in FIG. 45. Device-controller 3500 in FIG. 35 is one implementation of the lift device-controller 3416 for a two dimensional patient-lifting-device, such as two dimensional patient-lifting-device 4400 in FIG. 44, that implements a double-pole-double-throw (DPDT) relay for each direction of movement of the two dimensional patient-lifting-device.

In some implementations, the microcontroller, processor or microprocessor 3402 is operably coupled to a serial port 3404 through which program instructions can be loaded onto the microcontroller, processor or microprocessor 3402.

In some implementations, the microcontroller, processor or microprocessor 3402 is operably coupled to a nonvolatile memory that stores a voice-recognition engine, such as voice-recognition engine 2400 in FIG. 24. In the implementation shown in FIG. 34, the nonvolatile memory is electrically erasable programmable read only memory (EEPROM) 3406. The voice-recognition engine 3406 includes a predefined set of functions that are called during voice-recognition operations.

FIG. 35 is a block diagram of a device-controller 3500 of a patient-lifting-device, according to an implementation using DPTD relays. Device-controller 3500 is one implementation of the lift device-controller 3316 in FIG. 33 for a two dimensional patient-lifting-device, such as two dimensional patient-lifting-device 4400 in FIG. 44, that implements a normally-open double-pole-double-throw (DPDT) relay for each direction of movement of the two dimensional patient-lifting-device. Two-dimensional movement consists of movement in four directions, hence device-controller 3500 consists of four normally-open DTDT relays. Other implementation of device-controller 3500 that do not have the safety features of device-controller 3500 implement single-pole-single-throw (SPST) relays.

To command movement in a particular direction, the corresponding relay is actuated. To actuate the patient-lifting-device in an upward direction, DPDT relay 3502 is actuated by setting voltage "high" (e.g. 3 volts) on pin "P2.0" 3503. When DPDT relay 3502 is actuated, the normally-open DPDT relay 3502 is closed, thereupon a positive electric current will flow from the positive terminal 3504 of the 24 volt DC battery 3506, through DPDT relay 3508, and through DPDT relay 3502 to Terminal A 3510 of lifting motor 3512 and also when DTDT relay 3502 is actuated, a negative electric current will flow from the negative terminal 3514 of the 24 volt DC battery 3506, through DPDT relay 3502 to Terminal B 3516 of lifting motor 3512, thus providing electric current to lifting motor 3512 in a polarity that will retract a line coupled to the lifting motor 3512, thereupon lifting the seat or hammock 4412.

To actuate the patient-lifting-device in a downward direction, DPDT relay 3508 is actuated by setting voltage "high" (e.g. 3 volts) on pin "P2.1" 3518. When DPDT relay 3508 is actuated, the normally-open DPDT relay 3508 becomes closed, thereupon a negative electric current will flow from the negative terminal 3514 of the 24 volt DC battery 3506, through DPDT relay 3502, and through DPDT relay 3508 to Terminal A 3510 of lifting motor 3512 and also when DTDT relay 3508 is actuated, a positive electric current will flow from the positive terminal 3504 of the 24 volt DC battery 3506, through DPDT relay 3508 to Terminal B 3516 of lifting motor 3512, thus providing electric current to lifting motor 3512 in a polarity that will extend a line coupled to the lifting motor 3512, thereupon lowering the seat or hammock 4412.

Please note the safety feature in the serial wiring of DTDT relay 3502 and DPDT relay 3508. The safety feature lies in that positive electric current will flow from the positive terminal 3504 of the 24 volt DC battery 3506, through DPDT relay 3508, and through DPDT relay 3502 to Terminal A 3510 of lifting motor 3512 when DPDT relay 3508 is not actuated. Positive electric current will not flow from the positive terminal 3504 of the 24 volt DC battery 3506, through DPDT relay 3508, and through DPDT relay 3502 to Terminal A 3510 of lifting motor 3512 when DPDT relay 3508 is actuated. Therefore, if somehow both DPDT relay 3502 and DPDT relay 3508 are simultaneously actuated, no current will flow to the lifting motor 3512, thus preventing both positive electric current and negative electric from simultaneously flowing to Terminal A 3510 of lifting motor 3512 and preventing both positive electric current and negative electric from simultaneously flowing to Terminal B 3516 of lifting motor 3512.

Other implementations use other power sources in place of the 24 volt DC battery 3506.

To actuate the patient-lifting-device in a forward traversal direction, DPDT relay 3522 is actuated by setting voltage "high" (e.g. 3 volts) on pin "P2.2" 3523. When DPDT relay 3522 is actuated, the normally-open DPDT relay 3522 is closed, thereupon a positive electric current will flow from the positive terminal 3504 of the 24 volt DC battery 3506, through DPDT relay 3528, and through DPDT relay 3522 to Terminal A 3530 of traversing motor 3532 and also when DTDT relay 3522 is actuated, a negative electric current will flow from the negative terminal 3534 of the 24 volt DC battery 3506, through DPDT relay 3522 to Terminal B 3536 of traversing motor 3532, thus providing electric current to traversing motor 3532 in a polarity that will traverse in a forward direction the line coupled to the traversing motor 3532, thereupon moving the seat or hammock 4412 forward.

To actuate the patient-lifting-device in a backward direction, DPDT relay 3528 is actuated by setting voltage "high" (e.g. 3 volts) on pin "P2.3" 3538. When DPDT relay 3528 is actuated, the normally-open DPDT relay 3528 becomes closed, thereupon a negative electric current will flow from the negative terminal 3534 of the 24 volt DC battery 3506, through DPDT relay 3522, and through DPDT relay 3528 to Terminal A 3530 of traversing motor 3532 and also when DTDT relay 3528 is actuated, a positive electric current will flow from the positive terminal 3504 of the 24 volt DC battery 3506, through DPDT relay 3528 to Terminal B 3536 of traversing motor 3532, thus providing electric current to traversing motor 3532 in a polarity that will traverse in a backward direction the line coupled to the traversing motor 3532, thereupon lowering the seat or hammock 4412.

Please note the safety feature in the serial wiring of DTDT relay 3522 and DPDT relay 3528. The safety feature lies in that positive electric current will flow from the positive terminal 3504 of the 24 volt DC battery 3506, through DPDT relay 3528, and through DPDT relay 3522 to Terminal A 3530 of traversing motor 3532 when DPDT relay 3528 is not actuated. Positive electric current will not flow from the positive terminal 3504 of the 24 volt DC battery 3506, through DPDT relay 3528, and through DPDT relay 3522 to Terminal A 3530 of traversing motor 3532 when DPDT relay 3528 is actuated. Therefore, if somehow both DPDT relay 3522 and DPDT relay 3528 are simultaneously actuated, no current will flow to the traversing motor 3532, thus preventing both positive electric current and negative electric from simultaneously flowing to Terminal A 3530 of traversing motor 3532 and preventing both positive electric current and negative electric from simultaneously flowing to Terminal B 3536 of traversing motor 3532.

A DPDT relay consists of two separate switches that operate at the same time, each one with normally open and normally closed contact through a common connector. Each of the two contacts on the switch can be routed in different ways, depending on the position of the switch. An example of a switch is a mini-toggle switch or a switch using a push or pull control.

DPDT relay switches commonly use polarity reversal. That is why some variations of the DPDT relay, such as the cross-over switches, are internally wired for that purpose. The cross-over switches have only four terminals or connections, as opposed to six on a DPDT relay. Two connections are used for the outputs and the other two for the inputs. The switch then selects either normal or reversed polarity when connected to any direct current source such as a battery.

A DPDT relay has a single coil with two arms that move simultaneously. Inside of the DPDT relay, there are two separate single-pole-double-throw (SPDT) switch mechanisms.

FIG. 36 is an electrical schematic diagram of a voice and manual controlled switch 3600, according to an implementation. The voice controlled and manual controlled wall switch 3600 is suitable for use in a small appliance or light switch. Microphone 3602 inputs sound information into audio circuit 3604 which in turn communicates the sound information to the voice recognition module 3606. Voice recognition module 3606 monitors the input sound information with pattern recognition to identify trigger phrases. Once a trigger phrase is identified voice recognition module 3606 enters a command recognition mode for a pre-determined time. During the command recognition mode, the voice recognition module 3606 monitors the input sound information with pattern recognition processes to identify commands such as "on", "light on", "off", "light off" or other user specified commands. If voice recognition module 3606 identifies a command phrase then the voice recognition module 3600 compares the value of the command phrase to the value of the previously received command phrase or a default value (off) if no previous command phrase is recorded. If the value of the command phrase differs from the previously received command phrase than the energized state of terminal 3608 is reversed such as reversing the energized stay of transistor 3610 and in turn reversing the state of single-pole double-throw relay 3612.

Some implementations of the voice and manual controlled switch 3600 also include a manual switch that controls the on/off operation of the voice and manual controlled switch 3600. Some implementations of the voice and manual controlled switch 3600 also include a speaker 3616 that enunciates audio notifications in regards to the operations of the voice and manual controlled switch 3600.

FIG. 37 is a mechanical diagram of a voice and manual controlled switch 3700, according to an implementation. The voice controlled and manual controlled wall switch 3700 is suitable for use in a small appliance or light switch. Microphone 3602 receives sound information into audio circuit 3604 in FIG. 36 which in turn communicates the sound information to the voice recognition module 3606 in FIG. 36. Some implementations of the voice and manual controlled switch 3700 also include a manual switch that controls the on/off operation of the voice and manual controlled switch 3700. Some implementations of the voice and manual controlled switch 3600 also include a speaker 3616 that enunciates audio notifications in regards to the operations of the voice and manual controlled switch 3700.

Figure 38:
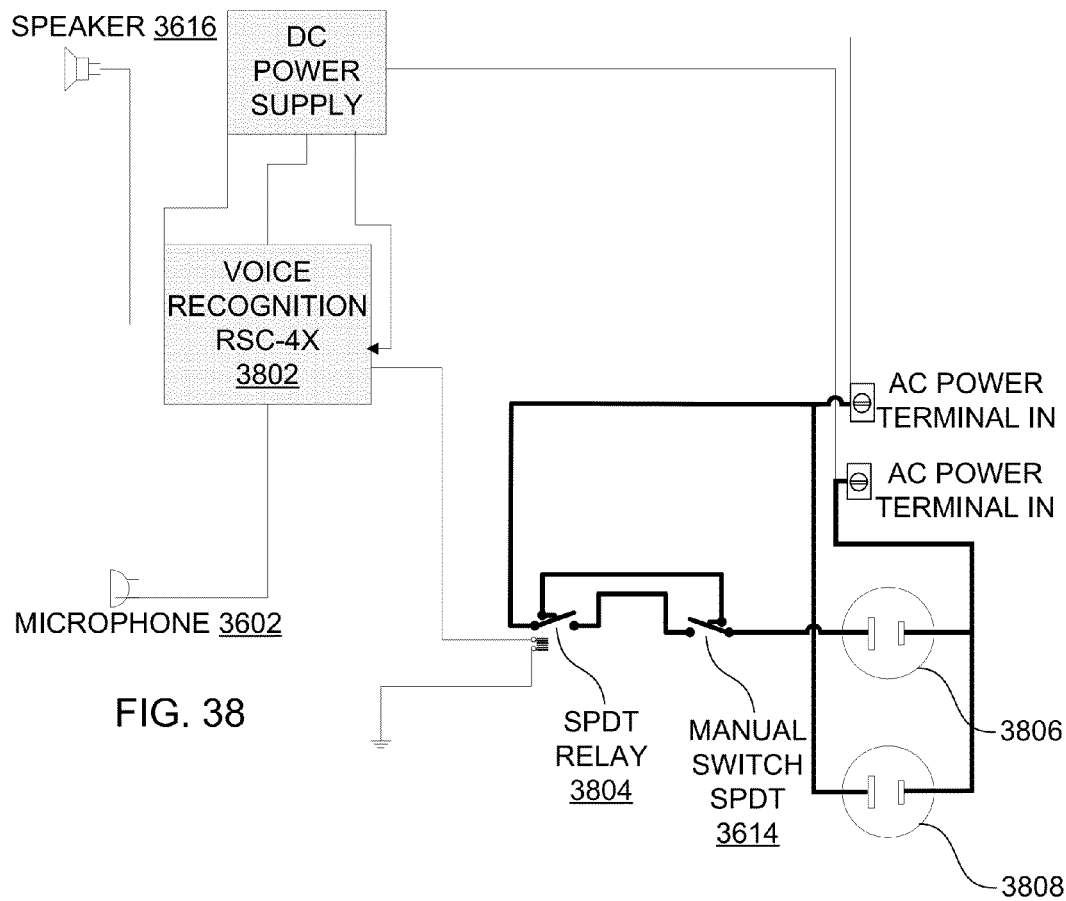
FIG. 38 is an electrical schematic diagram of a voice controlled wall plug with manual invoice controlled circuitry, according to an implementation.

FIG. 38 is an electrical schematic diagram of a voice controlled wall plug 3800 with manual invoice controlled circuitry, according to an implementation. The voice controlled and manual controlled wall switch 3800 is suitable for use in a small appliance or light switch. Microphone 3602 inputs sound information into audio circuit 3604 which in turn communicates the sound information to the voice recognition module RSC-4X 3802. Voice recognition module RSC-4X 3802 monitors the input sound information with pattern recognition to identify trigger phrases. Once a trigger phrase is identified voice recognition module RSC-4X 3802 enters a command recognition mode for a pre-determined time. During the command recognition mode, the voice recognition module RSC-4X 3802 monitors the input sound information with pattern recognition processes to identify commands such as "on", "light on", "off", "light off" or other user specified commands. If voice recognition module RSC-4X 3802 identifies a command phrase then the voice recognition module 360 compares the value of the command phrase to the value of the previously received command phrase or a default value (off) if no previous command phrase is recorded. If the value of the command phrase differs from the previously received command phrase than the energized state of terminal 3608 is reversed such as reversing the energized stay of transistor 3610 and in turn reversing the state of a single-pole double-throw (SPDT) relay 3804. One implementation of the SPDT relay 3804 is a G5LE-1-E-DD5 SPDT 120V-16A 5V coil.

The voice and manual controlled switch 3800 also includes one or more wall outlet plug(s) 3806 and 3808. In implementations that include a plurality of wall out plugs, the plugs are operably coupled in parallel, such as shown in FIG. 38.

Some implementations of the voice and manual controlled switch 3800 also include a manual switch that controls the on/off operation of the voice and manual controlled switch 3800. Some implementations of the voice and manual controlled switch 3800 also include a speaker 3616 that enunciates audio notifications in regards to the operations of the voice and manual controlled switch 3800.

Figure 39:
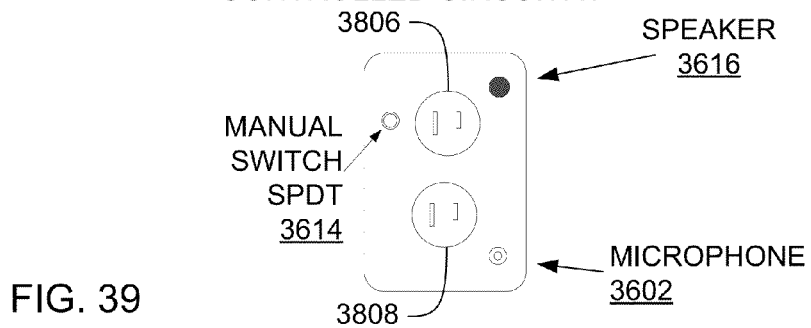
FIG. 39 is a mechanical diagram of a voice controlled wall plug with manual invoice controlled circuitry, according to an implementation.

FIG. 39 is a mechanical diagram of a voice controlled wall plug 3900 with manual invoice controlled circuitry, according to an implementation. The voice controlled and manual controlled wall switch 3900 is suitable for use in a small appliance or light switch. Microphone 3602 receives sound information into audio circuit 3604 in FIG. 38 which in turn communicates the sound information to the voice recognition module RSC-4X 3802 in FIG. 39. Some implementations of the voice and manual controlled switch 3900 also include a manual switch that controls the on/off operation of the voice and manual controlled switch 3900. Some implementations of the voice and manual controlled switch 3800 also include a speaker 3616 that enunciates audio notifications in regards to the operations of the voice and manual controlled switch 3900.

Figure 40:
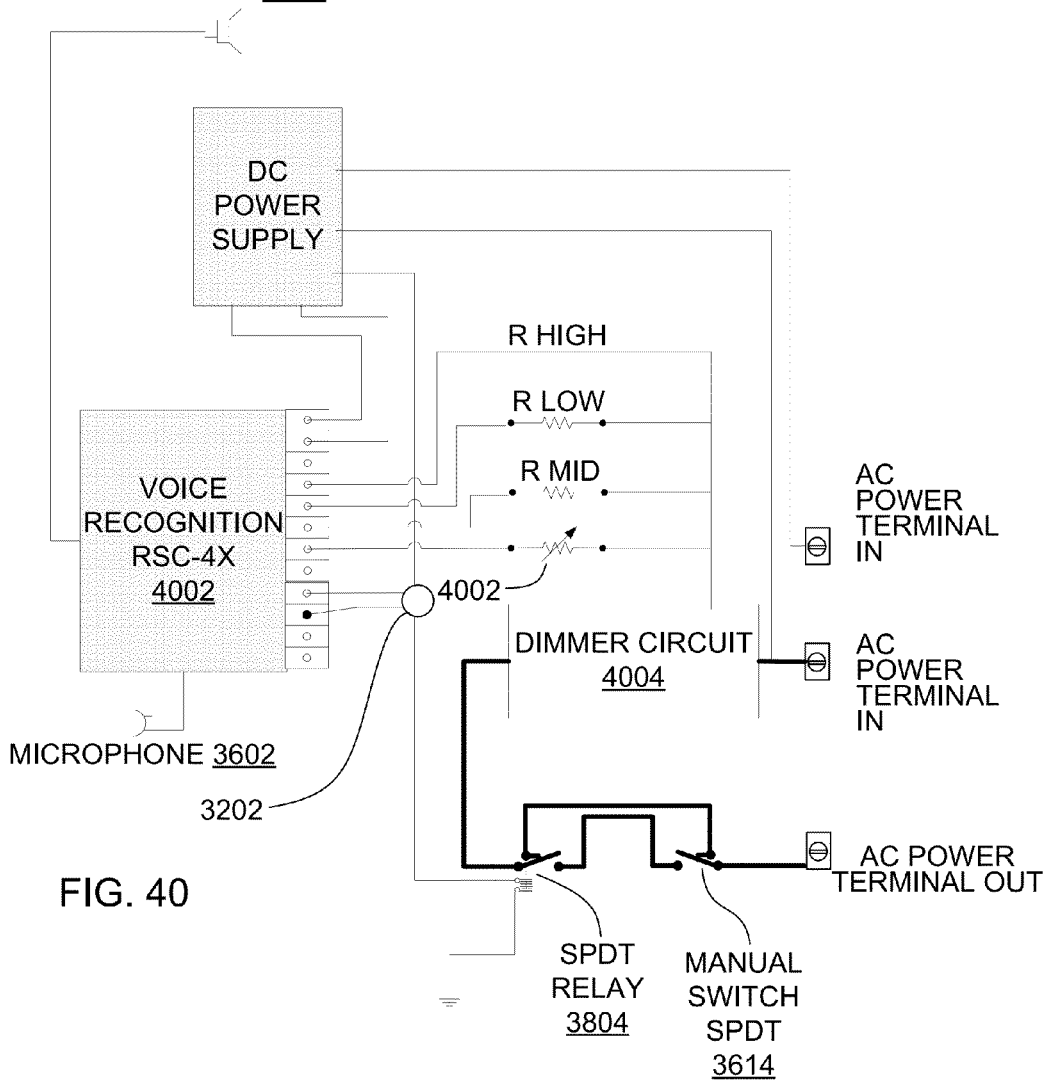
FIG. 40 is an electrical schematic diagram of a voice and manual controlled light switch with manual and invoice controlled dimmer circuitry, according to an implementation.

FIG. 40 is an electrical schematic diagram of a voice and manual controlled light switch 4000 with manual and invoice controlled dimmer circuitry, according to an implementation. The voice controlled and manual controlled wall switch 4000 is suitable for use in a small appliance or light switch. Microphone 3602 inputs sound information into audio circuit 3604 which in turn communicates the sound information to the voice recognition module RSC-4X 3802. Voice recognition module RSC-4X 3802 monitors the input sound information with pattern recognition to identify trigger phrases. Once a trigger phrase is identified voice recognition module RSC-4X 3802 enters a command recognition mode for a pre-determined time. During the command recognition mode, the voice recognition module RSC-4X 3802 monitors the input sound information with pattern recognition processes to identify commands such as "on", "light on", "off", "light off" or other user specified commands. If voice recognition module RSC-4X 3802 identifies a command phrase then the voice recognition module 4000 compares the value of the command phrase to the value of the previously received command phrase or a default value (off) if no previous command phrase is recorded. If the value of the command phrase differs from the previously received command phrase than the energized state of terminal 3608 is reversed such as reversing the energized stay of transistor 3610 and in turn reversing the state of single-pole double-throw relay 3804. One implementation of the SPDT relay 3804 is a G5LE-1-E-DD5 SPDT 120V-16A 5V coil. The voice recognition module RSC-4X 3802 is operably coupled to, and controls, a variable resistor 4002 that is operably coupled to, and controls, a dimmer circuit 4004.

Some implementations of the voice and manual controlled switch 4000 also include a manual switch that controls the on/off operation of the voice and manual controlled switch 4000. Some implementations of the voice and manual controlled switch 4000 also include a speaker 3616 that enunciates audio notifications in regards to the operations of the voice and manual controlled switch 4000.

Figure 41:
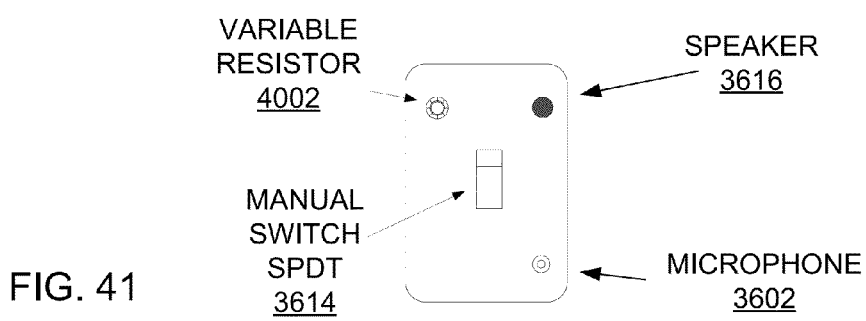
FIG. 41 is a mechanical diagram of a voice and manual controlled light switch with manual and invoice controlled dimmer circuitry, according to an implementation.

FIG. 41 is a mechanical diagram of a voice and manual controlled light switch 4100 with manual and invoice controlled dimmer circuitry, according to an implementation. The voice controlled and manual controlled wall switch 4100 is suitable for use in a small appliance or light switch. Microphone 3602 receives sound information into audio circuit 3604 in FIG. 38 which in turn communicates the sound information to the voice recognition module RSC-4X 3802 in FIG. 40. Some implementations of the voice and manual controlled switch 4100 also include a manual switch that controls the on/off operation of the voice and manual controlled switch 4100. Some implementations of the voice and manual controlled switch 4000 also include a speaker 3616 that enunciates audio notifications in regards to the operations of the voice and manual controlled switch 4100.

Figure 42:
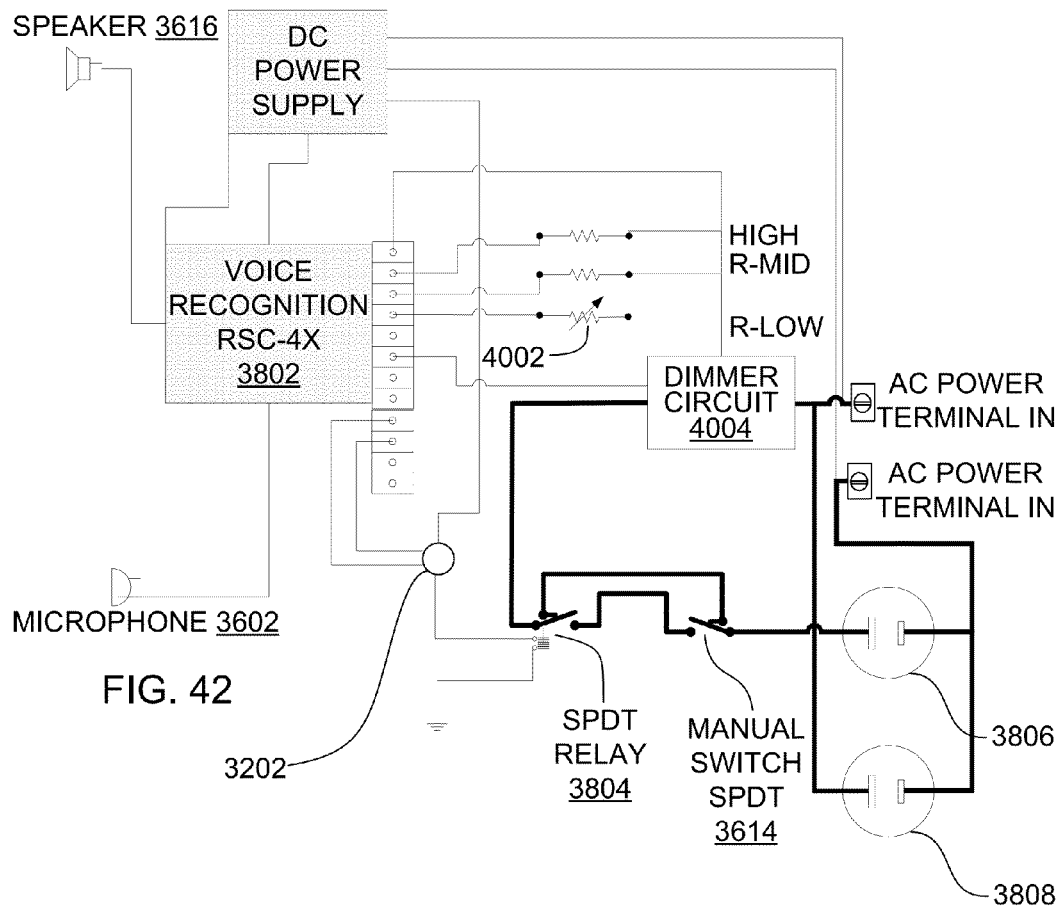
FIG. 42 is an electrical schematic diagram of a voice controlled wall plug with manual and voice controlled dimmer circuitry, according to an implementation.

FIG. 42 is an electrical schematic diagram of a voice controlled wall plug 4200 with manual and voice controlled dimmer circuitry, according to an implementation. The voice controlled and manual controlled wall switch 4200 is suitable for use in a small appliance or light switch. Microphone 3602 inputs sound information into audio circuit 3604 which in turn communicates the sound information to the voice recognition module RSC-4X 3802. Voice recognition module RSC-4X 3802 monitors the input sound information with pattern recognition to identify trigger phrases. Once a trigger phrase is identified voice recognition module RSC-4X 3802 enters a command recognition mode for a pre-determined time. During the command recognition mode, the voice recognition module RSC-4X 3802 monitors the input sound information with pattern recognition processes to identify commands such as "on", "light on", "off", "light off" or other user specified commands. If voice recognition module RSC-4X 3802 identifies a command phrase then the voice recognition module 4200 compares the value of the command phrase to the value of the previously received command phrase or a default value (off) if no previous command phrase is recorded. If the value of the command phrase differs from the previously received command phrase than the energized state of terminal 3608 is reversed such as reversing the energized stay of transistor 3610 and in turn reversing the state of single-pole double-throw relay 3804. One implementation of the SPDT relay 3804 is a G5LE-1-E-DD5 SPDT 120V-16A 5V coil. The voice recognition module RSC-4X 3802 is operably coupled to, and controls, a variable resistor 4002 that is operably coupled to, and controls, a dimmer circuit 4004.

The voice controlled wall plug 4200 also includes one or more wall outlet plug(s) 3806 and 3808. In implementations that include a plurality of wall out plugs, the plugs are operably coupled in parallel, such as shown in FIG. 42.

Some implementations of the voice and manual controlled switch 4300 also include a manual switch that controls the on/off operation of the voice and manual controlled switch 4200. Some implementations of the voice and manual controlled switch 4200 also include a speaker 3616 that enunciates audio notifications in regards to the operations of the voice and manual controlled switch 4200.

Figure 43:
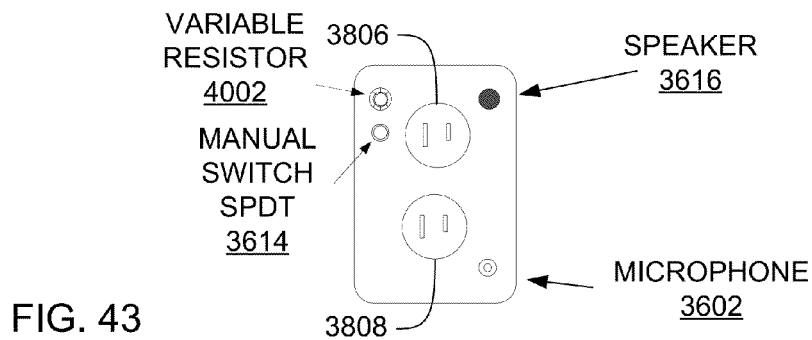
FIG. 43 is a mechanical diagram of a voice controlled wall plug with manual and voice controlled dimmer circuitry, according to an implementation.

FIG. 43 is a mechanical diagram of a voice controlled wall plug 4300 with manual and voice controlled dimmer circuitry, according to an implementation. The voice controlled and manual controlled wall switch 4300 is suitable for use in a small appliance or light switch. Microphone 3602 receives sound information into audio circuit 3604 in FIG. 42 which in turn communicates the sound information to the voice recognition module RSC-4X 3802 in FIG. 42. Some implementations of the voice and manual controlled switch 4300 also include a manual switch that controls the on/off operation of the voice and manual controlled switch 4300. Some implementations of the voice and manual controlled switch 4300 also include a speaker 3616 that enunciates audio notifications in regards to the operations of the voice and manual controlled switch 4300.

FIG. 44 is a block diagram of a two dimensional patient-lifting-device 4400, according to an implementation that is specifically adapted for lifting a patient out of bed. Patient-lifting-device 4400 includes vertical main supports 4402 and 4404 that are optionally supported by wheels 4406 and 4408 for movement on the ground. Patient-lifting-device 4400 also includes a horizontal support 4410 that is fixedly attached to the vertical main supports 4402 and 4404. In the implementation shown in FIG. 44, a seat or hammock 4412 is attached to the horizontal support 4410 via lines 4414, 4416, 4418 and 4420, although other implementations of the seat or hammock 4412 are well-known. An electric or hydraulic control box 4422 is slidably attached to the horizontal support 4410 through a rail (not shown) and the lines 4414, 4416, 4418 and 4420 are attached to the control box 4422 through a line 4424. The control box 4422 causes the line 4424 to be extended or retracted. A patient is placed in the seat or hammock 4412 for movement. As the line 4424 is extended, the horizontal support 4410 is lowered upward, thus causing the patient in the hammock or seat 4412 to move downward. As the traversal arm 4412 is retracted, the line 4424 is moved upward, thus causing the patient in the hammock or seat 4412 to move upwards. In addition the control box 4422 is operable to move horizontally along the horizontal support 4410.

In some implementations, the control box 4422 includes the various apparatus and systems described in this application that provide control of the patient-lifting-device 4400 from various stimulus such as audio voice input. Examples of the various apparatus and systems that are included in the control box 4422 include the command interface unit 102, processor 106 and/or device controller 110 in FIG. 1 and FIG. 2, the keyboard data receiver 602, voice data receiver 604 and/or a synaptic data receiver 606 in FIG. 6, the microphone 802 and or voice-recognition unit 804 in FIG. 8, the device configuration user interface 902 and/or the modifiable logic circuit 904 in FIG. 9, the electrical devices in FIG. 33-37, and other tangible systems that perform methods 1700, 1800, 1900, 2000, 2100, 2200, 2300, 2400, 2500 and/or 2600.

In some implementations, two dimensional patient-lifting-device 4400 includes a handheld control device 4426 that is electrically coupled to the control box 4422 via a line 4428, the handheld control device providing signals that directs movement of the line 4424 and movement of the control box 4422 along the horizontal support 4410. In some implementations, control initiated from the handheld control device 4426 overrides control initiated from other input means.

Some implementations of the two dimensional patient-lifting-device 4400 include a charging unit (not shown) in the horizontal support 4410 and/or the control box 4422 to provide power for recharging a battery. The battery can be mounted either in the control box 4422 or the horizontal support 4410. The charging unit is electrically coupled to a power cord having male prongs on the other end from the charging unit that are suitable to plug into a standard residential electrical wall outlet female receptacle.

Some implementations of the two dimensional patient-lifting-device 4400 are a portable lift that fits in doorways.

FIG. 45 is a block diagram of a one dimensional patient-lifting-device 4500, according to an implementation that is specifically adapted for lifting a patient in and out of a pool. Patient-lifting-device 4500 includes a vertical main support 4502 that is anchored or otherwise firmly attached to the ground 4504. Patient-lifting-device 4500 also includes a lifting arm 4506 that is rotatably attached to the vertical main support 4502. A seat or hammock 4508 is attached to the lifting arm 4506 via a line 4510. A patient is placed in the seat or hammock 4508 for movement. A traversal arm 4512 is rotatably attached to the vertical main support 4502 through a rotatable joint 4514. The traversal arm 4512 is also rotatably and slideably coupled to the lifting arm 4506 through joint 4516. An electric or hydraulic actuator 4518 is attached to the traversal arm 4512. The actuator 4518 causes the traversal arm 4512 to be extended or retracted. As the traversal arm 4512 is extended, the lifting arm 4506 is pushed upward, thus moving the patient in the hammock or seat 4508 to move upwards. As the traversal arm 4412 is retracted, the lifting arm 4506 is moved downward, thus moving the patient in the hammock or seat 4508 to move downwards.

The patient-lifting-device 4500 also includes a control box 4520. In some implementations such as shown in FIG. 45, the control box 4520 is mounted to the vertical main support 4502 although in other implementations the control box 4520 is located elsewhere. In some implementations such as shown in FIG. 45, the control box 4520 includes the various apparatus and systems described elsewhere in this application that provide control of the patient-lifting-device 4500 are various stimulus such as audio voice input. Examples of the various apparatus and systems that are included in the control box 4520 include the command interface unit 102, processor 106 and/or device controller 110 in FIG. 1 and FIG. 2, the keyboard data receiver 602, voice data receiver 604 and/or a synaptic data receiver 606 in FIG. 6, the microphone 802 and or voice-recognition unit 804 in FIG. 8, the device configuration user interface 902 and/or the modifiable logic circuit 904 in FIG. 9, the electrical devices in FIG. 33-37 and other tangible systems that perform methods 1700-3300.

FIG. 46 is a block diagram of a mobile device 4600, according to an implementation. The mobile device 4600 may also have the capability to allow voice communication. Depending on the functionality provided by the mobile device, it may be referred to as a data messaging device, a two-way pager, a cellular telephone with data messaging capabilities, a wireless Internet appliance, or a data communication device (with or without telephony capabilities).

Mobile device 4600 is one implementation of Bluetooth-capable cell phone 1420 in FIG. 14. The mobile device 4600 includes a number of components such as a main processor 4602 that controls the overall operation of the mobile device 4600. Communication functions, including data and voice communications, are performed through a communication subsystem 4604. The communication subsystem 4604 receives messages from and sends messages to wireless networks 4605. In other implementations of the mobile device 4600, the communication subsystem 4604 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 4604 with the wireless network 4605 represents one or more different Radio Frequency (RF) channels. With newer network protocols, these channels are capable of supporting both circuit switched voice communications and packet switched data communications.

The main processor 4602 also interacts with additional subsystems such as a Random Access Memory (RAM) 4606, a flash memory 4608, a display 4610, an auxiliary input/output (I/O) subsystem 4612, a data port 4614, a keyboard 4616, a speaker 4618, a microphone 4620, short-range communications 4622 and other device subsystems 4624. In some implementations, the flash memory 4608 includes a hybrid femtocell/Wi-Fi protocol stack 4609. The stack 4609 supports authentication and authorization between the mobile device 4600 into a shared Wi-Fi network and both a 3G and 4G mobile networks.

Some of the subsystems of the mobile device 4600 perform communication-related functions, whereas other subsystems may provide "resident" or on-device functions. By way of example, the display 4610 and the keyboard 4616 may be used for both communication-related functions, such as entering a text message for transmission over the wireless network 4605, and device-resident functions such as a calculator or task list.

The mobile device 4600 can transmit and receive communication signals over the wireless network 4605 after required network registration or activation procedures have been completed. Network access is associated with a subscriber or user of the mobile device 4600. To identify a subscriber, the mobile device 4600 requires a SIM/RUIM card 4626 (i.e. Subscriber Identity Module or a Removable User Identity Module) to be inserted into a SIM/RUIM interface 4628 in order to communicate with a network. The SIM card or RUIM 4626 is one type of a conventional "smart card" that can be used to identify a subscriber of the mobile device 4600 and to personalize the mobile device 4600, among other things.

Without the SIM card 4626, the mobile device 4600 is not fully operational for communication with the wireless network 4605. By inserting the SIM card/RUIM 4626 into the SIM/RUIM interface 4628, a subscriber can access all subscribed services. Services may include: web browsing and messaging such as e-mail, voice mail, Short Message Service (SMS), and Multimedia Messaging Services (MMS). More advanced services may include: point of sale, field service and sales force automation. The SIM card/RUIM 4626 includes a processor and memory for storing information. Once the SIM card/RUIM 4626 is inserted into the SIM/RUIM interface 4628, it is coupled to the main processor 4602. In order to identify the subscriber, the SIM card/RUIM 4626 can include some user parameters such as an International Mobile Subscriber Identity (IMSI). An advantage of using the SIM card/RUIM 4626 is that a subscriber is not necessarily bound by any single physical mobile device. The SIM card/RUIM 4626 may store additional subscriber information for a mobile device as well, including datebook (or calendar) information and recent call information. Alternatively, user identification information can also be programmed into the flash memory 4608.

The mobile device 4600 is a battery-powered device and includes a battery interface 4632 for receiving one or more rechargeable batteries 4630. In one or more implementations, the battery 4630 can be a smart battery with an embedded microprocessor. The battery interface 4632 is coupled to a regulator 4633, which assists the battery 4630 in providing power V+ to the mobile device 4600. Although current technology makes use of a battery, future technologies such as micro fuel cells may provide the power to the mobile device 4600.

The mobile device 4600 also includes an operating system 4634 and software components 4636 to 4646 which are described in more detail below. The operating system 4634 and the software components 4636 to 4646 that are executed by the main processor 4602 are typically stored in a persistent store such as the flash memory 4608, which may alternatively be a read-only memory (ROM) or similar storage element (not shown). Those skilled in the art will appreciate that portions of the operating system 4634 and the software components 4636 to 4646, such as specific device applications, or parts thereof, may be temporarily loaded into a volatile store such as the RAM 4606. Other software components can also be included.

The subset of software applications 4636 that control basic device operations, including data and voice communication applications, will normally be installed on the mobile device 4600 during its manufacture. Other software applications include a message application 4638 that can be any suitable software program that allows a user of the mobile device 4600 to transmit and receive electronic messages. Various alternatives exist for the message application 4638 as is well known to those skilled in the art. Messages that have been sent or received by the user are typically stored in the flash memory 4608 of the mobile device 4600 or some other suitable storage element in the mobile device 4600. In one or more implementations, some of the sent and received messages may be stored remotely from the device 4600 such as in a data store of an associated host system with which the mobile device 4600 communicates.

The software applications can further include a device state module 4640, a Personal Information Manager (PIM) 4642, and other suitable modules (not shown). The device state module 4640 provides persistence, i.e. the device state module 4640 ensures that important device data is stored in persistent memory, such as the flash memory 4608, so that the data is not lost when the mobile device 4600 is turned off or loses power.

The PIM 4642 includes functionality for organizing and managing data items of interest to the user, such as, but not limited to, e-mail, contacts, calendar events, voice mails, appointments, and task items. A PIM application has the ability to transmit and receive data items via the wireless network 4605. PIM data items may be seamlessly integrated, synchronized, and updated via the wireless network 4605 with the mobile device subscriber's corresponding data items stored and/or associated with a host computer system. This functionality creates a mirrored host computer on the mobile device 4600 with respect to such items. This can be particularly advantageous when the host computer system is the mobile device subscriber's office computer system.

The mobile device 4600 also includes a connect module 4644, and an IT policy module 4646. The connect module 4644 implements the communication protocols that are required for the mobile device 4600 to communicate with the wireless infrastructure and any host system, such as an enterprise system, with which the mobile device 4600 is authorized to interface. Examples of a wireless infrastructure and an enterprise system are given in FIGS. 21 and 22, which are described in more detail below.

The connect module 4644 includes a set of APIs that can be integrated with the mobile device 4600 to allow the mobile device 4600 to use any number of services associated with the enterprise system. The connect module 4644 allows the mobile device 4600 to establish an end-to-end secure, authenticated communication pipe with the host system. A subset of applications for which access is provided by the connect module 4644 can be used to pass IT policy commands from the host system to the mobile device 4600. This can be done in a wireless or wired manner. These instructions can then be passed to the IT policy module 4646 to modify the configuration of the device 4600. Alternatively, in some cases, the IT policy update can also be done over a wired connection.

The IT policy module 4646 receives IT policy data that encodes the IT policy. The IT policy module 4646 then ensures that the IT policy data is authenticated by the mobile device 4600. The IT policy data can then be stored in the flash memory 4606 in its native form. After the IT policy data is stored, a global notification can be sent by the IT policy module 4646 to all of the applications residing on the mobile device 4600. Applications for which the IT policy may be applicable then respond by reading the IT policy data to look for IT policy rules that are applicable.

The IT policy module 4646 can include a parser 4647, which can be used by the applications to read the IT policy rules. In some cases, another module or application can provide the parser. Grouped IT policy rules, described in more detail below, are retrieved as byte streams, which are then sent (recursively) into the parser to determine the values of each IT policy rule defined within the grouped IT policy rule. In one or more implementations, the IT policy module 4646 can determine which applications are affected by the IT policy data and transmit a notification to only those applications. In either of these cases, for applications that are not being executed by the main processor 4602 at the time of the notification, the applications can call the parser or the IT policy module 4646 when they are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 4646 sends an acknowledgement back to the host system to indicate that the IT policy data was received and successfully applied.

Other types of software applications can also be installed on the mobile device 4600. These software applications can be third party applications, which are added after the manufacture of the mobile device 4600. Examples of third party applications include games, calculators, utilities, etc.

The additional applications can be loaded onto the mobile device 4600 through at least one of the wireless network 4605, the auxiliary I/O subsystem 4612, the data port 4614, the short-range communications subsystem 4622, or any other suitable device subsystem 4624. This flexibility in application installation increases the functionality of the mobile device 4600 and may provide enhanced on-device functions, communication-related functions, or both. For example, secure communication applications may enable electronic commerce functions and other such financial transactions to be performed using the mobile device 4600.

The data port 4614 enables a subscriber to set preferences through an external device or software application and extends the capabilities of the mobile device 4600 by providing for information or software downloads to the mobile device 4600 other than through a wireless communication network. The alternate download path may, for example, be used to load an encryption key onto the mobile device 4600 through a direct and thus reliable and trusted connection to provide secure device communication.

The data port 4614 can be any suitable port that enables data communication between the mobile device 4600 and another computing device. The data port 4614 can be a serial or a parallel port. In some instances, the data port 4614 can be a USB port that includes data lines for data transfer and a supply line that can provide a charging current to charge the battery 4630 of the mobile device 4600.

The short-range communications subsystem 4622 provides for communication between the mobile device 4600 and different systems or devices, without the use of the wireless network 4605. For example, the subsystem 4622 may include an infrared device and associated circuits and components for short-range communication. Examples of short-range communication standards include standards developed by the Infrared Data Association (IrDA), Bluetooth, and the 802.11 family of standards developed by IEEE.

Bluetooth is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, Bluetooth was originally conceived as a wireless alternative to RS-232 data cables. It can connect several devices, overcoming problems of synchronization. Bluetooth operates in the range of 2400-2483.5 MHz (including guard bands), which is in the globally unlicensed Industrial, Scientific and Medical (ISM) 2.4 GHz short-range radio frequency band. Bluetooth uses a radio technology called frequency-hopping spread spectrum. The transmitted data is divided into packets and each packet is transmitted on one of the 79 designated Bluetooth channels. Each channel has a bandwidth of 1 MHz. The first channel starts at 2402 MHz and continues up to 2480 MHz in 1 MHz steps. It usually performs 1600 hops per second, with Adaptive Frequency-Hopping (AFH) enabled. Originally Gaussian frequency-shift keying (GFSK) modulation was the only modulation scheme available; subsequently, since the introduction of Bluetooth 2.0+EDR, π/4-DQPSK and 8DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe π/4-DPSK and 8DPSK schemes, each giving 2 and 3 Mbit/s respectively. The combination of these (BR and EDR) modes in Bluetooth radio technology is classified as a "BR/EDR radio". Bluetooth is a packet-based protocol with a master-slave structure. One master may communicate with up to 7 slaves in a piconet; all devices share the master's clock. Packet exchange is based on the basic clock, defined by the master, which ticks at 312.5 μs intervals. Two clock ticks make up a slot of 625 μs; two slots make up a slot pair of 1250 μs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone will necessarily begin as master, as initiator of the connection; but may subsequently prefer to be slave). The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, it switches rapidly from one device to another in a round-robin fashion. Since it is the master that chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth can expose private data or allow the connecting party to control the Bluetooth device. For security reasons it is necessary to be able to recognize specific devices and thus enable control over which devices are allowed to connect to a given Bluetooth device. At the same time, it is useful for Bluetooth devices to be able to establish a connection without user intervention (for example, as soon as they are in range). To resolve this conflict, Bluetooth uses a process called bonding, and a bond is created through a process called pairing. The pairing process is triggered either by a specific request from a user to create a bond (for example, the user explicitly requests to "Add a Bluetooth device"), or it is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices.

When desired, the bonding relationship can later be removed by the user. Secure Simple Pairing (SSP): This is required by Bluetooth v2.1, although a Bluetooth v2.1 device may only use legacy pairing to interoperate with a v2.0 or earlier device. Secure Simple Pairing uses a form of public key cryptography, and some types can help protect against man in the middle, or MITM attacks. SSP has the following characteristics: Just works: As implied by the name, this method just works. No user interaction is required; however, a device may prompt the user to confirm the pairing process. This method is typically used by headsets with very limited 10 capabilities, and is more secure than the fixed PIN mechanism which is typically used for legacy pairing by this set of limited devices. This method provides no man in the middle (MITM) protection. Numeric comparison: If both devices have a display and at least one can accept a binary Yes/No user input, they may use Numeric Comparison. This method displays a 6-digit numeric code on each device. The user should compare the numbers to ensure they are identical. If the comparison succeeds, the user(s) should confirm pairing on the device(s) that can accept an input. This method provides MITM protection, assuming the user confirms on both devices and actually performs the comparison properly. Passkey Entry: This method may be used between a device with a display and a device with numeric keypad entry (such as a keyboard), or two devices with numeric keypad entry. In the first case, the display is used to show a 6-digit numeric code to the user, who then enters the code on the keypad. In the second case, the user of each device enters the same 6-digit number. Both of these cases provide MITM protection. Out of band (OOB): This method uses an external means of communication, such as Near Field Communication (NFC) to exchange some information used in the pairing process. Pairing is completed using the Bluetooth radio, but requires information from the OOB mechanism. This provides only the level of MITM protection that is present in the OOB mechanism. SSP is considered simple for the following reasons: In most cases, it does not require a user to generate a passkey. For use-cases not requiring MITM protection, user interaction can be eliminated. For numeric comparison, MITM protection can be achieved with a simple equality comparison by the user. Using OOB with NFC enables pairing when devices simply get close, rather than requiring a lengthy discovery process.

In use, a received signal such as a text message, an e-mail message, or web page download will be processed by the communication subsystem 4604 and input to the main processor 4602. The main processor 4602 will then process the received signal for output to the display 4610 or alternatively to the auxiliary I/O subsystem 4612. A subscriber may also compose data items, such as e-mail messages, for example, using the keyboard 4616 in conjunction with the display 4610 and possibly the auxiliary I/O subsystem 4612. The auxiliary subsystem 4612 may include devices such as: a touch screen, mouse, track ball, infrared fingerprint detector, or a roller wheel with dynamic button pressing capability. The keyboard 4616 is preferably an alphanumeric keyboard and/or telephone-type keypad. However, other types of keyboards may also be used. A composed item may be transmitted over the wireless network 4605 through the communication subsystem 4604.

For voice communications, the overall operation of the mobile device 4600 is substantially similar, except that the received signals are output to the speaker 4618, and signals for transmission are generated by the microphone 4620. Alternative voice or audio I/O subsystems, such as a voice message recording subsystem, can also be implemented on the mobile device 4600. Although voice or audio signal output is accomplished primarily through the speaker 4618, the display 4610 can also be used to provide additional information such as the identity of a calling party, duration of a voice call, or other voice call related information.

Referring now to FIG. 47, a block diagram of the communication-subsystem component 4604 is shown, according to an implementation. The communication subsystem 4604 includes a receiver 4700, a transmitter 4702, as well as associated components such as one or more embedded or internal antenna elements 4704 and 4706, Local Oscillators (LOs) 4708, and a processing module such as a Digital Signal Processor (DSP) 4710. The particular implementation of the communication subsystem 4604 is dependent upon the communication wireless network 4605 with which the mobile device 4600 is intended to operate. Thus, it should be understood that the implementation illustrated in FIG. 47 serves only as one example.

Signals received by the antenna 4704 through the wireless network 4605 are input to the receiver 4700, which may perform such common receiver functions as signal amplification, frequency down conversion, filtering, channel selection, and analog-to-digital (A/D) conversion. A/D conversion of a received signal allows more complex communication functions such as demodulation and decoding to be performed in the DSP 4710. In a similar manner, signals to be transmitted are processed, including modulation and encoding, by the DSP 4710. These DSP-processed signals are input to the transmitter 4702 for digital-to-analog (D/A) conversion, frequency up conversion, filtering, amplification and transmission over the wireless network 4605 via the antenna 4706. The DSP 4710 not only processes communication signals, but also provides for receiver and transmitter control. For example, the gains applied to communication signals in the receiver 4700 and the transmitter 4702 may be adaptively controlled through automatic gain control algorithms implemented in the DSP 4710.

The wireless link between the mobile device 4600 and the wireless network 4605 can contain one or more different channels, typically different RF channels, and associated protocols used between the mobile device 4600 and the wireless network 4605. An RF channel is a limited resource that must be conserved, typically due to limits in overall bandwidth and limited battery power of the mobile device 4600.

When the mobile device 4600 is fully operational, the transmitter 4702 is typically keyed or turned on only when it is transmitting to the wireless network 4605 and is otherwise turned off to conserve resources. Similarly, the receiver 4700 is periodically turned off to conserve power until the receiver 4700 is needed to receive signals or information (if at all) during designated time periods.

Figure 48:
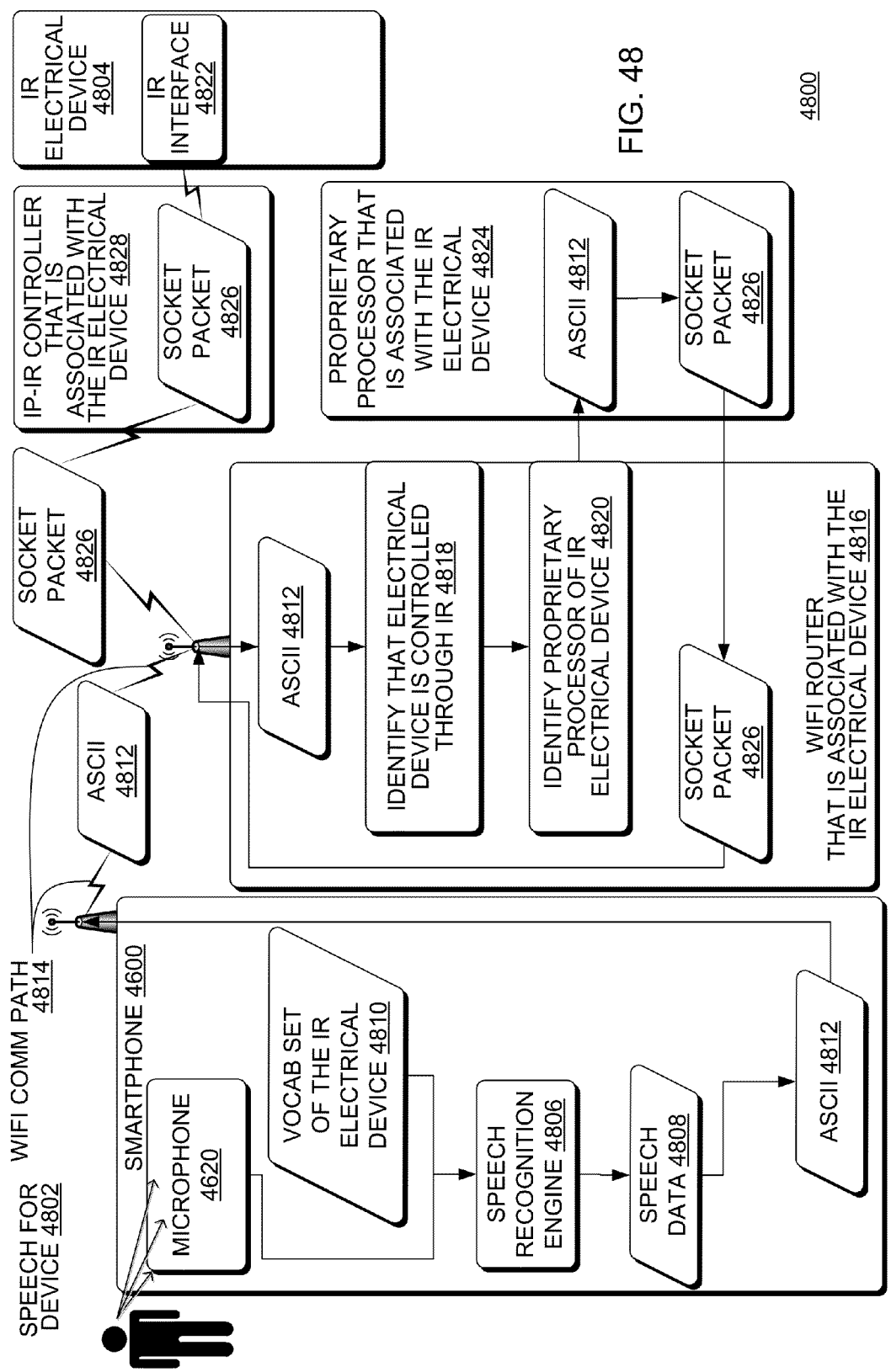
FIG. 48 is a block diagram of a system that is operable to control one or more controllable infrared electrical devices from audio speech, the system operable to control the at least one controllable infrared device through a wireless communication path, according to an implementation.

FIG. 48 is a block diagram of a system 4800 that is operable to control one or more controllable infrared electrical devices from audio speech, the system operable to control the at least one controllable infrared device through a wireless communication path, according to an implementation.

System 4800 includes a microphone 4620 of a wireless mobile device (smartphone) 4600 that is operable to receive audio speech 4802. The audio speech 4802 is associated with the IR controllable electrical device 4804. The IR controllable electrical device 4804 is an electrical device that is controllable via external infrared signal(s).

The wireless mobile device 4600 also includes a speech recognition engine 4806 that is operable to generate speech data 4808 that is associated with a vocabulary set 4810 of the IR controllable electrical device 4804 from the audio speech at the wireless mobile device 4600. The vocabulary set 4810 of the IR controllable electrical device 4804 is a set of vocabulary that includes speech patterns of trigger phrases that are relevant to the IR controllable electrical device 4804. Speech patterns of trigger phrases that are irrelevant to the IR controllable electrical device 4804 are not included in the vocabulary set 4810 of the IR controllable electrical device 4804. For example, when the IR controllable electrical device 4804 is a light, the vocabulary set 4810 of the IR controllable electrical device 4804 includes only trigger phrases "on", "light on", "off" and "light off", and the vocabulary set 4810 of the IR controllable electrical device 4804 excludes speech patterns of all other trigger phrases. In another example, when the IR controllable electrical device 4804 is a patient lift, the vocabulary set 4810 of the IR controllable electrical device 4804 includes only trigger phrases "lower down," "move down," "move forward," "forward," "move backward," "reverse," "goto sleep," "sleep," "faster," "slower," "left," "right," "up," "down," "forward," and "backward", and the vocabulary set 4810 of the IR controllable electrical device 4804 excludes speech patterns of all other trigger phrases. The wireless mobile device 4600 includes vocabulary sets (not shown) of other IR controllable electrical devices and controllable non-IR electrical devices, but the vocabulary set 4810 of the IR controllable electrical device 4804 is selected from among the vocabulary sets all of IR controllable electrical devices and controllable non-IR electrical devices for which the smartphone is configured to control through previous audio speech that identifies the IR controllable electrical device 4804. Having a vocabulary set 4810 in which the speech patterns of trigger phrases that are relevant to only the IR controllable electrical device 4804 is a much smaller vocabulary set than a vocabulary set that includes speech patterns of trigger phrases that are relevant to the other controllable electrical devices. The much smaller size of the vocabulary set 4810 of the IR controllable electrical device 4804 has the effect of greatly increasing the accuracy of the speech data 4808 that is generated by the speech recognition engine 4806, and greatly increases the speed of the speech recognition engine in the process of generating the speech data 4808. Based on the technology of processor and bus speeds of current smartphones, this is the most superior technique to accurately and quickly provide speech data 4808 that is relevant to the IR controllable electrical device 4804 from the audio speech 4802.

The IR controllable electrical device 4804 can be a IR controllable light, a IR controllable patient lift, a IR controllable television, a IR controllable television set-top box, a IR controllable radio, a IR controllable medication dispenser, a IR controllable bed, a IR controllable nurse call device, a IR controllable door, a IR controllable window cover, a IR controllable computer, a IR controllable medical therapeutic device, a IR controllable fan, a IR controllable, a IR controllable lamp, a IR controllable dishwasher, a IR controllable iron, a IR controllable production machinery, a IR controllable van ramp, a IR controllable cellphone or a IR controllable environmental control.

The wireless mobile device 4600 also includes a component (not shown) that is operable to convert the speech data 4808 to an ASCII string 4812. The ASCII string 4812 identifies the IR controllable electrical device 4804 and represents control data of the IR controllable electrical device 4804 that is indicated by the audio speech 4802.

The communication subsystem 4604 (shown in FIGS. 46 and 47) of the wireless mobile device 4600 establishes a WIFI communication path 4814 with a WIFI wireless router 4816. The WIFI wireless router 4816 is associated with the IR controllable electrical device 4804. The wireless mobile device 4600 is operable to transmit the ASCII string 4812 to the WIFI wireless router 4816 through the WIFI communication path 4814.

The WIFI wireless router 4816 is operable to receive the ASCII string 4812 through the WIFI communication path 4814. The ASCII string 4812 is stored in memory of the WIFI wireless router 4816. The WIFI wireless router 4816 includes a component 4818 that is operable to determine that the IR controllable electrical device 4804 of the ASCII string 4812 is controlled through an infrared interface 4822. The infrared interface 4822 through which the IR controllable electrical device 4804 is controlled is known as an associated infrared interface. The WIFI wireless router 4816 includes a component 4820 that is operable to identify a proprietary processor 4824 that is associated with the associated infrared interface 4822. The identified proprietary processor 4824 is known as an associated proprietary processor 4824. The WIFI wireless router 4816 is operable to transmit the ASCII string 4812 from the WIFI wireless router 4816 to the associated proprietary processor 4824. In some implementations, the WIFI wireless router 4816 and the proprietary processor 4824 are housed in a single housing. The proprietary processor 4824 can be a processor manufactured on a mass-production line that is modified for proprietary purposes described herein, in some implementations by coupling to proprietary processor 4824 to read-only-memory that has computer-readable instructions to perform the functions described herein, or in some implementations the proprietary processor 4824 is modified after mass production to perform the functions described herein, or in some implementations the proprietary processor 4824 is modified by loading a volatile memory of the proprietary processor 4824 with computer-readable instructions to perform the functions described herein.

The proprietary processor 4824 is operable to receive from the WIFI wireless router 4816 the ASCII string 4812 and to store the ASCII string 4812 in memory. The proprietary processor 4824 includes a component (not shown) that is operable to create a socket packet 4826 from the ASCII string 4812 at the associated proprietary processor 4824. The proprietary processor 4824 is operable to transmit the socket packet 4826 to the WIFI wireless router 4816 that is associated with the IR controllable electrical device 4804. The transmission includes a destination address, such as an IP address, of an IP-to-IR controller 4828 that is associated with the IR controllable electrical device 4804.

The WIFI wireless router 4816 that is associated with the IR controllable electrical device 4804 is operable to receive the socket packet 4826 and the destination address of the IR controllable electrical device 4804 from the proprietary processor 4824.

The WIFI wireless router 4816 that is associated with the IR controllable electrical device 4804 is operable to transmit the socket packet 4826 from the WIFI wireless router 4816 that is associated with the IR controllable electrical device 4804 to the IP-to-IR controller 4828 at the destination address.

The IP-to-IR controller 4828 is operable to receive the socket packet 4826 from the WIFI wireless router 4816 that is associated with the IR controllable electrical device 4804.

The IP-to-IR controller 4828 is operable to transmit via an infrared transmitter (not shown) an infrared signal in accordance with the socket packet 4826 to the infrared interface 4822 of the IR controllable electrical device 4804. One example for the IR codes for particular functions of a television is shown below in Table 1:

TABLE 1

| Function | IR CODE |
| --- | --- |
| Guide | 0x38C7 |
| AV | 0x8A75 |
| COMP | 0x5AA5 |
| HDMI | 0x639C |
| UP | 0xA25D |
| TV | 0x6B94 |
| LEFT | 0xE21D |
| DOWN | 0x629D |
| RIGHT | 0x12ED |
| MENU | 0xC23D |
| MUTE | 0x906F |
| LAST | 0x58A7 |
| VOL_UP | 0x40BF |
| VOL_DWN | 0xC03F |
| CH_UP | 0x00FF |
| CH_DWN | 0x807F |
| ONE | 0x8877 |
| TWO | 0x48B7 |
| THREE | 0xC837 |
| FOUR | 0x28D7 |
| FIVE | 0xA857 |
| SIX | 0x6897 |
| SEVEN | 0xE817 |
| EIGHT | 0x18E7 |
| NINE | 0x9867 |
| ZERO | 0x08F7 |
| INPUT | 0xF40B |
| DASH | 0xFF00 |
| POWER | 0x10EF |

The IR controllable electrical device 4804 is operable to receive the infrared signal at the infrared interface 4822 of the IR controllable electrical device and operable to perform a function in accordance with the infrared signal, providing control of the IR controllable electrical device 4804 in accordance with the audio speech 4802.

Routing the socket packet 4826 through the WIFI wireless router 4816 from the proprietary processor 4824 and to the IP-to-IR controller 4828 is particularly important because the IP-to-IR controller 4828 is required to be in line-of-sight to the IR controllable electrical device 4804 in order for the IR transmission between the IP-to-IR controller 4828 and the IR controllable electrical device 4804 to be effective, yet in systems where IR controllable electrical devices are located in different rooms and out of the line-of-sight, the RF communication of WIFI wireless router 4816 is necessary in order for the proprietary processor 4824 to communicate to the IR controllable electrical devices.

In some implementations, the destination IP address of the of IP-to-IR controller 4828 is encapsulated with socket packet 4826 inside a second socket packet (not shown). In some implementations, the destination IP address of the WIFI wireless router 4816 is encapsulated with the second socket packet inside a third socket packet (not shown).

An important feature of system 4800 is that the ASCII string 4812, the socket packet 4826 and the infrared signal all represent control data of the at least one controllable electrical device that is indicated by the audio speech. 4802. It is through this common representation by the ASCII string 4812, the socket packet 4826 and the infrared signal of the control data of the at least one controllable electrical device that is indicated by the audio speech 4802 that the audio speech is effectively communicated across heterogeneous electrical devices, starting at the smartphone 4600 and ending at the IR controllable electrical device 4804.

Figure 49:
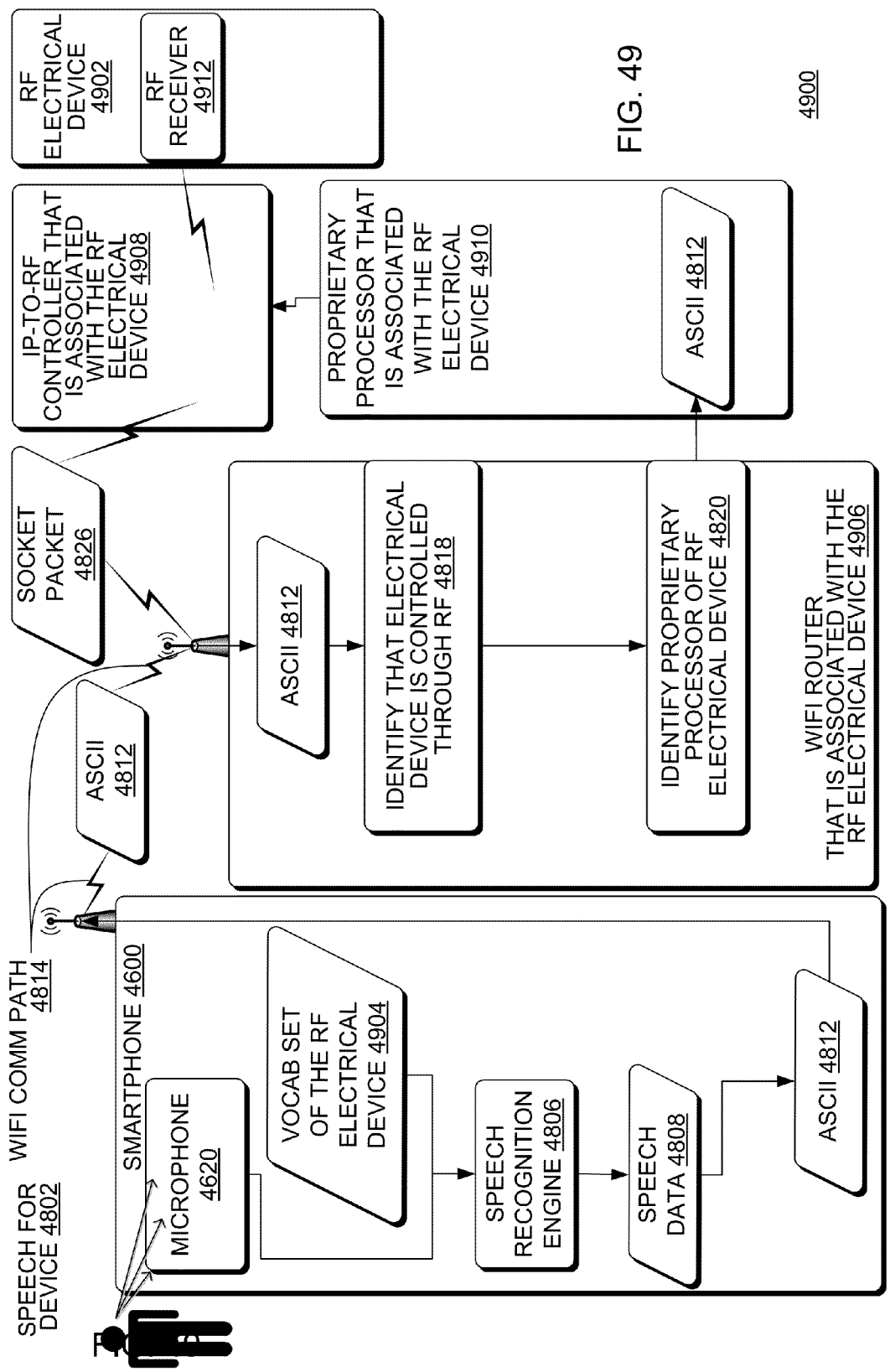
FIG. 49 is a block diagram of a system that is operable to control one or more controllable RF electrical devices from audio speech, the system operable to control the at least one RF controllable device through a wireless communication path, according to an implementation.

FIG. 49 is a block diagram of a system 4900 that is operable to control one or more controllable radio frequency (RF) electrical devices from audio speech, the system operable to control the at least one RF controllable device through a wireless communication path, according to an implementation.

System 4900 includes a microphone 4620 of a wireless mobile device (smartphone) 4600 that is operable to receive audio speech 4802. The audio speech 4802 is associated with the RF controllable electrical device 4902. The RF controllable electrical device 4902 is an electrical device that is controllable via external radio-frequency signal(s).

The wireless mobile device 4600 also includes a speech recognition engine 4806 that is operable to generate speech data 4808 that is associated with a vocabulary set 4904 of the RF controllable electrical device 4902 from the audio speech at the wireless mobile device 4600. The vocabulary set 4904 of the RF controllable electrical device 4902 is a set of vocabulary that includes speech patterns of trigger phrases that are relevant to the RF controllable electrical device 4902. Speech patterns of trigger phrases that are irrelevant to the RF controllable electrical device 4902 are not included in the vocabulary set 4904 of the RF controllable electrical device 4902. For example, when the RF controllable electrical device 4902 is a light, the vocabulary set 4904 of the RF controllable electrical device 4902 includes only trigger phrases "on", "light on", "off" and "light off", and the vocabulary set 4904 of the RF controllable electrical device 4902 excludes speech patterns of all other trigger phrases. In another example, when the RF controllable electrical device 4902 is a patient lift, the vocabulary set 4904 of the RF controllable electrical device 4902 includes only trigger phrases "lower down," "move down," "move forward," "forward," "move backward," "reverse," "goto sleep," "sleep," "faster," "slower," "left," "right," "up," "down," "forward," and "backward", and the vocabulary set 4904 of the RF controllable electrical device 4902 excludes speech patterns of all other trigger phrases. The wireless mobile device 4600 includes vocabulary sets (not shown) of other RF controllable electrical devices and controllable non-RF electrical devices, but the vocabulary set 4904 of the RF controllable electrical device 4902 is selected from among the vocabulary sets all of RF controllable electrical devices and controllable non-RF electrical devices for which the smartphone is configured to control through previous audio speech that identifies the RF controllable electrical device 4902. Having a vocabulary set 4904 in which the speech patterns of trigger phrases that are relevant to only the RF controllable electrical device 4902 is a much smaller vocabulary set than a vocabulary set that includes speech patterns of trigger phrases that are relevant to the other controllable electrical devices. The much smaller size of the vocabulary set 4904 of the RF controllable electrical device 4902 has the effect of greatly increasing the accuracy of the speech data 4808 that is generated by the speech recognition engine 4806, and greatly increases the speed of the speech recognition engine in the process of generating the speech data 4808. Based on the technology of processor and bus speeds of current smartphones, this is the most superior technique to accurately and quickly provide speech data 4808 that is relevant to the RF controllable electrical device 4902 from the audio speech 4802.

The RF controllable electrical device 4902 can be a RF controllable light, a RF controllable patient lift, a RF controllable television, a RF controllable television set-top box, a RF controllable radio, a RF controllable medication dispenser, a RF controllable bed, a RF controllable nurse call device, a RF controllable door, a RF controllable window cover, a RF controllable computer, a RF controllable medical therapeutic device, a RF controllable fan, a RF controllable, a RF controllable lamp, a RF controllable dishwasher, a RF IR controllableon, a RF controllable production machinery, a RF controllable van ramp, a RF controllable cellphone or a RF controllable environmental control.

The wireless mobile device 4600 also includes a component (not shown) that is operable to convert the speech data 4808 to an ASCII string 4812. The ASCII string 4812 identifies the RF controllable electrical device 4902 and represents control data of the RF controllable electrical device 4902 that is indicated by the audio speech 4802.

The communication subsystem 4604 (shown in FIGS. 46 and 47) of the wireless mobile device 4600 establishes a WIFI communication path 4814 with a wireless WIFI wireless router 4906. The WIFI wireless router 4906 is associated with the RF controllable electrical device 4902. The wireless mobile device 4600 is operable to transmit the ASCII string 4812 to the wireless WIFI wireless router 4906 through the WIFI communication path 4814.

The WIFI wireless router 4906 is operable to receive the ASCII string 4812 through the WIFI communication path 4814. The ASCII string 4812 is stored in memory of the WIFI wireless router 4906. The WIFI wireless router 4906 includes a component 4818 that is operable to determine that the RF controllable electrical device 4902 of the ASCII string 4812 is controlled through an RF receiver 4912. The RF receiver 4912 through which the RF controllable electrical device 4902 is controlled is known as an associated RF interface. The WIFI wireless router 4906 includes a component 4820 that is operable to identify a proprietary processor 4910 that is associated with the RF electrical device 4902. The identified proprietary processor 4910 is known as an associated proprietary processor 4910. The WIFI wireless router 4906 is operable to transmit the ASCII string 4812 from the wireless WIFI wireless router 4906 to the associated proprietary processor 4910. In some implementations, the wireless WIFI wireless router 4906 and the proprietary processor 4912 are housed in a single housing.

The proprietary processor 4910 is operable to receive from the WIFI wireless router 4906 the ASCII string 4812 and to store the ASCII string 4812 in memory, operable to identify the RF controllable electrical device 4902 that is controlled through an IP-to-RF controller 4908, such as a GE Smart Remote Plus Transmitter RF102TXPS and the proprietary processor 4910 is operable to set relays of the IP-to-RF controller 4908 based on the ASCII string over a wired connection between the proprietary processor 4910 and the IP-to-RF controller 4908.

The IP-to-RF controller 4908 is operable to transmit at least one RF control signal in accordance with the settings of the relays and the RF controllable electrical device 4902 is operable to receive an RF control signal at the RF interface 4822 and the RF controllable electrical device 4902 is operable to perform a function in accordance with the RF control signal, providing control of the RF controllable electrical device 4902 in accordance with the audio speech 4802.

Not routing a socket packet, such as socket packet 4826 in FIG. 48, through a WIFI wireless router from the proprietary processor 4910 and to the IP-to-RF controller 4908 is particularly important because the IP-to-RF controller 4908 is not required to be in line-of-sight to the RF controllable electrical device 4902 in order for the RF transmission between the IP-to-RF controller 4908 and the RF controllable electrical device 4902 to be effective. Yet in systems where RF controllable electrical devices 4902 are located in different rooms and out of the line-of-sight from the proprietary processor 4910, RF communication, such as via a WIFI wireless router 4816 in FIG. 48, is not necessary in order for the proprietary processor 4910 to communicate to the RF controllable electrical devices 4902 because the IP-to-RF controller 4908 can communicate through walls to the RF controllable electrical devices 4902; and in fact the extra step of communicating between the proprietary processor 4910 and the IP-to-RF controller 4908 through a WIFI wireless router is more complicated and error-prone.

In some implementations, the wireless WIFI wireless router 4816 and the WIFI wireless router 4906 are combined into a single WIFI wireless router and the single WIFI wireless router; the proprietary processor 4824 and the proprietary processor 4910 are combined into a single proprietary processor, the single WIFI wireless router and the single proprietary processor are housed in a single housing.

An important feature of system 4900 is that the ASCII string 4812, relay setting of the IP-to-RF controller 4908 and the RF control signal from the IP-to-RF controller 4908 all represent control data of the at least one controllable electrical device that is indicated by the audio speech 4802. It is through this common representation by the ASCII string 4812, relay setting of the IP-to-RF controller 4908 and the RF control signal from the IP-to-RF controller 4908 of the control data of the RF controllable electrical device 4902 that is indicated by the audio speech 4802, that the audio speech 4802 is effectively communicated across heterogeneous electrical devices, starting at the smartphone 4600 and ending at the RF controllable electrical device 4902.

Figure 50:
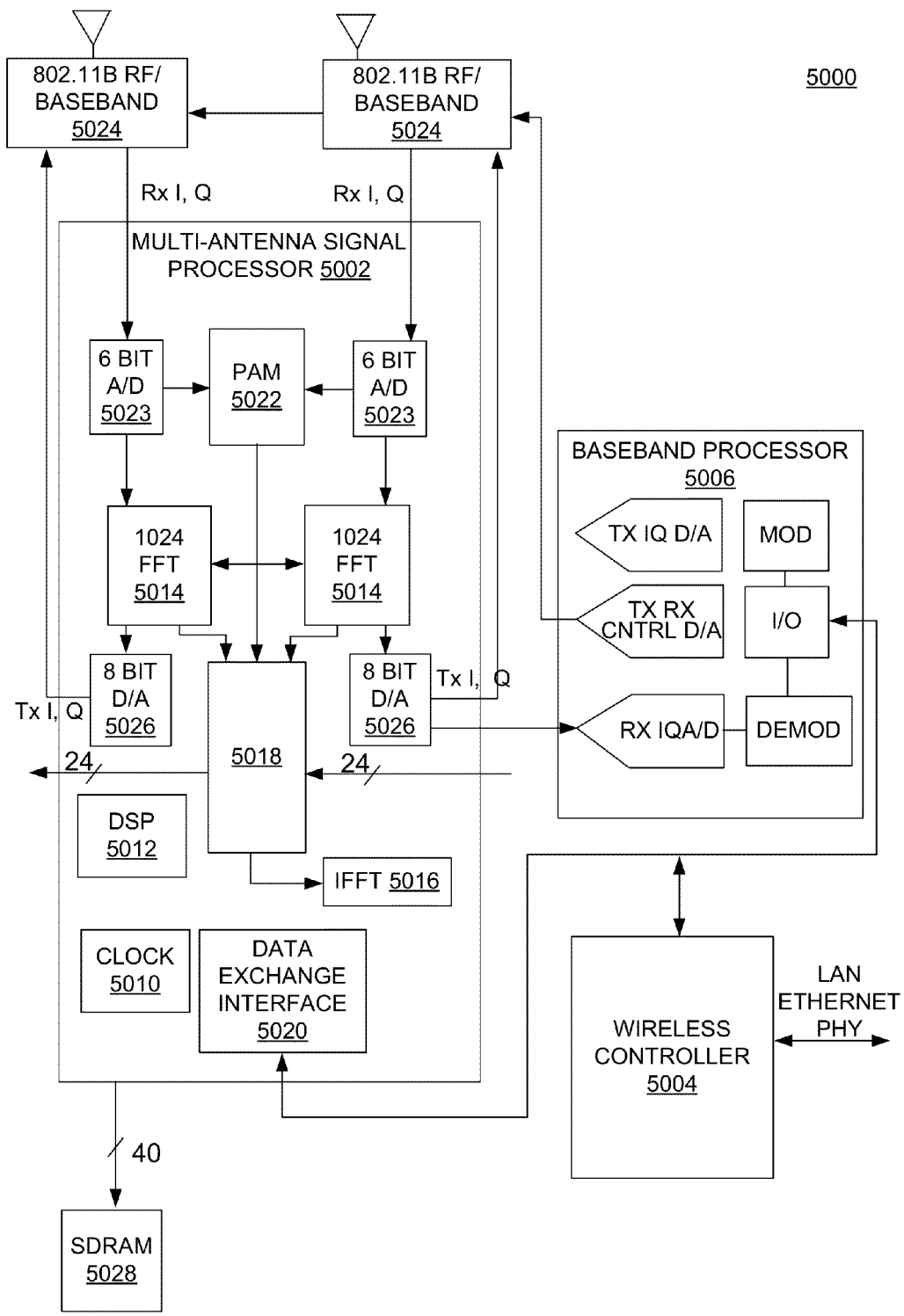
FIG. 50 is a block diagram of a WIFI wireless router according to an implementation. The WIFI wireless router is one example of the WIFI wireless router in FIG. 48 and the WIFI wireless router in FIG. 49.

FIG. 50 is a block diagram of a WIFI wireless router 5000, according to an implementation. The WIFI wireless router 5000 is one example of the WIFI wireless router 4816 in FIG. 48 and the WIFI wireless router 4906 in FIG. 49. The WIFI wireless router 5000 includes a multi-antenna signal processor 5002, a wireless media access controller 5004 and a baseband processor 5006, which can be incorporated as part of a single chip integrated circuit. The functions of items 4818 and 4820 in FIGS. 48 and 49 are embodied and performed by the wireless media access controller 5004. In some implementations, can include a clock generator 5010 which generates a set of clocks for all internal modules from a 44 MHz master clock, a SDRAM buffer interface address generator in a DSP 5012 a 22 mhz three 1024-point FFT switchable circuit 5014 operable to transform received signal samples of multiple RF to the frequency domain using FFT, a 22 mhz three 1024-point IFFT switchable circuit 5016 operable to reconstruct a received signal in the time domain, a separation matrix multiplier 5018 operable to separate signals, an on chip parameter memory bank, an inter-chip data exchange interface 5020 which controls software access to internal registers as well as reading/writing of signaling messages, a digital signal processor interface, a preamble acquisition module (sync-circuit) 5022 operable to acquire timing of the received signal samples relative to a local PN code in a PLCP preamble, synchronize the signal samples to FFT frame, and use the known FFT of a preamble to estimate RF channels, four 6 bit 22 MHz A/D 5023 performs A/D conversion for 1 and Q baseband signals received from RF/Baseband front end circuits 5024, and four 8 bit 44 MHz D/A 5026 operable to convert the recovered signal to an analog form and sending it out to a standard 802.11b DSSS receiver for decoding.

The DSP 5012, which, in combination with SDRAM 5028 and D/A blocks 5026 and other elements of ASIC 5002 performs the following basic operations: Framing of the information bit stream to be transmitted; symbol mapping/encoding of the bits in a transmit frame, scrambling the transmitted data to be transmitted, modulating transmission symbols with Baker or CCK codes necessary for spreading the spectrum of the transmitted data and pre-equalizing the generated waveforms in a frequency domain.

FIG. 51-56 are diagrams 5100-5600 of handheld mobile device graphical user interfaces selected to control electrical devices, according to implementations. The operator of the handheld mobile device can navigate to one of the diagrams 5100-5600, and then a vocabulary set or a linguist component 1616 that is limited to the operations and operands of the electrical device(s) represented in the displayed graphical user interface is referenced during speech recognition of the audio speech to the exclusion of vocabulary sets or a linguist components 1616 that are not associated with the electrical device(s) represented in the displayed graphical user interface. This is an important feature because the selected vocabulary set is specifically limited to the selected controllable electrical device(s). The selected vocabulary set includes data that is relevant only to the selected controllable electrical device, which is greatly helpful in providing faster processing of the audio speech 4802 but also is greatly helpful in providing more accurate processing of the audio speech 4802.

Figure 51:

FIG. 51 is a diagram 5100 of a handheld mobile device graphical user interface selected to control a patient bed electrical device.

Figure 52:
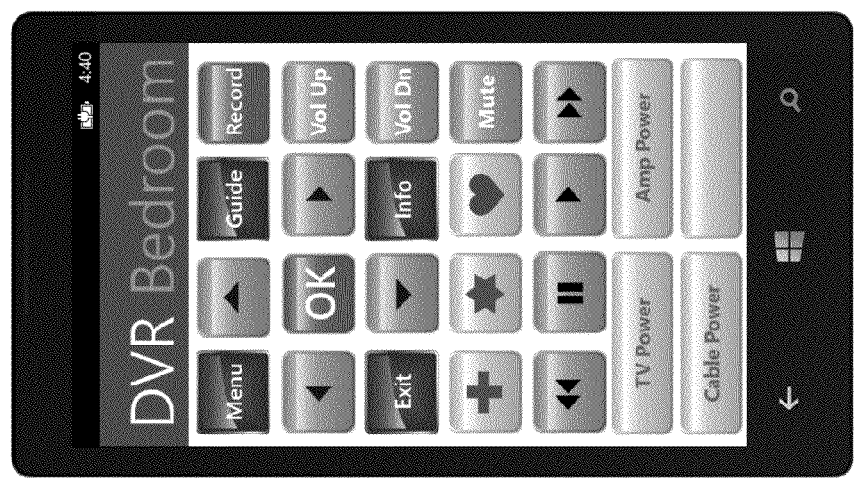

FIG. 52 is a diagram 5200 of a handheld mobile device graphical user interface selected to control a digital video recorder electrical device that is located in a bedroom.

Figure 53:
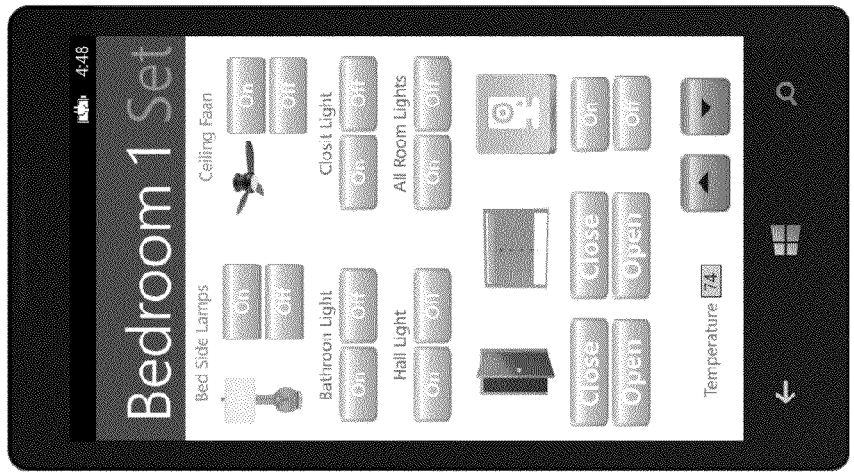
FIG. 51-56 are diagrams of handheld mobile device graphical user interfaces selected to control electrical devices, according to implementations.

FIG. 53 is a diagram 5300 of a handheld mobile device graphical user interface selected to control an electrical devices located in a first bedroom.

Figure 54:

FIG. 54 is a diagram 5400 of a handheld mobile device graphical user interface selected to control a security camera electrical device located at a front door.

Figure 55:
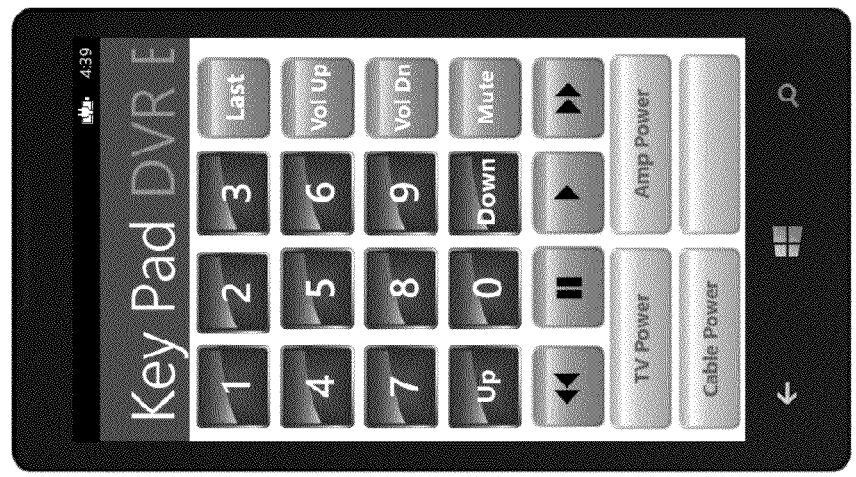

FIG. 55 is a diagram 5500 of a handheld mobile device graphical user interface selected to control a digital video recorder electrical device.

Figure 56:
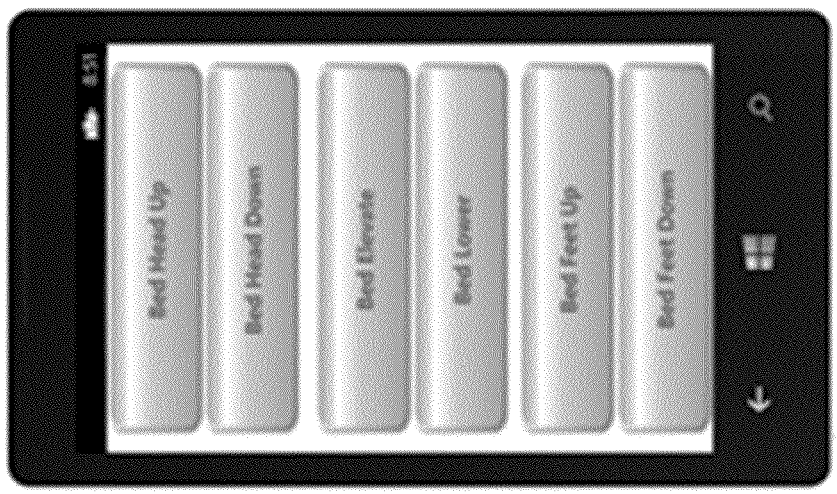

FIG. 56 is a diagram 5600 of a handheld mobile device graphical user interface selected to control a patient bed electrical device.

In some implementations, display screens and command sets are associated in global, local and by room. Global commands can be executed form any location and any room. For example, when the operator selects "Location 1" (either via audio speech 4802 or by selecting "location 1" from a display), the screen of the smartphone will change to display "Location 1" electrical devices and vocabulary set of the electrical device of "location 1" will also be loaded into memory of the smartphone and the vocabulary set for electrical devices that are not associated with "location 1" will be deallocated from memory. In another example, when the operator selects "Make Phone Call" (either via audio speech 4802 or by selecting "phone" from a display), the screen of the smartphone will change to display "phone" functions and vocabulary set of the phone functions will also be loaded into memory of the smartphone and the vocabulary set for electrical devices that are not associated with the phone functions will be deallocated from memory of the smartphone. In another example, when the operator selects "call 911" (either via audio speech 4802 or by selecting "911" from a display), the screen of the smartphone will change to display emergency call functions and vocabulary set of the emergency call functions will also be loaded into memory of the smartphone and the vocabulary set for functions that are not associated with emergency call functions will be deallocated from memory of the smartphone.

Local commands can be from any room in close proximity to the smartphone.

For example, when the operator selects "room 1" (either via audio speech 4802 or by selecting "room 1" from a display), the screen of the smartphone will change to display "room 1" electrical devices of that location and vocabulary set of the electrical device of "room 1" will also be loaded into memory of the smartphone and the vocabulary set for electrical devices that are not associated with "room 1" will be deallocated from memory. The smartphone can be configured to control more than one "Room 1" but each of the "room 1"'s must be in separate locations.

For example, when the operator selects "Open the Front Door" (either via audio speech 4802 or by selecting "Open the Front Door" from a display), the screen of the smartphone will change to display "Front Door" of the building and vocabulary set of the electrical device of "the Front Door" will also be loaded into memory of the smartphone and the vocabulary set for electrical devices that are not associated with "the Front Door" will be deallocated from memory and the front door of the building will be opened from any room in the building.

For example, when the operator selects "Room 3 light on" (either via audio speech 4802 or by selecting "Room 3 light on" from a display), the screen of the smartphone will change to display "Room 3" electrical devices and vocabulary set of the electrical device of "Room 3 light" will also be loaded into memory of the smartphone and the vocabulary set for electrical devices that are not associated with "Room 3 light on" will be deallocated from memory and the light of room 3 of the building will be turned on from any room in the building.

The smartphone can configured to add room commands to the local commands so that functions of electrical devices in any room can be controlled.

Room commands are executable only when that Room Screen is selected by the operator. Room commands are specific to a particular screen so that different electrical devices can be controlled with similar commands. An example would be a two TVs in deferent rooms, each should respond individually to commands like "Turn On" and "Channel Up".

In some implementations, multisensory input is performed from either or both the audio speech 4802 and tactile sensing of selections performed through contact with the touchpad display screen from an external object such as a finger. In that case, control of the electrical devices can be made by the operator through audio speech 4802 and/or by selection via a touchpad display screen on the handheld mobile device.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic non-transitory storage devices, or any other media which can be used to store computer-intelligible information and which can be accessed by the computation resource 4702.

Communication media typically implements computer-readable instructions, data structures, program modules or other data; and includes any information delivery media.

By way of example, and not limitation, communication media include wired media, such as wired network or direct-wired connections, and wireless media, such as acoustic, RF, infrared and other wireless media. The scope of the term computer-readable media includes combinations of any of the above.

Apparatus components of FIG. 1-16 can be implemented as computer hardware circuitry or as a computer-readable program, or a combination of both. In another implementation, system in FIG. 1 and FIG. 2 are implemented in an application service provider (ASP) system.

The terminology used herein is for the purpose of describing particular implementations only and is not intended to limit the inventions. As used herein, the singular forms "a", "an" and "the" are intended to include the plural forms as well, unless the context clearly indicates otherwise. The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited in the form disclosed. Many modifications and variations will be apparent to those of ordinary skill in the art without departing from the scope and spirit of the inventions. Implementations are chosen and described in order to best explain the principles and the practical application, and to enable others of ordinary skill in the art to understand various implementations with various modifications as are suited to the particular use contemplated.

In the above detailed description, reference is made to the accompanying drawings that form a part hereof, and in which is shown by way of illustration specific implementations which may be practiced. These implementations are described in sufficient detail to enable those skilled in the art to practice the implementations, and other implementations may be utilized and that logical, mechanical, electrical and other changes may be made without departing from the scope of the implementations. The following detailed description is, therefore, not to be taken in a limiting sense.

As will be appreciated by one skilled in the art, the present inventions may be implemented as a system, method or computer program product. Accordingly, the present inventions may take the form of an entirely hardware implementation, an entirely software implementation (including firmware, resident software, micro-code, etc.) or an implementation combining software and hardware aspects that may all generally be referred to herein as a "circuit," "module" or "system." Furthermore, the present inventions may take the form of a computer program product implemented in any tangible medium of expression having computer-usable program code implemented in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium do include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical non-transitory storage device, a transmission media such as those supporting the Internet or an intranet, or a magnetic non-transitory storage device. In the context of this document, a computer-usable or computer-readable medium may be any medium that can contain, store, communicate, propagate, or transport the program for use by or in connection with the instruction execution system, apparatus, or device. The computer usable program code may be transmitted using any appropriate medium, including but not limited to wireless, wireline, optical fiber cable, RF, etc.

In computer-readable program implementations, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer environment 4700 in FIG. 47, or on at least as many computers as there are components.

Computer program code for carrying out operations of the present inventions may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present inventions are described above with reference to flowchart illustrations and/or block diagrams of methods, apparatus (systems) and computer program electrical device (s) 114 according to implementations. Each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Some implementations include a computer program product that includes a computer-usable medium having computer-usable program code implemented therewith, the computer-usable program code including computer-usable program code configured to perform specific functions. Some implementations include a field-programmable gate array that is operable to perform specific functions. Some implementations include a computer-accessible medium having executable instructions capable of directing a processor to perform specific functions. Some implementations include a computer-usable medium including a program to control a patient-lifting-device, the program comprising computer program code to perform specific functions. Some method implementations include representing a specific original physical reality with specific original data, electronically transforming the specific original data into specific transformed data using a novel and non-obvious process, and representing the specific transformed data as a specific transformed physical reality in the form of a visual depiction.

CONCLUSION

An omni-input electrical device command system is described. A technical effect of the system is electrical control of one or more electrical devices in reference to commands received from voice input from a hand-held mobile device. Although specific implementations are illustrated and described herein, it will be appreciated by those of ordinary skill in the art that any arrangement which is calculated to achieve the same purpose may be substituted for the specific implementations shown. This application is intended to cover any adaptations or variations. One of ordinary skill in the art will appreciate that implementations can be made in software implementation or any other hardware implementation that provides the required function.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future patient-lifting-devices and different command input devices.

The terminology used in this application meant to include all patient-lifting-devices, and voice recognition systems and alternate technologies which provide the same functionality as described herein.

The invention claimed is:

1. A system that is operable to control at least one IR controllable electrical device from audio speech, the system operable to control the at least one IR controllable electrical device through a wireless communication path, and the system being operable to:
   receive the audio speech that is associated with the at least one IR controllable electrical device at a microphone of a wireless mobile device;
   generate speech data that is associated with a vocabulary set of the at least one IR controllable electrical device from the audio speech at the wireless mobile device;
   convert the speech data to an ASCII string that is associated with the at least one IR controllable electrical device at the wireless mobile device, the ASCII string representing control data of the at least one IR controllable electrical device that is indicated by the audio speech;
   establish a WIFI communication path with a WIFI wireless router that is associated with the at least one IR controllable electrical device at the wireless mobile device;
   send the ASCII string from the wireless mobile device to the WIFI wireless router that is associated with the at least one IR controllable electrical device through the WIFI communication path, the ASCII string representing control data of the at least one IR controllable electrical device that is indicated by the audio speech;
   receive the ASCII string at the WIFI wireless router through the WIFI communication path, the ASCII string representing control data of the at least one IR controllable electrical device that is indicated by the audio speech;
   determine that at the least one IR controllable electrical device of the ASCII string is controlled through an infrared interface, yielding an associated infrared interface, the ASCII string representing control data of the at least one IR controllable electrical device that is indicated by the audio speech;
   determine a proprietary processor that is associated with the associated infrared interface, yielding an associated proprietary processor;
   send the ASCII string from the WIFI wireless router to the associated proprietary processor, the ASCII string representing control data of the at least one IR controllable electrical device that is indicated by the audio speech;
   receive from the router the ASCII string at the associated proprietary processor;
   create a socket packet from the ASCII string at the associated proprietary processor, the socket packet representing control data of the at least one IR controllable electrical device that is indicated by the audio speech;
   send the socket packet from the associated proprietary processor to the WIFI wireless router that is associated with the at least one IR controllable electrical device, the sending having a destination address of an IP-to-IR controller;
   receive the socket packet at the WIFI wireless router that is associated with the at least one IR controllable electrical device from the proprietary processor, the socket packet representing control data of the at least one IR controllable electrical device that is indicated by the audio speech;
   send the socket packet from the WIFI wireless router that is associated with the at least one IR controllable electrical device to the IP-to-IR controller;
   receive the socket packet at the IP-to-IR controller and from the WIFI wireless router that is associated with the at least one IR controllable electrical device, the socket packet representing control data of the at least one IR controllable electrical device that is indicated by the audio speech;
   send an infrared signal in accordance with the socket packet from the IP-to-IR controller to the infrared interface of the at least one IR controllable electrical device, the infrared signal representing control data of the at least one IR controllable electrical device that is indicated by the audio speech;
   receive the infrared signal from the IP-to-IR controller at the infrared interface of the at least one IR controllable electrical device, the infrared signal representing control data of the at least one IR controllable electrical device that is indicated by the audio speech; and perform a function in accordance with the infrared signal at the at least one IR controllable electrical device, providing control of the at least one IR controllable electrical device in accordance with the audio speech.

2. The system of claim 1, further comprising a second socket packet, the second socket packet comprising:
the socket packet; and
the destination IP address of the IP-to-IR controller.

3. The system of claim 2, further comprising a third socket packet, the third socket packet comprising:
the second socket packet; and
a destination IP address of the WIFI wireless router.

4. The system of claim 1, wherein the at least one IR controllable electrical device further comprises:
an IR controllable door.

5. The system of claim 1, wherein the at least one IR controllable electrical device further comprises:
an IR controllable television.

6. The system of claim 1, wherein the at least one IR controllable electrical device further comprises:
an IR controllable DVD player.

7. A method performed by a wireless mobile device to control at least one controllable electrical device from audio speech, the method comprising:
receiving the audio speech that is associated with the at least one controllable electrical device at a microphone of the wireless mobile device;
generating speech data that is associated with a vocabulary set of the at least one controllable electrical device from the audio speech;
converting the speech data to an ASCII string that is associated with the at least one controllable electrical device at the wireless mobile device, the ASCII string representing control data of the at least one controllable electrical device that is indicated by the audio speech;
establishing a WIFI communication path with a WIFI wireless router that is associated with the at least one controllable electrical device at the wireless mobile device; and
sending the ASCII string from the wireless mobile device to the WIFI wireless router that is associated with the at least one controllable electrical device through the WIFI communication path.

8. The method of claim 7, wherein the at least one controllable electrical device further comprises:
a controllable door.

9. The method of claim 7, wherein the at least one controllable electrical device further comprises:
a controllable television.

10. The method of claim 7, wherein the at least one controllable electrical device further comprises:
a controllable DVD player.

11. An apparatus that is operable to control at least one IR controllable electrical device from audio speech, the system operable to control the at least one IR controllable electrical device through a wireless communication path, the apparatus comprising:
a WIFI wireless router comprising a baseband processor and a wireless controller:
the baseband processor being operable to:
establish a WIFI wireless communication path with a wireless mobile device;
receive through the WIFI wireless communication path an ASCII string that represents speech data that is associated with a vocabulary set of the at least one IR controllable electrical device; and
the wireless controller being coupled to the baseband processor and being operable to:
determine that at the least one IR controllable electrical device of the ASCII string is controlled through an infrared interface, yielding an associated infrared interface;
determine a proprietary processor that is associated with the associated infrared interface, yielding an associated proprietary processor; and
send the ASCII string from the wireless WIFI wireless router to the associated proprietary processor; and
the associated proprietary processor coupled to the WIFI wireless router, the associated proprietary processor operable to:
receive the ASCII string from the WIFI wireless router;
create a socket packet from the ASCII string;
send the socket packet the WIFI wireless router, the sending having a destination address of an IP-to-IR controller; and
the WIFI wireless router further comprising:
the wireless controller further operable to:
receive the socket packet from the proprietary processor; and
send the socket packet from the wireless WIFI wireless router to the IP-to-IR controller.

12. The apparatus of claim 11, further comprising a second socket packet, the second socket packet comprising:
the socket packet; and
the destination IP address of the IP-to-IR controller.

13. The apparatus of claim 12, further comprising a third socket packet, the third socket packet comprising:
the second socket packet; and
a destination IP address of the WIFI wireless router.

14. The apparatus of claim 11, wherein the at least one IR controllable electrical device further comprises:
an IR controllable door.

15. The apparatus of claim 11, wherein the at least one IR controllable electrical device further comprises:
an IR controllable television.

16. The apparatus of claim 11, wherein the at least one IR controllable electrical device further comprises:
an IR controllable DVD player.

* * * * *